(12) United States Patent
Larsen et al.

(10) Patent No.: US 10,531,672 B2
(45) Date of Patent: Jan. 14, 2020

(54) POLYPEPTIDES HAVING TRANSGALACTOSYLATING ACTIVITY

(71) Applicant: DuPont Nutrition Biosciences APS, Copenhagen (DK)

(72) Inventors: Morten Larsen, Krog (DK); Jacob Cramer, Flyvholm (DK)

(73) Assignee: DuPont Nutrition Biosciences ApS (DK)

( * ) Notice: Subject to any disclaimer, the term of this patent is extended or adjusted under 35 U.S.C. 154(b) by 88 days.

(21) Appl. No.: 14/405,072

(22) PCT Filed: Jun. 7, 2013

(86) PCT No.: PCT/EP2013/061819
§ 371 (c)(1),
(2) Date: Dec. 2, 2014

(87) PCT Pub. No.: WO2013/182686
PCT Pub. Date: Dec. 12, 2013

(65) Prior Publication Data
US 2015/0223481 A1    Aug. 13, 2015

Related U.S. Application Data

(60) Provisional application No. 61/657,180, filed on Jun. 8, 2012.

(30) Foreign Application Priority Data

Jun. 8, 2012 (EP) .................................... 12171335

(51) Int. Cl.
*C12N 9/38* (2006.01)
*A23C 9/12* (2006.01)

(52) U.S. Cl.
CPC .......... *A23C 9/1206* (2013.01); *C12N 9/2471* (2013.01)

(58) Field of Classification Search
CPC .................................................... C12N 9/2471
USPC ....................................................... 435/207
See application file for complete search history.

(56) References Cited

U.S. PATENT DOCUMENTS

| | | |
|---|---|---|
| 5,874,276 A | 2/1999 | Fowler et al. |
| 6,022,725 A | 2/2000 | Fowler et al. |
| 6,268,328 B1 | 7/2001 | Mitchinson et al. |
| 6,555,348 B2 * | 4/2003 | Jørgensen et al. ... C12N 9/2471 426/582 |
| 6,667,065 B1 | 12/2003 | Kragh et al. |
| 7,081,355 B2 | 7/2006 | Jorgensen et al. |
| 9,516,888 B2 | 12/2016 | Katase et al. |
| 10,058,107 B2 * | 8/2018 | Hendriksen ......... A23C 9/1206 |
| 2004/0043109 A1 | 3/2004 | Kragh et al. |
| 2005/0037391 A1 | 2/2005 | Kragh et al. |
| 2005/0112237 A1 | 5/2005 | Kragh et al. |
| 2005/0137111 A1 | 6/2005 | Kragh et al. |
| 2006/0008888 A1 | 1/2006 | Kragh et al. |
| 2006/0008890 A1 | 1/2006 | Kragh et al. |
| 2006/0018997 A1 | 1/2006 | Kragh et al. |
| 2006/0019347 A1 | 1/2006 | Cho et al. |
| 2006/0073583 A1 | 4/2006 | Kragh et al. |
| 2007/0020727 A1 | 1/2007 | Berg et al. |
| 2007/0020731 A1 | 1/2007 | Kragh et al. |
| 2007/0072270 A1 | 3/2007 | Kragh et al. |
| 2007/0141693 A1 | 6/2007 | Berg et al. |
| 2010/0285175 A1 | 11/2010 | Hendriksen et al. |
| 2015/0037847 A1 | 2/2015 | Bertelsen et al. |

FOREIGN PATENT DOCUMENTS

| | | |
|---|---|---|
| EP | 0215594 A2 | 3/1987 |
| EP | 0244234 A2 | 4/1987 |
| JP | 2003534007 | 11/2003 |
| WO | 0190317 A2 | 11/2001 |
| WO | WO2001/090317 A2 | 11/2001 |
| WO | WO2001/90317 A2 | 11/2001 |
| WO | 2009071539 A1 | 6/2009 |
| WO | WO2009/071537 A1 | 6/2009 |
| WO | WO2009/071539 A1 | 11/2009 |
| WO | 2010140435 | 12/2010 |
| WO | 2011120993 A1 | 10/2011 |
| WO | 2012010597 A1 | 1/2012 |
| WO | WO2012/010597 A1 | 1/2012 |
| WO | WO2013/182686 A1 | 12/2013 |

OTHER PUBLICATIONS

WrittenOpinion.ISA report from PCTEP2013.061819 (dated 2013).*
Jorgensen et al., Appl. Microbiol. Biotechnol., 2001, vol. 57, pp. 647-652.
GenBank: CAC14566.2, Aug. 5, 2003.
ISR issued for PCT/EP2013/061819 dated Jul. 19, 2013.
Written Opinion issued for PCT/EP2013/061819 dated Jul. 19, 2013.
Campbell et al., "Improved transformation efficiency of *Aspergillus niger* using the homologous niaD gene for nitrate reductase", Current Genetics, 1989, vol. 16, pp. 53-56.
Altschul et al., "Basic Local Alignment Seach Tool", J. Mol. Biol., 1990, vol. 215, pp. 403-410.
Bolton et al., "A General Method for the Isolation of RNA Complementary to DNA" Biochemistry: Bolton and McCarthy, vol. 48, pp. 1390-1397.
Henrissat et al., "Structural and Sequence-based Classification of glycoside", Current Opinion in Structural Biology, 1997, vol. 7, No. 5, pp. 637-64.
Hunter et al. "InterPro: the integrative protein signature database", Nucleic Acids Research, 2009, vol. 37, database D21-D215.
Finn et al., "The Pfam protein families database", Nucleic Acids Research, 2010, vol. 38, database D211-D222.

(Continued)

*Primary Examiner* — Tekchand Saidha

(57) ABSTRACT

The present invention relates to polypeptides, specifically polypeptides having transgalactosylating activity and nucleic acids encoding these, and their uses in e.g. dairy product.

11 Claims, 5 Drawing Sheets

Specification includes a Sequence Listing.

(56) References Cited

OTHER PUBLICATIONS

Harkki et al., "A Novel Fungal Expression System: Secretion of Active Calf Chymosin From the Filamentous Fungus *Trichoderma Reeser*", Nature Publishing Group, 1989, vol. 7, pp. 596-603.
Harkki et al., "Genetic engineering of Trichoderman to produce strains with novel cellulase profiles", Enzyme Microb. Technol., 1991, vol. 13, pp. 227.
Kelly et al., "Transformation of *Aspergillus niger* by the *amdS* gene of *Aspergillus nidulans*", The EMBO Journal, 1989, vol. 4, No. 2, pp. 475-479.
Needleman et al., "A General Method Applicable to the Search for Similarities in the Amino Acid Sequence of Two Proteins", Journal of Molecular Biology, 1970, vol. 48, pp. 443-453.
Penttila et al., "A Versatile Transformative System for the Cellulolytic Filamentous *Fungus Trichoderma reesei*", Gene, 1987, vol. 61, pp. 155-164.
Jenkins et al. "β-Glucosidase, β-galactosidase, family A cellulases, family F xylanases and two barely glycanases form a superfamily of enzymes with 8-fold β/αarchitecture and with two conserved glutamates near the carboxy-terminal ends of β-strands four and seven", FEBS Letters, 1995, vol. 362, pp. 281-285.
Jorgensen et al., "High-efficiency synthesis of oligosaccharides with a truncated β- galactosidase from Bifidobacterium bifidum", Appl Microbiol Biotechnol, 2001, vol. 57, pp. 647-652.
Wierenga, "The TIM-barrel fold: a versatile framework for efficient enzymes", FEBS Letters, 2001, vol. 492, pp. 193-198.
Opposition by Novozymes A/S, EP 2 859 098 B, Application No. 13727611.9, Jun. 12, 2018.
Opposed by Novozymes A/S, Supplementary Submission, EP 2 859 098 B, Application No. 13727611.9, May 7, 2019.
Sequence Comparisons of Prior Art Sequences with SEQ ID No:1 and SEQ ID No:2 of EP 2859 098 (DuPont Nutrition Biosciences ApS).
GenBank: AJ224435.2 "Bifidobacterium bifidum gene for beta-galactosidase (5509 bp)", Aug. 5, 2003.

Moller et al., "Intra- and Extracellular β-Galactosidases from *Bifidobacterium bifidum* and *B. infantis*: Molecular Cloning, Heterologous Expression, and Comparative Characterization", Applied and Environmental Microbiology, Microbiology, 2001, vol. 65, No. 5, pp. 2276-2283.
Declaration of Anne Breuner.
Declaration of Jeppe Wegener Tams.
USPTO Non-Final Office Action dated Apr. 22, 2016.
Declaration of Peter Stougaard.
Declaration of Cristina Bongiorni.
GenBank: AJ224435.1 "Bifidobacterium bifidum gene for beta-galactosidase (5509 bp)", Oct. 26, 2000.
"Clustal Omega" Multiple Sequence Alignment, www.ebi.ac.uk.com.
Declaration of Jacob Flyvholm Cramer.
GenBank: CACI 4566.2 "beta-galactosidase" Aug. 5, 2003.
Briggs et al., "Molecular Mechanisms of Protein Secretion: The Role of the Signal Sequence", Advances in Protein Chemistry, 1986, vol. 38, pp. 109.
SignalP 4.0 Server—Prediction results "Novo Nordisk Scientific Computing".
Needleman-Wunsch, Calculation of Seq. ID between Amino Acids 1-979.
Alignment of AJ224435.1 and AJ224435.2 show two frameshifts.
Declaration of Anders Michael Bernth Giessing.
Summons to attend oral proceedings pursuant to Rule 115(1) EPC; EP Application No. 13727611.9, dated Mar. 4, 2019.
International Preliminary Report on Patentability; International Application No. PCT/EP2013/061819; International Filing Date Jun. 7, 2013.
Communication pursuant to Rule 161(1) and 162 EPC; Application No. 13727611.9-1406; Dated Feb. 10, 2015.
Communication pursuant to Article 94(3) EPC; Application No. 13 727 611.9-1410; Dated Aug. 22, 2016.
Invitation pursuant to Article 94(3) and Rule 71(1) EPC; Application No. 13727 611.9-1410; Dated Feb. 7, 2017.

* cited by examiner

A1 B1 A2 B2 A3 B3 A4 B4 A5 B5 A6 B6 A7 B7 A8 B8 A9 B9 A10 B10

C1 D1 C2 D2 C3 D3 C4 D4 C5 D5 C6 D6 C7 D7 C8 D8 C9 D9 C10 D10

E1 F1 E2 F2 E3 F3 E4 F4 E5 F5 E6 F6 E7 F7 E8 F8 E9 F9

G1 H1 G2 H2 G3 H3 G4 H4 G5 H5 G6 H6 G7 H7 G8 H8 G9 H9 G10 H10

SEQUENCE LISTING

<160> NUMBER OF SEQ ID NOS: 23

<210> SEQ ID NO 1
<211> LENGTH: 887
<212> TYPE: PRT
<213> ORGANISM: Bifidobacterium bifidum
<220> FEATURE:
<221> NAME/KEY: SOURCE
<222> LOCATION: 1..887
<223> OTHER INFORMATION: /mol_type="protein"
    /organism="Bifidobacterium bifidum"

<400> SEQUENCE: 1

```
Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60
```

-continued

```
Pro His Asp Tyr Ser Ile Thr Gln Lys Tyr Ser Gln Ser Asn Glu Ala
 65                  70                  75                  80

Glu Ser Ala Tyr Leu Pro Gly Gly Thr Gly Trp Tyr Arg Lys Ser Phe
                 85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
```

```
            485                 490                 495
Gly Asp Asn Leu Thr Ala Asn Gly Gly Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
        530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
        610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
        770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Ala Val Pro
865                 870                 875                 880

Gly Thr Ser Thr Glu Lys Thr
                885

<210> SEQ ID NO 2
```

```
<211> LENGTH: 965
<212> TYPE: PRT
<213> ORGANISM: Bifidobacterium bifidum
<220> FEATURE:
<221> NAME/KEY: SOURCE
<222> LOCATION: 1..965
<223> OTHER INFORMATION: /mol_type="protein"
      /organism="Bifidobacterium bifidum"

<400> SEQUENCE: 2
```

Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Gly Asp Val Thr Met
            195                 200                 205

Asn Leu Thr Thr Lys Val Ala Asn Asp Thr Glu Ala Ala Ala Asn Ile
210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
            355                 360                 365

```
Ile Asp Val Cys Asn Glu Lys Gly Val Leu Val Glu Glu Val Phe
370             375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
            405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
770                 775                 780
```

-continued

```
Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu
                965

<210> SEQ ID NO 3
<211> LENGTH: 1038
<212> TYPE: PRT
<213> ORGANISM: Bifidobacterium bifidum
<220> FEATURE:
<221> NAME/KEY: SOURCE
<222> LOCATION: 1..1038
<223> OTHER INFORMATION: /mol_type="protein"
      /organism="Bifidobacterium bifidum"

<400> SEQUENCE: 3

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160
```

-continued

```
Leu Pro Ser Ser Arg Trp Tyr Ser Gly Ser Gly Ile Tyr Arg Asp Val
            165                 170                 175
Thr Leu Thr Val Thr Asp Gly Val His Val Gly Asn Asn Gly Val Ala
        180                 185                 190
Ile Lys Thr Pro Ser Leu Ala Thr Gln Asn Gly Gly Asp Val Thr Met
        195                 200                 205
Asn Leu Thr Thr Lys Val Ala Asn Asp Thr Glu Ala Ala Ala Asn Ile
    210                 215                 220
Thr Leu Lys Gln Thr Val Phe Pro Lys Gly Lys Thr Asp Ala Ala
225                 230                 235                 240
Ile Gly Thr Val Thr Thr Ala Ser Lys Ser Ile Ala Ala Gly Ala Ser
            245                 250                 255
Ala Asp Val Thr Ser Thr Ile Thr Ala Ala Ser Pro Lys Leu Trp Ser
            260                 265                 270
Ile Lys Asn Pro Asn Leu Tyr Thr Val Arg Thr Glu Val Leu Asn Gly
        275                 280                 285
Gly Lys Val Leu Asp Thr Tyr Asp Thr Glu Tyr Gly Phe Arg Trp Thr
    290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
            325                 330                 335
Ala Asn Arg Arg Ala Ile Glu Arg Gln Val Glu Ile Leu Gln Lys Met
            340                 345                 350
Gly Val Asn Ser Ile Arg Thr Thr His Asn Pro Ala Ala Lys Ala Leu
        355                 360                 365
Ile Asp Val Cys Asn Glu Lys Gly Val Leu Val Glu Glu Val Phe
    370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
            405                 410                 415
Lys Asp Glu Thr Trp Ala Lys Phe Asp Leu Thr Ser Thr Ile Asn Arg
        420                 425                 430
Asp Arg Asn Ala Pro Ser Val Ile Met Trp Ser Leu Gly Asn Glu Met
    435                 440                 445
Met Glu Gly Ile Ser Gly Ser Val Ser Gly Phe Pro Ala Thr Ser Ala
    450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
            485                 490                 495
Gly Asp Asn Leu Thr Ala Asn Gly Gly Val Val Gly Thr Asn Tyr Ser
        500                 505                 510
Asp Gly Ala Asn Tyr Asp Lys Ile Arg Thr Thr His Pro Ser Trp Ala
        515                 520                 525
Ile Tyr Gly Ser Glu Thr Ala Ser Ala Ile Asn Ser Arg Gly Ile Tyr
    530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
            565                 570                 575
Tyr Asp Val Val Gln Arg Asp Phe Val Ala Gly Thr Tyr Val Trp Thr
```

-continued

```
                580             585             590
Gly Phe Asp Tyr Leu Gly Glu Pro Thr Pro Trp Asn Gly Thr Gly Ser
            595                 600                 605
Gly Ala Val Gly Ser Trp Pro Ser Pro Lys Asn Ser Tyr Phe Gly Ile
        610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
            645                 650                 655
Glu Asn Val Val Ala Lys Gly Ser Gly Asn Asn Val Pro Val Val Val
        660                 665                 670
Tyr Thr Asp Ala Ala Lys Val Lys Leu Tyr Phe Thr Pro Lys Gly Ser
    675                 680                 685
Thr Glu Lys Arg Leu Ile Gly Glu Lys Ser Phe Thr Lys Lys Thr Thr
    690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
            725                 730                 735
Gly Thr Ile Ser Ala Glu Ala Tyr Asp Glu Asn Asn Arg Leu Ile Pro
        740                 745                 750
Glu Gly Ser Thr Glu Gly Asn Ala Ser Val Thr Thr Thr Gly Lys Ala
    755                 760                 765
Ala Lys Leu Lys Ala Asp Ala Asp Arg Lys Thr Ile Thr Ala Asp Gly
    770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
            805                 810                 815
Gly Lys Leu Val Gly Val Asp Asn Gly Ser Ser Pro Asp His Asp Ser
        820                 825                 830
Tyr Gln Ala Asp Asn Arg Lys Ala Phe Ser Gly Lys Val Leu Ala Ile
    835                 840                 845
Val Gln Ser Thr Lys Glu Ala Gly Glu Ile Thr Val Thr Ala Lys Ala
    850                 855                 860
Asp Gly Leu Gln Ser Ser Thr Val Lys Ile Ala Thr Ala Val Pro
865                 870                 875                 880
Gly Thr Ser Thr Glu Lys Thr Val Arg Ser Phe Tyr Tyr Ser Arg Asn
            885                 890                 895
Tyr Tyr Val Lys Thr Gly Asn Lys Pro Ile Leu Pro Ser Asp Val Glu
        900                 905                 910
Val Arg Tyr Ser Asp Gly Thr Ser Asp Arg Gln Asn Val Thr Trp Asp
    915                 920                 925
Ala Val Ser Asp Asp Gln Ile Ala Lys Ala Gly Ser Phe Ser Val Ala
    930                 935                 940
Gly Thr Val Ala Gly Gln Lys Ile Ser Val Arg Val Thr Met Ile Asp
945                 950                 955                 960
Glu Ile Gly Ala Leu Leu Asn Tyr Ser Ala Ser Thr Pro Val Gly Thr
            965                 970                 975
Pro Ala Val Leu Pro Gly Ser Arg Pro Ala Val Leu Pro Asp Gly Thr
        980                 985                 990
Val Thr Ser Ala Asn Phe Ala Val His Trp Thr Lys Pro Ala Asp Thr
    995                 1000                1005
```

Val Tyr Asn Thr Ala Gly Thr Val Lys Val Pro Gly Thr Ala Thr Val
    1010                1015                1020

Phe Gly Lys Glu Phe Lys Val Thr Ala Thr Ile Arg Val Gln
1025                1030                1035

<210> SEQ ID NO 4
<211> LENGTH: 1142
<212> TYPE: PRT
<213> ORGANISM: Bifidobacterium bifidum
<220> FEATURE:
<221> NAME/KEY: SOURCE
<222> LOCATION: 1..1142
<223> OTHER INFORMATION: /mol_type="protein"
      /organism="Bifidobacterium bifidum"

<400> SEQUENCE: 4

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Gly Asp Val Thr Met
            195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

```
Leu Lys Gly Val Ser Met His His Asp Gln Gly Ser Leu Gly Ala Val
            325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
            370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
            450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
            485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
            610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
            645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
            690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
            725                 730                 735
```

```
Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
        770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
        820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
        850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
        900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
        930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
        980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr Val
        1010                1015                1020

Phe Gly Lys Glu Phe Lys Val Thr Ala Thr Ile Arg Val Gln Arg Ser
1025                1030                1035                1040

Gln Val Thr Ile Gly Ser Ser Val Ser Gly Asn Ala Leu Arg Leu Thr
        1045                1050                1055

Gln Asn Ile Pro Ala Asp Lys Gln Ser Asp Thr Leu Asp Ala Ile Lys
        1060                1065                1070

Asp Gly Ser Thr Thr Val Asp Ala Asn Thr Gly Gly Ala Asn Pro
        1075                1080                1085

Ser Ala Trp Thr Asn Trp Ala Tyr Ser Lys Ala Gly His Asn Thr Ala
        1090                1095                1100

Glu Ile Thr Phe Glu Tyr Ala Thr Glu Gln Gln Leu Gly Gln Ile Val
1105                1110                1115                1120

Met Tyr Phe Phe Arg Asp Ser Asn Ala Val Arg Phe Pro Asp Ala Gly
                1125                1130                1135

Lys Thr Lys Ile Gln Ile
        1140
```

-continued

```
<210> SEQ ID NO 5
<211> LENGTH: 1211
<212> TYPE: PRT
<213> ORGANISM: Bifidobacterium bifidum
<220> FEATURE:
<221> NAME/KEY: SOURCE
<222> LOCATION: 1..1211
<223> OTHER INFORMATION: /mol_type="protein"
      /organism="Bifidobacterium bifidum"

<400> SEQUENCE: 5

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Asp Val Thr Met
            195                 200                 205

Asn Leu Thr Thr Lys Val Ala Asn Asp Thr Glu Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
```

```
            355                 360                 365
Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
        420                 425                 430

Asp Arg Asn Ala Pro Ser Val Ile Met Trp Ser Leu Gly Asn Glu Met
435                 440                 445

Met Glu Gly Ile Ser Gly Ser Val Ser Gly Phe Pro Ala Thr Ser Ala
        450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
        610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
770                 775                 780
```

```
Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
            805                 810                 815

Gly Lys Leu Val Gly Val Asp Asn Gly Ser Ser Pro Asp His Asp Ser
        820                 825                 830

Tyr Gln Ala Asp Asn Arg Lys Ala Phe Ser Gly Lys Val Leu Ala Ile
    835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr Val
    1010                1015                1020

Phe Gly Lys Glu Phe Lys Val Thr Ala Thr Ile Arg Val Gln Arg Ser
1025                1030                1035                1040

Gln Val Thr Ile Gly Ser Ser Val Ser Gly Asn Ala Leu Arg Leu Thr
                1045                1050                1055

Gln Asn Ile Pro Ala Asp Lys Gln Ser Asp Thr Leu Asp Ala Ile Lys
            1060                1065                1070

Asp Gly Ser Thr Thr Val Asp Ala Asn Thr Gly Gly Ala Asn Pro
        1075                1080                1085

Ser Ala Trp Thr Asn Trp Ala Tyr Ser Lys Ala Gly His Asn Thr Ala
    1090                1095                1100

Glu Ile Thr Phe Glu Tyr Ala Thr Glu Gln Gln Leu Gly Gln Ile Val
1105                1110                1115                1120

Met Tyr Phe Phe Arg Asp Ser Asn Ala Val Arg Phe Pro Asp Ala Gly
                1125                1130                1135

Lys Thr Lys Ile Gln Ile Ser Ala Asp Gly Lys Asn Trp Thr Asp Leu
            1140                1145                1150

Ala Ala Thr Glu Thr Ile Ala Ala Gln Glu Ser Ser Asp Arg Val Lys
        1155                1160                1165

Pro Tyr Thr Tyr Asp Phe Ala Pro Val Gly Thr Phe Val Lys Val
    1170                1175                1180

Thr Val Thr Asn Ala Asp Thr Thr Thr Pro Ser Gly Val Val Cys Ala
1185                1190                1195                1200
```

```
Gly Leu Thr Glu Ile Glu Leu Lys Thr Ala Thr
            1205                1210

<210> SEQ ID NO 6
<211> LENGTH: 1296
<212> TYPE: PRT
<213> ORGANISM: Bifidobacterium bifidum
<220> FEATURE:
<221> NAME/KEY: SOURCE
<222> LOCATION: 1..1296
<223> OTHER INFORMATION: /mol_type="protein"
      /organism="Bifidobacterium bifidum"

<400> SEQUENCE: 6

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His Asp Gln Gly Ser Leu Gly Ala Val
                325                 330                 335
```

-continued

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Val Glu Glu Val Phe
        370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Thr Gly Lys Ala

```
                    755                 760                 765
Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr Val
    1010                1015                1020

Phe Gly Lys Glu Phe Lys Val Thr Ala Thr Ile Arg Val Gln Arg Ser
1025                1030                1035                1040

Gln Val Thr Ile Gly Ser Ser Val Ser Gly Asn Ala Leu Arg Leu Thr
                1045                1050                1055

Gln Asn Ile Pro Ala Asp Lys Gln Ser Asp Thr Leu Asp Ala Ile Lys
            1060                1065                1070

Asp Gly Ser Thr Thr Val Asp Ala Asn Thr Gly Gly Ala Asn Pro
        1075                1080                1085

Ser Ala Trp Thr Asn Trp Ala Tyr Ser Lys Ala Gly His Asn Thr Ala
    1090                1095                1100

Glu Ile Thr Phe Glu Tyr Ala Thr Glu Gln Gln Leu Gly Gln Ile Val
1105                1110                1115                1120

Met Tyr Phe Phe Arg Asp Ser Asn Ala Val Arg Phe Pro Asp Ala Gly
                1125                1130                1135

Lys Thr Lys Ile Gln Ile Ser Ala Asp Gly Lys Asn Trp Thr Asp Leu
            1140                1145                1150

Ala Ala Thr Glu Thr Ile Ala Ala Gln Glu Ser Ser Asp Arg Val Lys
        1155                1160                1165

Pro Tyr Thr Tyr Asp Phe Ala Pro Val Gly Ala Thr Phe Val Lys Val
    1170                1175                1180
```

```
Thr Val Thr Asn Ala Asp Thr Thr Pro Ser Gly Val Val Cys Ala
1185                1190                1195                1200

Gly Leu Thr Glu Ile Glu Leu Lys Thr Ala Thr Ser Lys Phe Val Thr
                1205                1210                1215

Asn Thr Ser Ala Ala Leu Ser Ser Leu Thr Val Asn Gly Thr Lys Val
                1220                1225                1230

Ser Asp Ser Val Leu Ala Ala Gly Ser Tyr Asn Thr Pro Ala Ile Ile
            1235                1240                1245

Ala Asp Val Lys Ala Glu Gly Glu Gly Asn Ala Ser Val Thr Val Leu
            1250                1255                1260

Pro Ala His Asp Asn Val Ile Arg Val Ile Thr Glu Ser Glu Asp His
1265                1270                1275                1280

Val Thr Arg Lys Thr Phe Thr Ile Asn Leu Gly Thr Glu Gln Glu Phe
                1285                1290                1295

<210> SEQ ID NO 7
<211> LENGTH: 453
<212> TYPE: PRT
<213> ORGANISM: Bifidobacterium bifidum
<220> FEATURE:
<221> NAME/KEY: SOURCE
<222> LOCATION: 1..453
<223> OTHER INFORMATION: /mol_type="protein"
      /note="Glycoside hydrolase catalytic core"
      /organism="Bifidobacterium bifidum"

<400> SEQUENCE: 7

Gln Asn Arg Thr Ser Asp Phe Asp Ala Asn Trp Lys Phe Met Leu Ser
1               5                   10                  15

Asp Ser Val Gln Ala Gln Asp Pro Ala Phe Asp Ser Ala Trp Gln
            20                  25                  30

Gln Val Asp Leu Pro His Asp Tyr Ser Ile Thr Gln Lys Tyr Ser Gln
        35                  40                  45

Ser Asn Glu Ala Glu Ser Ala Tyr Leu Pro Gly Gly Thr Gly Trp Tyr
    50                  55                  60

Arg Lys Ser Phe Thr Ile Asp Arg Asp Leu Ala Gly Lys Arg Ile Ala
65                  70                  75                  80

Ile Asn Phe Asp Gly Val Tyr Met Asn Ala Thr Val Trp Phe Asn Gly
                85                  90                  95

Val Lys Leu Gly Thr His Pro Tyr Gly Tyr Ser Pro Phe Ser Phe Asp
            100                 105                 110

Leu Thr Gly Asn Ala Lys Phe Gly Gly Glu Asn Thr Ile Val Val Lys
        115                 120                 125

Val Glu Asn Arg Leu Pro Ser Ser Arg Trp Tyr Ser Gly Ser Gly Ile
    130                 135                 140

Tyr Arg Asp Val Thr Leu Thr Val Thr Asp Gly Val His Val Gly Asn
145                 150                 155                 160

Asn Gly Val Ala Ile Lys Thr Pro Ser Leu Ala Thr Gln Asn Gly Gly
                165                 170                 175

Asp Val Thr Met Asn Leu Thr Lys Val Ala Asn Asp Thr Glu Ala
            180                 185                 190

Ala Ala Asn Ile Thr Leu Lys Gln Thr Val Phe Pro Lys Gly Gly Lys
        195                 200                 205

Thr Asp Ala Ala Ile Gly Thr Val Thr Ala Ser Lys Ser Ile Ala
    210                 215                 220

Ala Gly Ala Ser Ala Asp Val Thr Ser Thr Ile Thr Ala Ala Ser Pro
```

```
                225                 230                 235                 240
Lys Leu Trp Ser Ile Lys Asn Pro Asn Leu Tyr Thr Val Arg Thr Glu
                    245                 250                 255

Val Leu Asn Gly Gly Lys Val Leu Asp Thr Tyr Asp Thr Glu Tyr Gly
                260                 265                 270

Phe Arg Trp Thr Gly Phe Asp Ala Thr Ser Gly Phe Ser Leu Asn Gly
            275                 280                 285

Glu Lys Val Lys Leu Lys Gly Val Ser Met His His Asp Gln Gly Ser
        290                 295                 300

Leu Gly Ala Val Ala Asn Arg Arg Ala Ile Glu Arg Gln Val Glu Ile
305                 310                 315                 320

Leu Gln Lys Met Gly Val Asn Ser Ile Arg Thr His Asn Pro Ala
                325                 330                 335

Ala Lys Ala Leu Ile Asp Val Cys Asn Glu Lys Gly Val Leu Val Val
                340                 345                 350

Glu Glu Val Phe Asp Met Trp Asn Arg Ser Lys Asn Gly Asn Thr Glu
            355                 360                 365

Asp Tyr Gly Lys Trp Phe Gly Gln Ala Ile Ala Gly Asp Asn Ala Val
        370                 375                 380

Leu Gly Gly Asp Lys Asp Glu Thr Trp Ala Lys Phe Asp Leu Thr Ser
385                 390                 395                 400

Thr Ile Asn Arg Asp Arg Asn Ala Pro Ser Val Ile Met Trp Ser Leu
                405                 410                 415

Gly Asn Glu Met Met Glu Gly Ile Ser Gly Ser Val Ser Gly Phe Pro
            420                 425                 430

Ala Thr Ser Ala Lys Leu Val Ala Trp Thr Lys Ala Ala Asp Ser Thr
        435                 440                 445

Arg Pro Met Thr Tyr
        450

<210> SEQ ID NO 8
<211> LENGTH: 5160
<212> TYPE: DNA
<213> ORGANISM: Bifidobacterium bifidum
<220> FEATURE:
<221> NAME/KEY: source
<222> LOCATION: 1..5160
<223> OTHER INFORMATION: /mol_type="DNA"
      /organism="Bifidobacterium bifidum"

<400> SEQUENCE: 8
```

| | | | | | |
|---|---|---|---|---|---|
| gcagttgaag | atgcaacaag | aagcgatagc | acaacacaaa | tgtcatcaac | accggaagtt | 60 |
| gtttattcat | cagcggtcga | tagcaaacaa | aatcgcacaa | gcgattttga | tgcgaactgg | 120 |
| aaatttatgc | tgtcagatag | cgttcaagca | caagatccgg | catttgatga | ttcagcatgg | 180 |
| caacaagttg | atctgccgca | tgattatagc | atcacacaga | aatatagcca | aagcaatgaa | 240 |
| gcagaatcag | catatcttcc | gggaggcaca | ggctggtata | gaaaaagctt | acaattgat | 300 |
| agagatctgg | caggcaaacg | cattgcgatt | aattttgatg | gcgtctatat | gaatgcaaca | 360 |
| gtctggttta | tggcgttaa | actgggcaca | catccgtatg | ctattcacc | gttttcattt | 420 |
| gatctgacag | gcaatgcaaa | atttggcgga | gaaacacaca | ttgtcgtcaa | agttgaaaat | 480 |
| agactgccgt | catcaagatg | gtattcaggc | agcggcattt | atagagatgt | tacactgaca | 540 |
| gttacagatg | gcgttcatgt | tggcaataat | ggcgtcgcaa | ttaaacacc | gtcactggca | 600 |
| acacaaaatg | gcggagatgt | cacaatgaac | ctgacaacaa | aagtcgcgaa | tgatacagaa | 660 |

```
gcagcagcga acattacact gaaacagaca gtttttccga aaggcggaaa aacggatgca      720
gcaattggca cagttacaac agcatcaaaa tcaattgcag caggcgcatc agcagatgtt      780
acaagcacaa ttacagcagc aagcccgaaa ctgtggtcaa ttaaaaaccc gaacctgtat      840
acagttagaa cagaagttct gaacggaggc aaagttctgg atacatatga tacagaatat      900
ggctttcgct ggacaggctt tgatgcaaca tcaggctttt cactgaatgg cgaaaaagtc      960
aaactgaaag gcgttagcat gcatcatgat caaggctcac ttggcgcagt tgcaaataga     1020
cgcgcaattg aaagacaagt cgaaatcctg caaaaaatgg gcgtcaatag cattcgcaca     1080
acacataatc cggcagcaaa agcactgatt gatgtctgca atgaaaaagg cgttctggtt     1140
gtcgaagaag tctttgatat gtggaaccgc agcaaaaatg gcaacacgga agattatggc     1200
aaatggtttg gccaagcaat tgcaggcgat aatgcagttc tgggaggcga taaagatgaa     1260
acatgggcga aatttgatct tacatcaaca attaaccgcg atagaaatgc accgtcagtt     1320
attatgtggt cactgggcaa tgaaatgatg gaaggcattt caggctcagt ttcaggcttt     1380
ccggcaacat cagcaaaact ggttgcatgg acaaaagcag cagattcaac aagaccgatg     1440
acatatggcg ataacaaaat taaagcgaac tggaacgaat caaatacaat gggcgataat     1500
ctgacagcaa atggcggagt tgttggcaca aattattcag atggcgcaaa ctatgataaa     1560
attcgtacaa cacatccgtc atgggcaatt tatggctcag aaacagcatc agcgattaat     1620
agccgtggca tttataatag aacaacaggc ggagcacaat catcagataa acagctgaca     1680
agctatgata attcagcagt tggctgggga gcagttgcat catcagcatg gtatgatgtt     1740
gttcagagag attttgtcgc aggcacatat gtttggacag gatttgatta tctgggcgaa     1800
ccgacaccgt ggaatggcac aggctcaggc gcagttggct catggccgtc accgaaaaat     1860
agctattttg gcatcgttga tacagcaggc tttccgaaag atacatatta tttttatcag     1920
agccagtgga atgatgatgt tcatacactg catattcttc cggcatggaa tgaaaatgtt     1980
gttgcaaaag gctcaggcaa taatgttccg gttgtcgttt atacagatgc agcgaaagtg     2040
aaactgtatt ttacaccgaa aggctcaaca gaaaaaagac tgatcggcga aaaatcattt     2100
acaaaaaaaa caacagcggc aggctataca tatcaagtct atgaaggcag cgataaagat     2160
tcaacagcgc ataaaaacat gtatctgaca tggaatgttc cgtgggcaga aggcacaatt     2220
tcagcggaag cgtatgatga aaataatcgc ctgattccgg aaggcagcac agaaggcaac     2280
gcatcagtta caacaacagg caaagcagca aaactgaaag cagatgcgga tcgcaaaaca     2340
attacagcgg atggcaaaga tctgtcatat attgaagtcg atgtcacaga tgcaaatggc     2400
catattgttc cggatgcagc aaatagagtc acatttgatg ttaaaggcgc aggcaaactg     2460
gttggcgttg ataatggctc atcaccggat catgattcat atcaagcgga taaccgcaaa     2520
gcattttcag gcaaagtcct ggcaattgtt cagtcaacaa agaagcagg cgaaattaca     2580
gttacagcaa aagcagatgg cctgcaatca agcacagtta aaattgcaac aacagcagtt     2640
ccgggaacaa gcacagaaaa aacagtccgc agcttttatt acagccgcaa ctattatgtc     2700
aaaacaggca caaaccgat tctgccgtca gatgttgaag ttcgctattc agatggaaca     2760
agcgatagac aaaacgttac atgggatgca gtttcagatg atcaaattgc aaaagcaggc     2820
tcatttttcag ttgcaggcac agttgcaggc caaaaaatta gcgttcgcgt cacaatgatt     2880
gatgaaattg gcgcactgct gaattattca gcaagcacac cggttggcac accggcagtt     2940
cttccgggat caagaccggc agtcctgccg gatggcacag tcatcagc aaattttgca     3000
gtccattgga caaaaccggc agatacagtc tataatacag caggcacagt caaagtaccg     3060
```

```
ggaacagcaa cagtttttgg caaagaattt aaagtcacag cgacaattag agttcaaaga    3120
agccaagtta caattggctc atcagtttca ggaaatgcac tgagactgac acaaaatatt    3180
ccggcagata aacaatcaga tacactggat gcgattaaag atggctcaac aacagttgat    3240
gcaaatacag gcggaggcgc aaatccgtca gcatggacaa attgggcata ttcaaaagca    3300
ggccataaca cagcggaaat tacatttgaa tatgcgacag aacaacaact gggccagatc    3360
gtcatgtatt tttttcgcga tagcaatgca gttagatttc cggatgctgg caaaacaaaa    3420
attcagatca gcgcagatgg caaaaattgg acagatctgg cagcaacaga aacaattgca    3480
gcgcaagaat caagcgatag agtcaaaccg tatacatatg attttgcacc ggttggcgca    3540
acatttgtta aagtgacagt cacaaacgca gatacaacaa caccgtcagg cgttgtttgc    3600
gcaggcctga cagaaattga actgaaaaca gcgacaagca aatttgtcac aaatacatca    3660
gcagcactgt catcacttac agtcaatggc acaaaagttt cagattcagt tctggcagca    3720
ggctcatata acacaccggc aattatcgca gatgttaaag cggaaggcga aggcaatgca    3780
agcgttacag tccttccggc acatgataat gttattcgcg tcattacaga aagcgaagat    3840
catgtcacac gcaaaacatt tacaatcaac ctgggcacag aacaagaatt tccggctgat    3900
tcagatgaaa gagattatcc ggcagcagat atgacagtca cagttggctc agaacaaaca    3960
tcaggcacag caacgaagg accgaaaaaa tttgcagtcg atggcaacac atcaacatat    4020
tggcatagca attggacacc gacaacagtt aatgatctgt ggatcgcgtt tgaactgcaa    4080
aaaccgacaa aactggatgc actgagatat cttccgcgtc cggcaggctc aaaaaatggc    4140
agcgtcacag aatataaagt tcaggtgtca gatgatggaa caaactggac agatgcaggc    4200
tcaggcacat ggacaacgga ttatggctgg aaactggcgg aatttaatca accggtcaca    4260
acaaaacatg ttagactgaa agcggttcat acatatgcag atagcggcaa cgataaattt    4320
atgagcgcaa gcgaaattag actgagaaaa gcggtcgata caacggatat ttcaggcgca    4380
acagttacag ttccggcaaa actgacagtt gatagagttg atgcagatca tccggcaaca    4440
tttgcaacaa aagatgtcac agttacactg ggagatgcaa cactgagata tggcgttgat    4500
tatctgctgg attatgcagg caatacagca gttggcaaag caacagtgac agttagaggc    4560
attgataaat attcaggcac agtcgcgaaa acatttacaa ttgaactgaa aaatgcaccg    4620
gcaccggaac cgacactgac atcagttagc gtcaaaacaa aaccgagcaa actgacatat    4680
gttgtcggag atgcatttga tccggcaggc ctggttctgc aacatgatag acaagcagat    4740
agacctccgc aaccgctggt tgcgaacaa gcggatgaac gcggactgac atgcggcaca    4800
agatgcgata gagttgaaca actgcgcaaa catgaaaata gagaagcgca tagaacaggc    4860
ctggatcatc tggaatttgt tggcgcagca gatggcgcag ttggagaaca agcaacattt    4920
aaagtccatg tccatgcaga tcagggagat ggcagacatg atgatgcaga tgaacgcgat    4980
attgatccgc atgttccggt cgatcatgca gttggcgaac tggcaagagc agcatgccat    5040
catgttattg gcctgagagt cgatacacat agacttaaag caagcggctt tcaaattccg    5100
gctgatgata tggcagaaat cgatcgcatt acaggctttc atcgttttga acgccatgtc    5160
```

<210> SEQ ID NO 9
<211> LENGTH: 2661
<212> TYPE: DNA
<213> ORGANISM: Bifidobacterium bifidum
<220> FEATURE:
<221> NAME/KEY: source
<222> LOCATION: 1..2661

<223> OTHER INFORMATION: /mol_type="DNA"
/organism="Bifidobacterium bifidum"

<400> SEQUENCE: 9

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt ttcatttgat     420
ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca attgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaaagtcaaa     960
ctgaaaggcg ttagcatgca tcatgatcaa ggctcacttg gcgcagttgc aaatagacgc    1020
gcaattgaaa acaagtcga atcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taagattca    2160
acagcgcata aaaacatgta tctgacatgg aatgttccgt gggcagaagg cacaatttca    2220
```

```
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga aattacagtt    2580
acagcaaaag cagatggcct gcaatcaagc acagttaaaa ttgcaacaac agcagttccg    2640
ggaacaagca cagaaaaaac a                                              2661

<210> SEQ ID NO 10
<211> LENGTH: 2895
<212> TYPE: DNA
<213> ORGANISM: Bifidobacterium bifidum
<220> FEATURE:
<221> NAME/KEY: source
<222> LOCATION: 1..2895
<223> OTHER INFORMATION: /mol_type="DNA"
      /organism="Bifidobacterium bifidum"

<400> SEQUENCE: 10
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt tcatttgat      420 ctgacaggca atgcaaaatt tggcggagaa aacacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg cgcagttgc aaatagacgc    1020 gcaattgaaa gacaagtcga atcctgcaa aaaatgggcg tcaatagcat tcgcacaaca    1080
cataatccgg cagcaaaagc actgattgat gtctgcaatg aaaaggcgt tctggttgtc    1140 gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
```

```
acagcaaatg gcggagttgt tggcacaaat tattcagatg gcgcaaacta tgataaaatt      1560
cgtacaacac atccgtcatg ggcaatttat ggctcagaaa cagcatcagc gattaatagc      1620
cgtggcattt ataatagaac aacaggcgga gcacaatcat cagataaaca gctgacaagc      1680
tatgataatt cagcagttgg ctggggagca gttgcatcat cagcatggta tgatgttgtt      1740
cagagagatt ttgtcgcagg cacatatgtt tggacaggat ttgattatct gggcgaaccg      1800
acaccgtgga atggcacagg ctcaggcgca gttggctcat ggccgtcacc gaaaaatagc      1860
tattttggca tcgttgatac agcaggcttt ccgaaagata catattattt ttatcagagc      1920
cagtggaatg atgatgttca tacactgcat attcttccgg catggaatga aaatgttgtt      1980
gcaaaaggct caggcaataa tgttccggtt gtcgtttata cagatgcagc gaaagtgaaa      2040
ctgtatttta caccgaaagg ctcaacagaa aaaagactga tcggcgaaaa atcatttaca      2100
aaaaaaacaa cagcggcagg ctatacatat caagtctatg aaggcagcga taagattca      2160 acagcgcata aaaacatgta tctgacatgg aatgttccgt gggcagaagg cacaatttca      2220
gcggaagcgt atgatgaaaa taatcgcctg attccggaag gcagcacaga aggcaacgca      2280
tcagttacaa caacaggcaa agcagcaaaa ctgaaagcag atgcggatcg caaaacaatt      2340
acagcggatg gcaaagatct gtcatatatt gaagtcgatg tcacagatgc aaatggccat      2400
attgttccgg atgcagcaaa tagagtcaca tttgatgtta aaggcgcagg caaactggtt      2460
ggcgttgata atggctcatc accgatcat gattcatatc aagcggataa ccgcaaagca      2520
ttttcaggca aagtcctggc aattgttcag tcaacaaaag aagcaggcga attacagtt       2580 acagcaaaag cagatggcct gcaatcaagc acagttaaaa ttgcaacaac agcagttccg      2640
ggaacaagca cagaaaaaac agtccgcagc ttttattaca gccgcaacta ttatgtcaaa      2700
acaggcaaca aaccgattct gccgtcagat gttgaagttc gctattcaga tggaacaagc      2760
gatagacaaa acgttacatg ggatgcagtt tcagatgatc aaattgcaaa agcaggctca      2820
ttttcagttg caggcacagt tgcaggccaa aaaattagcg ttcgcgtcac aatgattgat      2880
gaaattggcg cactg                                                       2895

<210> SEQ ID NO 11
<211> LENGTH: 3114
<212> TYPE: DNA
<213> ORGANISM: Bifidobacterium bifidum
<220> FEATURE:
<221> NAME/KEY: source
<222> LOCATION: 1..3114
<223> OTHER INFORMATION: /mol_type="DNA"
      /organism="Bifidobacterium bifidum"

<400> SEQUENCE: 11
gttgaagatg caacaagaag cgatagcaca acacaaatgt catcaacacc ggaagttgtt       60
tattcatcag cggtcgatag caaacaaaat cgcacaagcg attttgatgc gaactggaaa      120
tttatgctgt cagatagcgt tcaagcacaa gatccggcat ttgatgattc agcatggcaa      180
caagttgatc tgccgcatga ttatagcatc acacagaaat atagccaaag caatgaagca      240
gaatcagcat atcttccggg aggcacaggc tggtatagaa aaagctttac aattgataga      300
gatctggcag gcaaacgcat tgcgattaat tttgatggcg tctatatgaa tgcaacagtc      360
tggtttaatg gcgttaaact gggcacacat ccgtatggct attcaccgtt tcatttgat       420 ctgacaggca atgcaaaatt tggcggagaa aacacaattg tcgtcaaagt tgaaaataga      480
ctgccgtcat caagatggta ttcaggcagc ggcatttata gagatgttac actgacagtt      540
```

```
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaacccgaa cctgtataca     840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa gacaagtcga atcctgcaa aaaatgggcg tcaatagcat tcgcacaaca    1080
cataatccgg cagcaaaagc actgattgat gtctgcaatg aaaaggcgt tctggttgtc    1140
gaagaagtct ttgatatgtg gaaccgcagc aaaaatggca cacggaaga ttatggcaaa    1200
tggtttggcc aagcaattgc aggcgataat gcagttctgg gaggcgataa agatgaaaca   1260
tgggcgaaat ttgatcttac atcaacaatt aaccgcgata gaaatgcacc gtcagttatt   1320
atgtggtcac tgggcaatga aatgatggaa ggcatttcag gctcagtttc aggctttccg   1380
gcaacatcag caaaactggt tgcatggaca aaagcagcag attcaacaag accgatgaca   1440
tatggcgata caaaattaa agcgaactgg aacgaatcaa atacaatggg cgataatctg    1500
acagcaaatg gcggagttgt tggcacaaat tattcagatg gcgcaaacta tgataaaatt   1560
cgtacaacac atccgtcatg ggcaatttat ggctcagaaa cagcatcagc gattaatagc   1620
cgtggcattt ataatagaac aacaggcgga gcacaatcat cagataaaca gctgacaagc   1680
tatgataatt cagcagttgg ctggggagca gttgcatcat cagcatggta tgatgttgtt   1740
cagagagatt ttgtcgcagg cacatatgtt tggacaggat tgattatct gggcgaaccg    1800
acaccgtgga atggcacagg ctcaggcgca gttggctcat ggccgtcacc gaaaaatagc   1860
tattttggca tcgttgatac agcaggcttt ccgaaagata catattattt ttatcagagc   1920
cagtggaatg atgatgttca tacactgcat attcttccgg catggaatga aatgttgtt    1980
gcaaaaggct caggcaataa tgttccggtt gtcgtttata cagatgcagc gaaagtgaaa   2040
ctgtatttta caccgaaagg ctcaacagaa aaagactga tcggcgaaaa atcatttaca    2100
aaaaaaacaa cagcggcagg ctatacatat caagtctatg aaggcagcga taagattca    2160
acagcgcata aaaacatgta tctgacatgg aatgttccgt gggcagaagg cacaatttca   2220
gcggaagcgt atgatgaaaa taatcgcctg attccggaag gcagcacaga aggcaacgca   2280
tcagttacaa caacaggcaa agcagcaaaa ctgaaagcag atgcggatcg caaaacaatt   2340
acagcggatg gcaaagatct gtcatatatt gaagtcgatg tcacagatgc aaatggccat   2400
attgttccgg atgcagcaaa tagagtcaca tttgatgtta aaggcgcagg caaactggtt   2460
ggcgttgata atggctcatc accggatcat gattcatatc aagcggataa ccgcaaagca   2520
ttttcaggca aagtcctggc aattgttcag tcaacaaaag aagcaggcga attacagtt   2580
acagcaaaag cagatggcct gcaatcaagc acagttaaaa ttgcaacaac agcagttccg   2640
ggaacaagca cagaaaaaac agtccgcagc ttttattaca gccgcaacta ttatgtcaaa   2700
acaggcaaca aaccgattct gccgtcagat gttgaagttc gctattcaga tggaacaagc   2760
gatagacaaa acgttacatg ggatgcagtt tcagatgatc aaattgcaaa agcaggctca   2820
ttttcagttg caggcacagt tgcaggccaa aaaattagcg ttcgcgtcac aatgattgat   2880
gaaattggcg cactgctgaa ttattcagca agcacaccgg ttggcacacc ggcagttctt   2940
```

-continued

```
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag tttttggcaa agaatttaaa gtcacagcga caattagagt tcaa          3114
```

<210> SEQ ID NO 12
<211> LENGTH: 3426
<212> TYPE: DNA
<213> ORGANISM: Bifidobacterium bifidum
<220> FEATURE:
<221> NAME/KEY: source
<222> LOCATION: 1..3426
<223> OTHER INFORMATION: /mol_type="DNA"
      /organism="Bifidobacterium bifidum"

<400> SEQUENCE: 12

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt ttcatttgat     420
ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca attgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaaagtcaaa     960
ctgaaaggcg ttagcatgca tcatgatcaa ggctcacttg gcgcagttgc aaatagacgc    1020
gcaattgaaa gacaagtcga aatcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tggcaatgaa aatgatgaa ggcatttcag gctcagtttc aggctttccg     1380
gcaacatcag caaaactggt tgcatggaca aaagcagcag attcaacaag accgatgaca    1440
tatggcgata caaaattaa agcgaactgg aacgaatcaa atacaatggg cgataatctg     1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
```

```
acaccgtgga atggcacagg ctcaggcgca gttggctcat ggccgtcacc gaaaaatagc      1860
tattttggca tcgttgatac agcaggcttt ccgaaagata catattattt ttatcagagc      1920
cagtggaatg atgatgttca tacactgcat attcttccgg catggaatga aaatgttgtt      1980
gcaaaaggct caggcaataa tgttccggtt gtcgtttata cagatgcagc gaaagtgaaa      2040
ctgtatttta caccgaaagg ctcaacagaa aaaagactga tcggcgaaaa atcatttaca      2100
aaaaaaacaa cagcggcagg ctatacatat caagtctatg aaggcagcga taagattca      2160
acagcgcata aaacatgta tctgacatgg aatgttccgt gggcagaagg cacaatttca      2220
gcggaagcgt atgatgaaaa taatcgcctg attccggaag cagcacaga aggcaacgca      2280
tcagttacaa aacaggcaa agcagcaaaa ctgaaagcag atgcggatcg caaaacaatt      2340
acagcggatg caaagatct gtcatatatt gaagtcgatg tcacagatgc aaatggccat      2400
attgttccgg atgcagcaaa tagagtcaca tttgatgtta aaggcgcagg caaactggtt      2460
ggcgttgata tggctcatc accggatcat gattcatatc aagcggataa ccgcaaagca      2520
ttttcaggca aagtcctggc aattgttcag tcaacaaaag aagcaggcga attacagtt      2580
acagcaaaag cagatggcct gcaatcaagc acagttaaaa ttgcaacaac agcagttccg      2640
ggaacaagca cagaaaaaac agtccgcagc ttttattaca gccgcaacta ttatgtcaaa      2700
acaggcaaca aaccgattct gccgtcagat gttgaagttc gctattcaga tggaacaagc      2760
gatagacaaa acgttacatg ggatgcagtt tcagatgatc aaattgcaaa agcaggctca      2820
ttttcagttg caggcacagt tgcaggccaa aaaattagcg ttcgcgtcac aatgattgat      2880
gaaattggcg cactgctgaa ttattcagca agcacaccgg ttggcacacc ggcagttctt      2940
ccgggatcaa gaccggcagt cctgccggat ggcacagtca catcagcaaa ttttgcagtc      3000
cattggacaa aaccggcaga tacagtctat aatacagcag cacagtcaa agtaccggga      3060
acagcaacag ttttttggcaa agaatttaaa gtcacagcga caattagagt tcaaagaagc      3120
caagttacaa ttggctcatc agtttcagga aatgcactga gactgacaca aaatattccg      3180
gcagataaac aatcagatac actggatgcg attaaagatg gctcaacaac agttgatgca      3240
aatacaggcg gaggcgcaaa tccgtcagca tggacaaatt gggcatattc aaaagcaggc      3300
cataacacag cggaaattac atttgaatat gcgacagaac aacaactggg ccagatcgtc      3360
atgtatttt ttcgcgatag caatgcagtt agatttccgg atgctggcaa aacaaaaatt      3420
cagatc                                                                 3426
```

<210> SEQ ID NO 13
<211> LENGTH: 3633
<212> TYPE: DNA
<213> ORGANISM: Bifidobacterium bifidum
<220> FEATURE:
<221> NAME/KEY: source
<222> LOCATION: 1..3633
<223> OTHER INFORMATION: /mol_type="DNA"
      /organism="Bifidobacterium bifidum"

<400> SEQUENCE: 13

```
gttgaagatg caacaagaag cgatagcaca acacaaatgt catcaacacc ggaagttgtt       60
tattcatcag cggtcgatag caaacaaaat cgcacaagcg attttgatgc gaactggaaa      120
tttatgctgt cagatagcgt tcaagcacaa gatccggcat ttgatgattc agcatggcaa      180
caagttgatc tgccgcatga ttatagcatc acacagaaat atagccaaag caatgaagca      240
gaatcagcat atcttccggg aggcacaggc tggtatagaa aaagctttac aattgataga      300
```

-continued

```
gatctggcag gcaaacgcat tgcgattaat tttgatggcg tctatatgaa tgcaacagtc    360
tggtttaatg gcgttaaact gggcacacat ccgtatggct attcaccgtt ttcatttgat    420
ctgacaggca atgcaaaatt tggcggagaa aacacaattg tcgtcaaagt tgaaaataga    480
ctgccgtcat caagatggta ttcaggcagc ggcatttata gagatgttac actgacagtt    540
acagatggcg ttcatgttgg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag cgcatcagc agatgttaca     780 agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa gacaagtcga atcctgcaa aaaatgggcg tcaatagcat tcgcacaaca    1080
cataatccgg cagcaaaagc actgattgat gtctgcaatg aaaaaggcgt tctggttgtc   1140
gaagaagtct ttgatatgtg gaaccgcagc aaaaatggca cacggaaga ttatggcaaa     1200 tggtttggcc aagcaattgc aggcgataat gcagttctgg gaggcgataa agatgaaaca   1260
tgggcgaaat ttgatcttac atcaacaatt aaccgcgata gaaatgcacc gtcagttatt   1320
atgtggtcac tggcaatga aatgatgaa ggcatttcag gctcagtttc aggctttccg      1380
gcaacatcag caaaactggt tgcatggaca aaagcagcag attcaacaag accgatgaca   1440
tatggcgata acaaaattaa agcgaactgg aacgaatcaa atacaatggg cgataatctg   1500
acagcaaatg gcggagttgt tggcacaaat tattcagatg gcgcaaacta tgataaaatt   1560
cgtacaacac atccgtcatg gcaatttat ggctcagaaa cagcatcagc gattaatagc    1620
cgtggcattt ataatagaac aacaggcgga gcacaatcat cagataaaca gctgacaagc   1680
tatgataatt cagcagttgg ctggggagca gttgcatcat cagcatggta tgatgttgtt   1740
cagagagatt ttgtcgcagg cacatatgtt tggacaggat tgattatct gggcgaaccg     1800 acaccgtgga atggcacagg ctcaggcgca gttggctcat ggccgtcacc gaaaaatagc   1860 tatttttggca tcgttgatac agcaggcttt ccgaaagata catattattt ttatcagagc   1920
cagtggaatg atgatgttca tacactgcat attcttccgg catggaatga aatgttgtt    1980 gcaaaaggct caggcaataa tgttccggtt gtcgtttata cagatgcagc gaaagtgaaa   2040
ctgtatttta caccgaaagg ctcaacagaa aaaagactga tcggcgaaaa atcatttaca   2100
aaaaaaacaa cagcggcagg ctatacatat caagtctatg aaggcagcga taagattca    2160 acagcgcata aaaacatgta tctgacatgg aatgttccgt gggcagaagg cacaatttca   2220
gcggaagcgt atgatgaaaa taatcgcctg attccggaag cagcacaga aggcaacgca    2280 tcagttacaa caacaggcaa agcagcaaaa ctgaaagcag atgcggatcg caaaacaatt   2340
acagcggatg gcaaagatct gtcatatatt gaagtcgatg tcacagatgc aaatggccat   2400
attgttccgg atgcagcaaa tagagtcaca tttgatgtta aggcgcagg caaactggtt    2460 ggcgttgata tggctcatc accggatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg   2640
```

```
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag tttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg aca                                 3633
```

<210> SEQ ID NO 14
<211> LENGTH: 3888
<212> TYPE: DNA
<213> ORGANISM: Bifidobacterium bifidum
<220> FEATURE:
<221> NAME/KEY: source
<222> LOCATION: 1..3888
<223> OTHER INFORMATION: /mol_type="DNA"
      /organism="Bifidobacterium bifidum"

<400> SEQUENCE: 14

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attccccgtt tcatttgat     420 ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggct tcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca ttgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaaagtcaaa     960
```

```
ctgaaaggcg ttagcatgca tcatgatcaa ggctcacttg gcgcagttgc aaatagacgc    1020
gcaattgaaa gacaagtcga aatcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca cacgcgaaga ttatggcaaa    1200
tggtttggcc aagcaattgc aggcgataat gcagttctgg gaggcgataa agatgaaaca    1260
tgggcgaaat tgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg gcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taagattca    2160 acagcgcata aaaacatgta tctgacatgg aatgttccgt gggcagaagg cacaatttca    2220
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
```

```
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg acaagcaaat tgtcacaaa tacatcagca     3660 gcactgtcat cacttacagt caatggcaca aaagtttcag attcagttct ggcagcaggc    3720
tcatataaca caccggcaat tatcgcagat gttaaagcgg aaggcgaagg caatgcaagc    3780
gttacagtcc ttccggcaca tgataatgtt attcgcgtca ttacagaaag cgaagatcat    3840
gtcacacgca aaacatttac aatcaacctg gcacagaac aagaattt                  3888
```

<210> SEQ ID NO 15
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="Synthetic DNA primer"
      /organism="artificial sequences"

<400> SEQUENCE: 15
ggggtaacta gtggaagatg caacaagaag                                     30

<210> SEQ ID NO 16
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
      /note="Synthetic DNA primer"
      /organism="artificial sequences"

<400> SEQUENCE: 16
gcgcttaatt aattatgttt tttctgtgct tgttc                               35

<210> SEQ ID NO 17
<211> LENGTH: 38
<212> TYPE: DNA
<213> ORGANISM: artificial sequences
<220> FEATURE:
<221> NAME/KEY: source
<222> LOCATION: 1..38
<223> OTHER INFORMATION: /mol_type="DNA"
      /note="Synthetic PCR primer"
      /organism="artificial sequences"

<400> SEQUENCE: 17
gcgcttaatt aattacagtg cgccaatttc atcaatca                            38

<210> SEQ ID NO 18
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
      /note="Synthetic PCR primer"
      /organism="artificial sequences"

```
<400> SEQUENCE: 18
gcgcttaatt aattattgaa ctctaattgt cgctg                              35

<210> SEQ ID NO 19
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
      /note="Synthetic PCR primer"
      /organism="artificial sequences"

<400> SEQUENCE: 19
gcgcttaatt aattatgtcg ctgttttcag ttcaat                             36

<210> SEQ ID NO 20
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
      /note="Synthetic PCR primer"
      /organism="artificial sequences"

<400> SEQUENCE: 20
gcgcttaatt aattaaaatt cttgttctgt gccca                              35

<210> SEQ ID NO 21
<211> LENGTH: 38
<212> TYPE: DNA
<213> ORGANISM: artificial sequences
<220> FEATURE:
<221> NAME/KEY: source
<222> LOCATION: 1..38
<223> OTHER INFORMATION: /mol_type="DNA"
      /note="Synthetic PCR primer"
      /organism="artificial sequences"

<400> SEQUENCE: 21
gcgcttaatt aattatctca gtctaatttc gcttgcgc                           38

<210> SEQ ID NO 22
<211> LENGTH: 1720
<212> TYPE: PRT
<213> ORGANISM: Bifidobacterium bifidum
<220> FEATURE:
<221> NAME/KEY: SOURCE
<222> LOCATION: 1..1720
<223> OTHER INFORMATION: /mol_type="protein"
      /organism="Bifidobacterium bifidum"

<400> SEQUENCE: 22

Val Glu Asp Ala Thr Arg Ser Asp Ser Thr Gln Met Ser Ser Thr
 1               5                  10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Ser Val Gln
                35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80
```

```
Glu Ser Ala Tyr Leu Pro Gly Thr Gly Trp Tyr Arg Lys Ser Phe
                85              90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495
```

```
Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
            610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
            690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Thr Gly Lys Ala
            755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
```

-continued

```
            915                 920                 925
Ala Val Ser Asp Asp Gln Ile Ala Lys Ala Gly Ser Phe Ser Val Ala
            930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Pro Val Gly Thr
            965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr Val
            1010                1015                1020

Phe Gly Lys Glu Phe Lys Val Thr Ala Thr Ile Arg Val Gln Arg Ser
1025                1030                1035                1040

Gln Val Thr Ile Gly Ser Ser Val Ser Gly Asn Ala Leu Arg Leu Thr
            1045                1050                1055

Gln Asn Ile Pro Ala Asp Lys Gln Ser Asp Thr Leu Asp Ala Ile Lys
            1060                1065                1070

Asp Gly Ser Thr Thr Val Asp Ala Asn Thr Gly Gly Gly Ala Asn Pro
            1075                1080                1085

Ser Ala Trp Thr Asn Trp Ala Tyr Ser Lys Ala Gly His Asn Thr Ala
            1090                1095                1100

Glu Ile Thr Phe Glu Tyr Ala Thr Glu Gln Gln Leu Gly Gln Ile Val
1105                1110                1115                1120

Met Tyr Phe Phe Arg Asp Ser Asn Ala Val Arg Phe Pro Asp Ala Gly
            1125                1130                1135

Lys Thr Lys Ile Gln Ile Ser Ala Asp Gly Lys Asn Trp Thr Asp Leu
            1140                1145                1150

Ala Ala Thr Glu Thr Ile Ala Ala Gln Glu Ser Ser Asp Arg Val Lys
            1155                1160                1165

Pro Tyr Thr Tyr Asp Phe Ala Pro Val Gly Ala Thr Phe Val Lys Val
            1170                1175                1180

Thr Val Thr Asn Ala Asp Thr Thr Pro Ser Gly Val Val Cys Ala
1185                1190                1195                1200

Gly Leu Thr Glu Ile Glu Leu Lys Thr Ala Thr Ser Lys Phe Val Thr
            1205                1210                1215

Asn Thr Ser Ala Ala Leu Ser Ser Leu Thr Val Asn Gly Thr Lys Val
            1220                1225                1230

Ser Asp Ser Val Leu Ala Ala Gly Ser Tyr Asn Thr Pro Ala Ile Ile
            1235                1240                1245

Ala Asp Val Lys Ala Glu Gly Glu Gly Asn Ala Ser Val Thr Val Leu
            1250                1255                1260

Pro Ala His Asp Asn Val Ile Arg Val Ile Thr Glu Ser Glu Asp His
1265                1270                1275                1280

Val Thr Arg Lys Thr Phe Thr Ile Asn Leu Gly Thr Glu Gln Glu Phe
            1285                1290                1295

Pro Ala Asp Ser Asp Glu Arg Asp Tyr Pro Ala Ala Asp Met Thr Val
            1300                1305                1310

Thr Val Gly Ser Glu Gln Thr Ser Gly Thr Ala Thr Glu Gly Pro Lys
            1315                1320                1325

Lys Phe Ala Val Asp Gly Asn Ser Thr Tyr Trp His Ser Asn Trp
            1330                1335                1340
```

Thr Pro Thr Thr Val Asn Asp Leu Trp Ile Ala Phe Glu Leu Gln Lys
1345                1350                1355                1360

Pro Thr Lys Leu Asp Ala Leu Arg Tyr Leu Pro Arg Pro Ala Gly Ser
            1365                1370                1375

Lys Asn Gly Ser Val Thr Glu Tyr Lys Val Gln Val Ser Asp Asp Gly
        1380                1385                1390

Thr Asn Trp Thr Asp Ala Gly Ser Gly Thr Trp Thr Thr Asp Tyr Gly
    1395                1400                1405

Trp Lys Leu Ala Glu Phe Asn Gln Pro Val Thr Thr Lys His Val Arg
1410                1415                1420

Leu Lys Ala Val His Thr Tyr Ala Asp Ser Gly Asn Asp Lys Phe Met
1425                1430                1435                1440

Ser Ala Ser Glu Ile Arg Leu Arg Lys Ala Val Asp Thr Thr Asp Ile
            1445                1450                1455

Ser Gly Ala Thr Val Thr Val Pro Ala Lys Leu Thr Val Asp Arg Val
            1460                1465                1470

Asp Ala Asp His Pro Ala Thr Phe Ala Thr Lys Asp Val Thr Val Thr
            1475                1480                1485

Leu Gly Asp Ala Thr Leu Arg Tyr Gly Val Asp Tyr Leu Leu Asp Tyr
            1490                1495                1500

Ala Gly Asn Thr Ala Val Gly Lys Ala Thr Val Thr Val Arg Gly Ile
1505                1510                1515                1520

Asp Lys Tyr Ser Gly Thr Val Ala Lys Thr Phe Thr Ile Glu Leu Lys
            1525                1530                1535

Asn Ala Pro Ala Pro Glu Pro Thr Leu Thr Ser Val Ser Val Lys Thr
            1540                1545                1550

Lys Pro Ser Lys Leu Thr Tyr Val Val Gly Asp Ala Phe Asp Pro Ala
            1555                1560                1565

Gly Leu Val Leu Gln His Asp Arg Gln Ala Asp Arg Pro Pro Gln Pro
1570                1575                1580

Leu Val Gly Glu Gln Ala Asp Glu Arg Gly Leu Thr Cys Gly Thr Arg
1585                1590                1595                1600

Cys Asp Arg Val Glu Gln Leu Arg Lys His Glu Asn Arg Glu Ala His
            1605                1610                1615

Arg Thr Gly Leu Asp His Leu Glu Phe Val Gly Ala Ala Asp Gly Ala
            1620                1625                1630

Val Gly Glu Gln Ala Thr Phe Lys Val His Val His Ala Asp Gln Gly
            1635                1640                1645

Asp Gly Arg His Asp Asp Ala Asp Glu Arg Asp Ile Asp Pro His Val
            1650                1655                1660

Pro Val Asp His Ala Val Gly Glu Leu Ala Arg Ala Ala Cys His His
1665                1670                1675                1680

Val Ile Gly Leu Arg Val Asp Thr His Arg Leu Lys Ala Ser Gly Phe
            1685                1690                1695

Gln Ile Pro Ala Asp Asp Met Ala Glu Ile Asp Arg Ile Thr Gly Phe
            1700                1705                1710

His Arg Phe Glu Arg His Val Gly
        1715                1720

<210> SEQ ID NO 23
<211> LENGTH: 30
<212> TYPE: PRT
<213> ORGANISM: Bifidobacterium bifidum
<220> FEATURE:

```
-continued

<221> NAME/KEY: SOURCE
<222> LOCATION: 1..30
<223> OTHER INFORMATION: /mol_type="protein"
      /note="Signal sequence of extracellular lactase from Bifidobacter
      ium bifidum DSM20215"
      /organism="Bifidobacterium bifidum"

<400> SEQUENCE: 23

Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala
                20                  25                  30
```

POLYPEPTIDES HAVING TRANSGALACTOSYLATING ACTIVITY

SEQUENCE LISTING

The sequence listing submitted via EFS, in compliance with 37 C.F.R. § 1.52(e), is incorporated herein by reference. The sequence listing text file submitted via EFS contains the file "40269-US-PCT_SequeneListing.txt" created on Mar. 26, 2015, 106 KB (109,335 bytes).

FIELD OF THE INVENTION

The present invention relates to polypeptides, specifically polypeptides having transgalactosylating activity and nucleic acids encoding these, and their uses in e.g. dairy product.

BACKGROUND OF THE INVENTION

Galactooligosaccharides (GOS) are carbohydrates which are nondigestable in humans and animals comprising two or more galactose molecules, typically up to nine, linked by glycosidic bonds. GOS's may also include one or more glucose molecules. One of the beneficial effects of GOS's is their ability of acting as prebiotic compounds by selectively stimulating the proliferation of beneficial colonic microorganisms such as bacteria to give physiological benefits to the consumer. The established health effects have resulted in a growing interest in GOSs as food ingredients for various types of food.

The enzyme β-galactosidase (EC 3.2.1.23) usually hydrolyses lactose to the monosaccharides D-glucose and D-galactose. In the normal enzyme reaction of β-galactosidases, the enzyme hydrolyses lactose and transiently binds the galactose monosaccharide in a galactose-enzyme complex that transfers galactose to the hydroxyl group of water, resulting in the liberation of D-galactose and D-glucose. However, at high lactose concentrations some β-galactosidases are able to transfer galactose to the hydroxyl groups of D-galactose or D-glucose in a process called transgalactosylation whereby galacto-oligosaccharides are produced. Also at high lactose concentrations some β-galactosidases are able to transfer galactose to the hydroxyl groups of lactose or higher order oligosaccharides.

The genus *Bifidobacterium* is one of the most commonly used types of bacteria cultures in the dairy industry for fermenting a variety of diary products. Ingestion of *Bifidobacterium*-containing products furthermore has a health-promoting effect. This effect is not only achieved by a lowered pH of the intestinal contents but also by the ability of *Bifidobacterium* to repopulate the intestinal flora in individuals who have had their intestinal flora disturbed by for example intake of antibiotics. *Bifidobacterium* furthermore has the potential of outcompeting potential harmful intestinal micro-organisms.

Galacto-oligosaccharides are known to enhance the growth of *Bifidobacterium*. This effect is likely achieved through the unique ability of *Bifidobacterium* to exploit galacto-oligosaccharides as a carbon source. Dietary supplement of galacto-oligosaccharides is furthermore thought to have a number of long-term disease protecting effects. For example, galacto-oligosaccharide intake has been shown to be highly protective against development of colorectal cancer in rats. There is therefore a great interest in developing cheap and efficient methods for producing galacto-oligosaccharides for use in the industry for improving dietary supplements and dairy products.

An extracellular lactase from *Bifidobacterium bifidum* DSM20215 truncated with approximately 580 amino acids (BIF3-d3) has been described as a transgalactosylating enzyme in a solution containing lactose solubilised in water (Jørgensen et al. (2001), Appl. Microbiol. Biotechnol., 57: 647-652). WO 01/90317 also describes a truncation variant (OLGA347) as being a transgalactosylating enzyme and in WO 2012/010597 OLGA347 was shown to transfer a galactose moiety to D-fucose, N-acetyl-galactosamine and xylose.

In WO 2009/071539 a differently truncated fragment compared to BIF3-d3 is described as resulting in efficient hydrolysis and very low production of GOS when tested in milk.

The *Bifidobacterium bifidum* lactase enzymes described above have the drawback of either requiring high lactose concentrations such as above 10% (w/w) in order to produce GOS, or a high surplus of another acceptor molecule to generate heterooligosaccharides. Furthermore, a molecule has been described that predominately having beta-galactosylase (hydrolase) activity.

There is still a need to develop enzymes that are efficient at producing GOS in applications with low lactose substrate levels such as in milk.

SUMMARY OF THE INVENTION

It is an object of embodiments of the invention to provide a polypeptide which has a useful ratio of transgalactosylation to hydrolysis activity and thus are efficient producers of GOS when incubated with lactose even at low lactose levels such as in a milk-based product. It is a further object of embodiments of the invention to provide a method for production of galacto-oligosaccharides (GOS) in situ in dairy products. It is a further object of embodiments of the invention to provide a method for developing a cheaper and more efficient method for production of galacto-oligosaccharides (GOS) for use in the industry. It is further object of embodiments of the invention to provide polypeptides which are stable against further truncation such as by proteolytic degradation when produced in a suitable organism such as *Bacillus subtilis* e.g. *Bacillus subtilis* strain BG3594. It is yet a further object of embodiments of the invention to provide polypeptides which are stable against further truncation during storage after final formulation.

The present inventors have surprisingly found that the polypeptides disclosed herein are efficient producers of galacto-oligosaccharides for example in situ when incubated in a lactose containing composition such as milk, wherein they have an efficient conversion of lactose into GOS resulting in a lower amount of free lactose. The presence of galacto-oligosaccharides in diary products or other comestible products has the advantage of enhancing the growth of beneficial microbial strains (probiotics) such as the health-promoting *Bifidobacterium* sp. in the product itself and/or in the human or animal that consumes the product.

In one aspect, disclosed herein is a polypeptide having transgalactosylating activity, which comprises an amino acid sequence having at least 90% sequence identity with SEQ ID NO: 1, and wherein said polypeptide, when being an expression product in a *Bacillus subtilis* strain BG3594 of a nucleic acid sequence, which encodes said polypeptide, is the only polypeptide expression product of said nucleic acid sequence that exhibits transgalactosylating activity.

In one aspect, disclosed herein is a polypeptide having transgalactosylating activity selected from the group consisting of:
a. a polypeptide comprising an amino acid sequence having at least 90% sequence identity with SEQ ID NO: 1, wherein said polypeptide consists of at most 980 amino acid residues,
b. a polypeptide comprising an amino acid sequence having at least 97% sequence identity with SEQ ID NO: 2, wherein said polypeptide consists of at most 975 amino acid residues,
c. a polypeptide comprising an amino acid sequence having at least 96.5% sequence identity with SEQ ID NO: 3, wherein said polypeptide consists of at most 1300 amino acid residues,
d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
f. a polypeptide comprising a deletion, insertion and/or conservative substitution of one or more amino acid residues of SEQ ID NO: 1, 2, 3, 4 or 5.

In another aspect disclosed herein is a polypeptide having transgalactosylating activity selected from the group consisting of:
a. a polypeptide comprising an amino acid sequence having at least 96.5% sequence identity with SEQ ID NO: 3, wherein said polypeptide consists of at most 1300 amino acid residues,
b. a polypeptide comprising an amino acid sequence having at least 90% sequence identity with SEQ ID NO: 1, wherein said polypeptide consists of at most 980 amino acid residues,
c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
e. a polypeptide comprising a deletion, insertion and/or conservative substitution of one or more amino acid residues of SEQ ID NO: 1, 2, 3, 4 or 5.

In one aspect, disclosed herein is polypeptide which is a C-terminal truncated fragment of SEQ ID NO:22 having transgalactosylating activity and which are stable against further truncation such as by proteolytic degradation when produced in a suitable organism such as *Bacillus subtilis* e.g. *Bacillus subtilis* strain BG3594 and/or which are stable against further truncation during storage after final formulation.

In one aspect, disclosed herein is a polypeptide comprising an amino acid sequence having at least 90% sequence identity with SEQ ID NO: 1, wherein said polypeptide consists of at most 980 amino acid residues.

In one aspect, disclosed herein is a polypeptide comprising an amino acid sequence having at least 97% sequence identity with SEQ ID NO: 2, wherein said polypeptide consists of at most 975 amino acid residues, is provided.

In one aspect, disclosed herein is a polypeptide comprising an amino acid sequence having at least 96.5% sequence identity with SEQ ID NO: 3, wherein said polypeptide consists of at most 1300 amino acid residues.

In one aspect, disclosed herein is a nucleic acid capable of encoding a polypeptide as described herein.

In one aspect, disclosed herein is an expression vector and/or a plasmid comprising a nucleic as described herein, or capable of expressing a polypeptide as described herein.

In one aspect, disclosed herein is a cell capable of expressing a polypeptide as described herein.

In one aspect, disclosed herein is a method of expressing a polypeptide, the method comprising obtaining a cell as described herein and expressing the polypeptide from the cell, and optionally purifying the polypeptide.

In one aspect, disclosed herein is a composition comprising a polypeptide as described herein, preferably a food composition, more preferably a dairy product.

In one aspect, disclosed herein is a method for producing a food product such as a dairy product by treating a milk-based substrate comprising lactose with a polypeptide as described herein.

In one aspect, disclosed herein is a galacto-oligosaccharide or composition thereof obtained by treating a substrate comprising lactose with a polypeptide as described herein.

LEGENDS TO THE FIGURE

Figure 3:
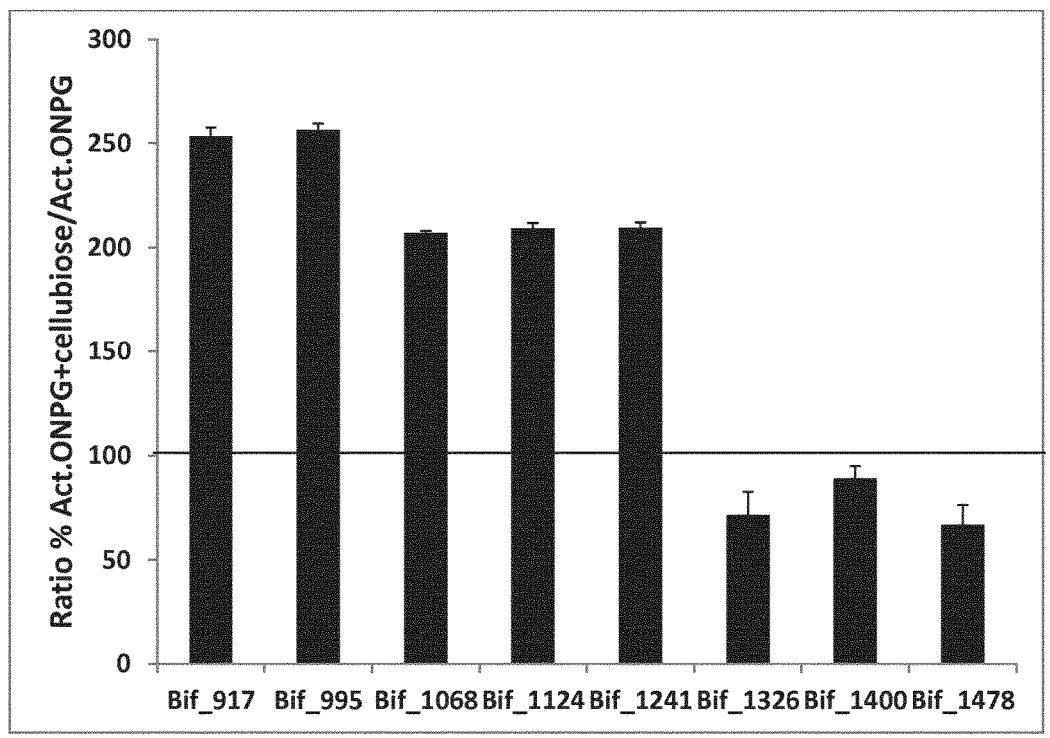

FIG. 3 shows the ratio of transgalactosylation activity. Ratio is calculated as ratio between Abs420 with acceptor present divided by Abs420 without acceptor present times 100. Variants at or below index 100 are purely hydrolytic variants, whereas the level above reflects relative transgalactosylating activity.

Figure 4:
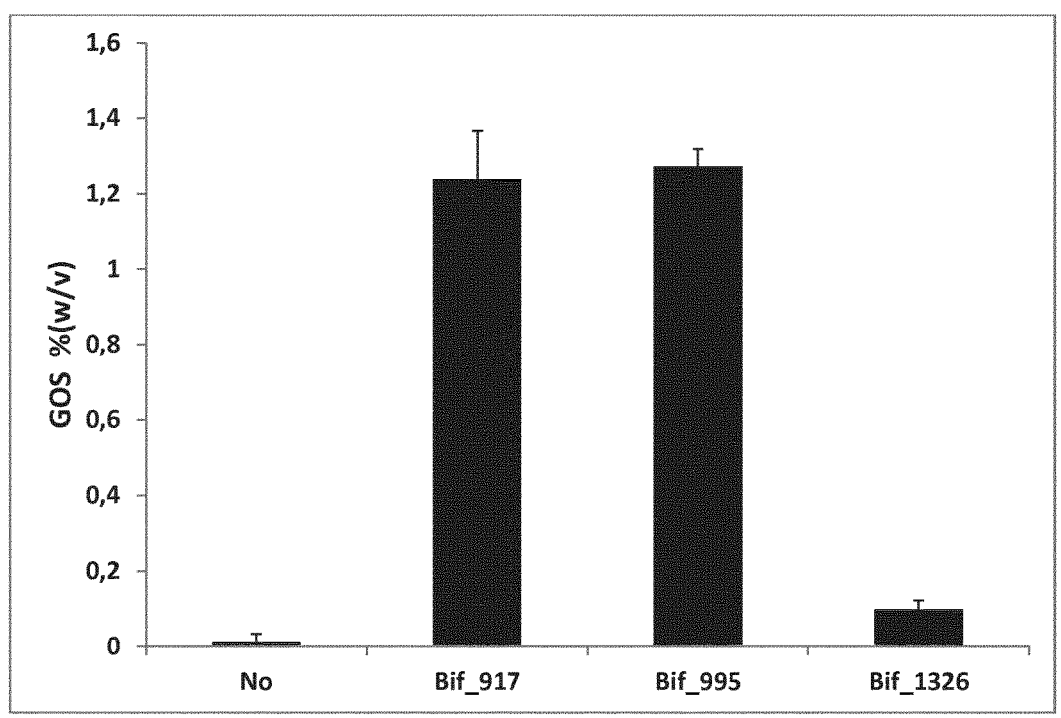

FIG. 4 shows Galacto-oligosaccharides (GOS) generating efficacy of selected variants in a yoghurt matrix at 30° C. for 3 hours. In this example GOS is the accumulative amount oligosaccharides at and above DP3.

Figure 5:
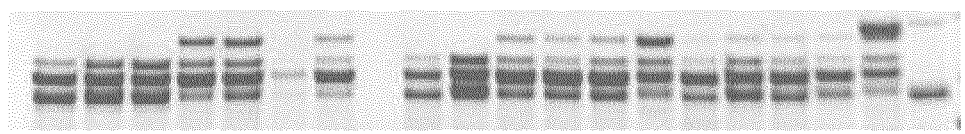
Figure 5:
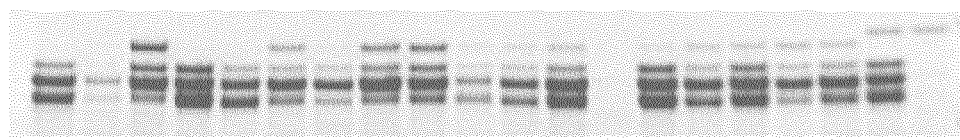
Figure 5:
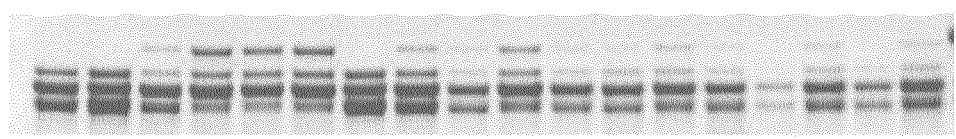
Figure 5:
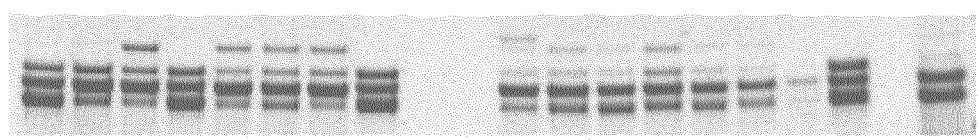
Figure 5:
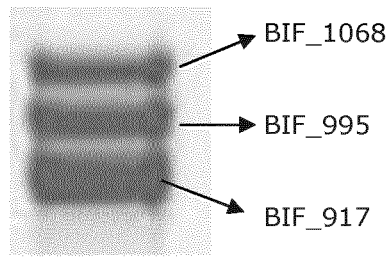

FIG. 5 shows SDS-PAGE gel showing the different variants from table 2 expressed and the degradation fragments detected. Lower panel shows magnification and identification of degradation bands.

SEQUENCE LISTING

SEQ ID NO: 1 (also named (BIF_917) herein) is a 887 amino acid truncated fragment of SEQ ID NO: 22.

SEQ ID NO: 2 (also named (BIF_995) herein) is a 965 amino acid truncated fragment of SEQ ID NO: 22.

SEQ ID NO: 3 (also named (BIF_1068) herein) is a 1038 amino acid truncated fragment of SEQ ID NO: 22.

SEQ ID NO: 4 (also named (BIF_1172) herein) is a 1142 amino acid truncated fragment of SEQ ID NO: 22.

SEQ ID NO: 5 (also named (BIF_1241) herein) is a 1211 amino acid truncated fragment of SEQ ID NO: 22.

SEQ ID NO: 6 (also named (BIF_1326) herein) is a 1296 amino acid truncated fragment of SEQ ID NO: 22.

SEQ ID NO: 7 is *Bifidobacterium bifidum* glycoside hydrolase catalytic core

SEQ ID NO: 8 is a nucleotide sequence encoding an extracellular lactase from *Bifidobacterium bifidum* DSM20215

SEQ ID NO: 9 is nucleotide sequence encoding BIF_917

SEQ ID NO: 10 is nucleotide sequence encoding BIF_995

SEQ ID NO: 11 is nucleotide sequence encoding BIF_1068

SEQ ID NO: 12 is nucleotide sequence encoding BIF_1172

SEQ ID NO: 13 is nucleotide sequence encoding BIF_1241

SEQ ID NO: 14 is nucleotide sequence encoding BIF_1326

SEQ ID NO: 15 is forward primer for generation of above BIF variants

SEQ ID NO: 16 is reverse primer for BIF917

SEQ ID NO: 17 is reverse primer for BIF995

SEQ ID NO: 18 is reverse primer for BIF1068

SEQ ID NO: 19 is reverse primer for BIF1241

SEQ ID NO: 20 is reverse primer for BIF1326

SEQ ID NO: 21 is reverse primer for BIF1478

SEQ ID NO: 22 is extracellular lactase from *Bifidobacterium bifidum* DSM20215.

SEQ ID NO: 23 is signal sequence of extracellular lactase from *Bifidobacterium bifidum* DSM20215

DETAILED DISCLOSURE OF THE INVENTION

Definitions

In accordance with this detailed description, the following abbreviations and definitions apply. It should be noted that as used herein, the singular forms "a," "an," and "the" include plural referents unless the context clearly dictates otherwise. Thus, for example, reference to "a polypeptide" includes a plurality of such polypeptides, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

"Transgalactosylase" means an enzyme that, among other things, is able to transfer galactose to the hydroxyl groups of D-galactose or D-glucose whereby galacto-oligosaccharides are produced. In one aspect, a transgalactosylase is identified by reaction of the enzyme on lactose in which the amount of galactose generated is less than the amount of glucose generated at any given time.

In the present context, the term "transgalactosylating activity" means the transfer of a galactose moiety to a molecule other than water. The activity can be measured as [glucose]-[galactose] generated at any given time during reaction or by direct quantification of the GOS generated at any given time during the reaction. This measurement may be performed in several ways such as by a HPLC method as shown in the examples. When comparing measurements of transgalactosylating activity, they have been performed at a given initial lactose concentration, such as e.g. 3, 4, 5, 6, 7, 8, 9 or 10% (w/w).

In the present context, the term "β-galactosidase activity" means the ability of an enzyme to hydrolyse β-galactosides such as for example lactose into monosaccharides, glucose and galactose.

In the context of calculating transgalactosylating activity:β-galactosidase activity, the β-galactosidase activity is measured as [galactose] generated at any given time during reaction. This measurement may be performed in several ways such as by a HPLC method as shown in the examples.

In the present context, the term "ratio of transgalactosylation activity" using ortho-nitrophenol-β-D-galactopyranoside (ONPG) was calculated as follows: Ratio is calculated as ratio between Abs420 with acceptor present divided by Abs420 without acceptor present times 100. Variant at or below index 100 are purely hydrolytic variants, whereas the level above depicts relative transgalactosylating activity.

Ratio of transgalactosylation activity=$(Abs420^{+Cellobiose}/Abs420^{-Cellobiose})*100\%$, where $Abs420^{+Cellobiose}$ is the absorbance read at 420 nm using the described method 3 below including cellobiose in the reaction and $Abs420^{-Cellobiose}$ is the absorbance read at 420 nm using the described method 3 below but without cellobiose in the reaction. The equation above is only valid for dilutions where the absorbance is between 0.5 and 1.0.

In one aspect, the activity is measured after 15 min. reaction, 30 min. reaction, 60 min. reaction, 90 min. reaction, 120 min. reaction or 180 min. reaction. Thus in one aspect, as an example the relative transgalactosylation activity is measured 15 minutes after addition of enzyme, such as 30 minutes after addition of enzyme, such as 60 minutes after addition of enzyme, such as 90 minutes after addition of enzyme, such as 120 minutes after addition of enzyme or such as 180 minutes after addition of enzyme.

In the present context, the term "ratio of transgalactosylating activity:β-galactosidase activity" means ([Glucose]-[Galactose]/[Galactose]).

In the present context, the term [Glucose] means the glucose concentration in % by weight as measured by HPLC.

In the present context, the term [Galactose] means the galactose concentration in % by weight as measured by HPLC.

In the present context, the term "lactose has been transgalactosylated" means that a galactose molecule has been covalently linked to the lactose molecule such as for example covalently linked to any of the free hydroxyl groups in the lactose molecule or as generated by internal transgalatosylation for example forming allolactose.

In the present context, the evaluation of performance of polypeptides disclosed herein in galactooligosaccharide (GOS) production were tested in a "milk-based assay" (yogurt application mimic). Batch experiments with a volume of 100 µl were performed in 96 well MTP plates using a yogurt mix, consisting of 98.60% (w/v) fresh pasteurized low-fat milk (Arla Mini-mælk) and 1.4% (w/v) Nutrilac YQ-5075 whey ingredient (Arla). To completely hydrate Nutrilac YQ-5075 the mixture was left with agitation for 20 h and afterwards added 20 mM NaPhosphate pH 6.5 to ensure a pH of 6.5. This yogurt-base was either used plain or with various supplements such as additional lactose, fucose, maltose, xylose or salts. 90 µl of the yogurt was mixed with 10 µl purified enzyme or crude ferment, sealed with tape and incubated at 43° C. for 3 hours. The reaction was stopped by 100 µl 10 Na2CO3. Samples were stored at −20° C. Quantification of galactooligosaccharides (GOS), lactose, glucose and galactose were performed by HPLC. Analysis of samples was carried out on a Dionex ICS 3000. IC parameters were as follows: Mobile phase: 150 mM NaOH, Flow: Isochratic, 0.25 ml/min, Column: Carbopac PA1, Column temperature: RT, Injection volume: 10 µL, Detector: PAD, Integration: Manual, Sample preparation: 100 times dilution in Milli-Q water (0.1 ml sample+9.9 ml water) and filtration through 0.45 im syringe filters, Quantification: Peak areas in percent of peak area of the standard. A GOS syrup (Vivanal GOS, Friesland Campina) was used as standard for GOS quantification. Results of such an evaluation is shown in FIG. 4, and further described in example 2.

In the present context, the term "which polypeptide is freeze-dried" means that the polypeptide has been obtained by freeze-drying a liquid of the polypeptide at an appropriate pressure and for an appropriate period removing the water.

In the present context, the term "which polypeptide is in solution" relates to a polypeptide which is soluble in a solvent without precipitating out of solution. A solvent for this purpose includes any millieu in which the polypeptide may occur, such as an aqueous buffer or salt solution, a fermentation broth, or the cytoplasm of an expression host.

In the present context, the term "stabilizer" means any stabilizer for stabilizing the polypeptide e.g., a polyol such as, e.g., glycerol or propylene glycol, a sugar or a sugar alcohol, lactic acid, boric acid, or a boric acid derivative (e.g., an aromatic borate ester). In one aspect, the stabilizer is glycerol.

In the present context, the term "carbohydrate substrate" means an organic compound with the general formula $C_m(H_2O)_n$, that is, consisting only of carbon, hydrogen and oxygen, the last two in the 2:1 atom ratio such as a disaccharide.

In the present context, the term "disaccharide" is two monosaccharide units bound together by a covalent bond known as a glycosidic linkage formed via a dehydration reaction, resulting in the loss of a hydrogen atom from one monosaccharide and a hydroxyl group from the other. The formula of unmodified disaccharides is $C_{12}H_{22}O_{11}$. In one aspect, the disaccharide is lactulose, trehalose, rhamnose, maltose, sucrose, lactose, fucose or cellobiose. In a further aspect, the disaccharide is lactose.

The term "isolated" means that the polypeptide is at least substantially free from at least one other component with which the sequence is naturally associated in nature and as found in nature. In one aspect, "isolated polypeptide" as used herein refers to a polypeptide which is at least 30% pure, at least 40% pure, at least 60% pure, at least 80% pure, at least 90% pure, and at least 95% pure, as determined by SDS-PAGE.

The term "substantially pure polypeptide" means herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides disclosed herein are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods. Herein, the term "substantially pure polypeptide" is synonymous with the terms "isolated polypeptide" and "polypeptide in isolated form."

The term "purified" or "pure" means that a given component is present at a high level state—e.g. at least about 51% pure, such as at least 51% pure, or at least about 75% pure such as at least 75% pure, or at least about 80% pure such as at least 80% pure, or at least about 90% pure such as at least 90% pure, or at least about 95% pure such as at least 95% pure, or at least about 98% pure such as at least 98% pure. The component is desirably the predominant active component present in a composition.

The term "microorganism" in relation to the present invention includes any "microorganism" that could comprise a nucleotide sequence according to the present invention or a nucleotide sequence encoding for a polypeptide having the specific properties as defined herein and/or products obtained therefrom. In the present context, "microorganism" may include any bacterium or fungus being able to ferment a milk substrate.

The term "host cell"—in relation to the present invention includes any cell that comprises either a nucleotide sequence encoding a polypeptide having the specific properties as defined herein or an expression vector as described above and which is used in the production of a polypeptide having the specific properties as defined herein. In one aspect, the production is recombinant production.

The term "milk", in the context of the present invention, is to be understood as the lacteal secretion obtained from any mammal, such as cows, sheep, goats, buffaloes or camels. In the present context, the term "milk-based substrate" means any raw and/or processed milk material or a material derived from milk constituents. Useful milk-based substrates include, but are not limited to solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream. Preferably, the milk-based substrate is milk or an aqueous solution of skim milk powder. The milk-based substrate may be more concentrated than raw milk. In one embodiment, the milk-based substrate has a ratio of protein to lactose of at least 0.2, preferably at least 0.3, at least 0.4, at least 0.5, at least 0.6 or, most preferably, at least 0.7.

The milk-based substrate may be homogenized and/or pasteurized according to methods known in the art.

"Homogenizing" as used herein means intensive mixing to obtain a soluble suspension or emulsion. It may be performed so as to break up the milk fat into smaller sizes so that it no longer separates from the milk. This may be accomplished by forcing the milk at high pressure through small orifices.

"Pasteurizing" as used herein means reducing or eliminating the presence of live organisms, such as microorganisms, in the milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow. A "food product" or "food composition" in the context of the present invention may be any comestible food or feed product suitable for consumption by an animal or human.

A "dairy product" in the context of the present invention may be any food product wherein one of the major constituents is milk-based. Preferable, the major constituent is milk-based. More preferably, the major constituent is a milk-based substrate which has been treated with an enzyme having transgalactosylating activity.

In the present context, "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

A "fermented dairy product" in present context is to be understood as any dairy product wherein any type of fermentation forms part of the production process. Examples of fermented dairy products are products like yoghurt, buttermilk, creme fraiche, quark and fromage frais. Another example of a fermented dairy product is cheese. A fermented dairy product may be produced by any method known in the art.

The term "fermentation" means the conversion of carbohydrates into alcohols or acids through the action of a microorganism such as a starter culture. In one aspect, fermentation comprises conversion of lactose to lactic acid.

In the present context, "microorganism" may include any bacterium or fungus being able to ferment a milk substrate.

In the present context the term "Pfam domains" means regions within a protein sequence that are identified as either Pfam-A or Pfam-B based on multiple sequence alignments and the presence of Hidden Markov Motifs ("*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222.). As examples of Pfam domains mention may be made of Glyco_hydro2N (PF02837), Glyco_hydro (PF00703), Glyco_hydro 2C (PF02836) and Bacterial Ig-like domain (group 4) (PF07532).

As used herein "a position corresponding to position" means that an alignment as described herein is made between a particular query polypeptide and the reference polypeptide. The position corresponding to a specific position in the reference polypeptide is then identified as the corresponding amino acid in the alignment with the highest sequence identity.

A "variant" or "variants" refers to either polypeptides or nucleic acids. The term "variant" may be used interchangeably with the term "mutant". Variants include insertions, substitutions, transversions, truncations, and/or inversions at one or more locations in the amino acid or nucleotide sequence, respectively. The phrases "variant polypeptide", "polypeptide variant", "polypeptide", "variant" and "variant enzyme" mean a polypeptide/protein that has an amino acid sequence that either has or comprises a selected amino acid sequence of or is modified compared to the selected amino acid sequence, such as SEQ ID NO: 1, 2, 3, 4 or 5.

As used herein, "reference enzymes," "reference sequence," "reference polypeptide" mean enzymes and polypeptides from which any of the variant polypeptides are based, e.g., SEQ ID NO: 1, 2, 3, 4 or 5. A "reference nucleic acid" means a nucleic acid sequence encoding the reference polypeptide.

As used herein, the terms "reference sequence" and "subject sequence" are used interchangeably.

As used herein, "query sequence" means a foreign sequence, which is aligned with a reference sequence in order to see if it falls within the scope of the present invention. Accordingly, such query sequence can for example be a prior art sequence or a third party sequence.

As used herein, the term "sequence" can either be referring to a polypeptide sequence or a nucleic acid sequence, depending of the context.

As used herein, the terms "polypeptide sequence" and "amino acid sequence" are used interchangeably.

The signal sequence of a "variant" may be the same or may differ from the signal sequence of the wild-type a *Bacillus* signal peptide or any signal sequence that will secrete the polypeptide. A variant may be expressed as a fusion protein containing a heterologous polypeptide. For example, the variant can comprise a signal peptide of another protein or a sequence designed to aid identification or purification of the expressed fusion protein, such as a His-Tag sequence.

To describe the various variants that are contemplated to be encompassed by the present disclosure, the following nomenclature will be adopted for ease of reference. Where the substitution includes a number and a letter, e.g., 592P, then this refers to {position according to the numbering system/substituted amino acid}. Accordingly, for example, the substitution of an amino acid to proline in position592 is designated as 592P. Where the substitution includes a letter, a number, and a letter, e.g., D592P, then this refers to {original amino acid/position according to the numbering system/substituted amino acid}.

Accordingly, for example, the substitution of alanine with proline in position 592 is designated as A592P.

Where two or more substitutions are possible at a particular position, this will be designated by contiguous letters, which may optionally be separated by slash marks "/", e.g., G303ED or G303E/D.

Position(s) and substitutions are listed with reference to for example either SEQ ID NO: 1, 2, 3, 4 or 5. For example equivalent positions in another sequence may be found by aligning this sequence with either SEQ ID NO: 1, 2, 3, 4 or 5 to find an alignment with the highest percent identity and thereafter determining which amino acid aligns to correspond with an amino acid of a specific position of either SEQ ID NO: 1, 2, 3, 4 or 5. Such alignment and use of one sequence as a first reference is simply a matter of routine for one of ordinary skill in the art.

As used herein, the term "expression" refers to the process by which a polypeptide is produced based on the nucleic acid sequence of a gene. The process includes both transcription and translation.

As used herein, "polypeptide" is used interchangeably with the terms "amino acid sequence", "enzyme", "peptide" and/or "protein". As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

"Homologue" means an entity having a certain degree of identity or "homology" with the subject amino acid sequences and the subject nucleotide sequences. In one aspect, the subject amino acid sequence is SEQ ID NO: 1, 2, 3, 4 or 5, and the subject nucleotide sequence preferably is SEQ ID NO: 9, 10, 11, 12 or 13.

A "homologous sequence" includes a polynucleotide or a polypeptide having a certain percent, e.g., 80%, 85%, 90%, 95%, or 99%, of sequence identity with another sequence.

Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following removal of a signal sequence, for example. Typically, homologues will comprise the same active site residues as the subject amino acid sequence. Homologues also retain enzymatic activity, although the homologue may have different enzymatic properties than the wild-type.

As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, the term "fragment" is defined herein as a polypeptide having one or more (several) amino acids deleted from the amino and/or carboxyl terminus wherein the fragment has activity.

In one aspect, the term "fragment" is defined herein as a polypeptide having one or more (several) amino acids deleted from the amino and/or carboxyl terminus of the polypeptide of SEQ ID NO: 1, 2, 3, 4 or 5; wherein the fragment has transgalactosylating activity.

The term "Galactose Binding domain-like" as used herein is abbreviated to and interchangeable with the term "GBD".

Degree of Identity

The relatedness between two amino acid sequences or between two nucleotide sequences is described by the parameter "identity".

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the reference sequence.

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the longest of the two sequences.

In another embodiment, the degree of sequence identity between the query sequence and the reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the "alignment length", where the alignment length is the length of the entire alignment including gaps and overhanging parts of the sequences.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score), ii) assignment of a penalty score each time an existing gap is extended with an extra position (extension penalty score), iii) assignment of high scores upon alignment of identical amino acids, and iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/ and which was firstly described in Altschul et al. (1990) J. Mol. Biol. 215; 403-410.

In a preferred embodiment of the present invention, the alignment program is performing a global alignment program, which optimizes the alignment over the full-length of the sequences. In a further preferred embodiment, the global alignment program is based on the Needleman-Wunsch algorithm (Needleman, Saul B.; and Wunsch, Christian D. (1970), "A general method applicable to the search for similarities in the amino acid sequence of two proteins", *Journal of Molecular Biology* 48 (3): 443-53). Examples of current programs performing global alignments using the Needleman-Wunsch algorithm are EMBOSS Needle and EMBOSS Stretcher programs, which are both available at http://www.ebi.ac.uk/Tools/psa/.

EMBOSS Needle performs an optimal global sequence alignment using the Needleman-Wunsch alignment algorithm to find the optimum alignment (including gaps) of two sequences along their entire length.

EMBOSS Stretcher uses a modification of the Needleman-Wunsch algorithm that allows larger sequences to be globally aligned.

In one embodiment, the sequences are aligned by a global alignment program and the sequence identity is calculated by identifying the number of exact matches identified by the program divided by the "alignment length", where the alignment length is the length of the entire alignment including gaps and overhanging parts of the sequences.

In a further embodiment, the global alignment program uses the Needleman-Wunsch algorithm and the sequence identity is calculated by identifying the number of exact matches identified by the program divided by the "alignment length", where the alignment length is the length of the entire alignment including gaps and overhanging parts of the sequences.

In yet a further embodiment, the global alignment program is selected from the group consisting of EMBOSS Needle and EMBOSS stretcher and the sequence identity is calculated by identifying the number of exact matches identified by the program divided by the "alignment length", where the alignment length is the length of the entire alignment including gaps and overhanging parts of the sequences.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:
Gap opening penalty: 10
Gap extension penalty: 0.05
Gap separation penalty range: 8

In a another embodiment, the alignment of one amino acid sequence with, or to, another amino acid sequence is determined by the use of the score matrix: blosum62mt2 and the VectorNTI Pair wise alignment settings

| Settings | K-tuple | 1 |
|---|---|---|
| | Number of best diagonals | 5 |
| | Window size | 5 |
| | Gap Penalty | 3 |
| | Gap opening Penalty | 10 |
| | Gap extension Penalty | 0.1 |

In one embodiment, the percentage of identity of one amino acid sequence with, or to, another amino acid sequence is determined by the use of Blast with a word size of 3 and with BLOSUM 62 as the substitution matrix
Polypeptides In one aspect, disclosed herein is a polypeptide having a ratio of transgalactosylating activity:β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

In one aspect, disclosed herein is a polypeptide, wherein the glycoside hydrolase catalytic core has an amino acid sequence of SEQ ID NO:7.

In one aspect, disclosed herein is a polypeptide containing a Glyco_hydro2N (PF02837), a Glyco_hydro (PF00703) and/or a Glyco_hydro 2C (PF02836) domains.

In one aspect, disclosed herein is a polypeptide containing the Bacterial Ig-like domain (group 4) (PF07532).

In one aspect, disclosed herein is a polypeptide having transgalactosylating activity selected from the group consisting of:
  a. a polypeptide comprising an amino acid sequence having at least 90% sequence identity with SEQ ID NO: 1, wherein said polypeptide consists of at most 980 amino acid residues,
  b. a polypeptide comprising an amino acid sequence having at least 97% sequence identity with SEQ ID NO: 2, wherein said polypeptide consists of at most 975 amino acid residues,
  c. a polypeptide comprising an amino acid sequence having at least 96.5% sequence identity with SEQ ID NO: 3, wherein said polypeptide consists of at most 1300 amino acid residues,
  d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i),
  e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and f. a polypeptide comprising a deletion, insertion and/or conservative substitution of one or more amino acid residues of SEQ ID NO: 1, 2, 3, 4 or 5.

In another aspect disclosed herein is a polypeptide having transgalactosylating activity selected from the group consisting of:

a. a polypeptide comprising an amino acid sequence having at least 96.5% sequence identity with SEQ ID NO: 3, wherein said polypeptide consists of at most 1300 amino acid residues, b. a polypeptide comprising an amino acid sequence having at least 90% sequence identity with SEQ ID NO: 1, wherein said polypeptide consists of at most 980 amino acid residues, c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i), d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and e. a polypeptide comprising a deletion, insertion and/or conservative substitution of one or more amino acid residues of SEQ ID NO: 1, 2, 3, 4 or 5.

In one aspect, disclosed herein is a polypeptide, wherein the amino acid sequence has at least 68%, 70%, 72%, 74%, 76%, 78%, 80%, 85%, 90%, 91%, 92%, 93%, 94%, 95%, 96%, 97%, 98%, or 99%, sequence identity to the mature amino acid sequence of SEQ ID NO: 1, 2, 3, 4 or 5.

In one aspect, disclosed herein is a polypeptide having 90% sequence identity to the mature amino acid sequence of SEQ ID NO:1.

In one aspect, disclosed herein is a polypeptide having 90% sequence identity to the mature amino acid sequence of SEQ ID NO:2.

In one aspect, disclosed herein is a polypeptide having 96.5% sequence identity to the mature amino acid sequence of SEQ ID NO:3.

In one aspect, disclosed herein is a polypeptide having 96.5% sequence identity to the mature amino acid sequence of SEQ ID NO:4.

In one aspect, disclosed herein is a polypeptide having 96.5% sequence identity to the mature amino acid sequence of SEQ ID NO:5.

In one aspect, disclosed herein is a polypeptide comprising or consisting of the amino acid sequence of SEQ ID NO:1, 2, 3, 4 or 5.

In one aspect, disclosed herein is a polypeptide, which is derived from *Bifidobacterium bifidum*.

In one aspect, disclosed herein is a polypeptide having a pH optimum of 6.5-7.5.

In one aspect, disclosed herein is a polypeptide having a temperature optimum of 30-60 such as 42-60 degree celcius.

Polypeptides having activity on carbohydrates can be classified using either the IUBMB system of classification based on their substrate specificity or on the CaZy assignment into one of the current 125 glycoside hydrolase family. In the CaZy database the assignment is based on both sequence and structural information combined with knowledge of stereochemistry of the substrates and products Disclosed herein are polypeptides which when being an expression product in a *Bacillus subtilis* strain BG3594 of a nucleic acid sequence, which encodes said polypeptide, is the only polypeptide expression product of said nucleic acid sequence that exhibits transgalactosylating activity. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometic scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity)*100.

The total number of polypeptides variants/fragments derived from SEQ ID NO:8 in the composition can be determined by detecting fragment derived from SEQ ID NO:8 by western blotting using a polyclonal antibody by methods know to a person skilled in the art.

The polypeptide disclosed herein comprises at least two separate functional domains contained within the enzyme. Firstly, the polypeptide should contain a glycoside hydrolase catalytic core as described in the following. The catalytic core should belong to the GH-A clan of related glycoside hydrolase families. The GH-A clan is characterized by cleaving glycosidic bonds via a retaining mechanism and possesses a catalytic domain which is based on a TIM barrel fold (Wierenga, 2001, FEBS Letters, 492(3), p 193-8). The catalytic domain contains two glutamic acid residues which act as proton donor and nucleophile, emanating from strands 4 and 7 of the barrel domain (Jenkins, 1995, FEBS Letters, 362(3), p 281-5). The overall structure of the TIM barrel is a ($\beta$/$\alpha$) 8 fold consisting of 8 beta strands and 8 alpha-helices. In one aspect, the glycoside hydrolase catalytic core disclosed herein belong to either of the glycoside hydrolase families GH-2, and −35 which are all TIM-barrel enzymes belonging to the GH-A clan. In a further aspect, the glycoside hydrolase catalytic core belong to family GH-2 or GH-35. In a further aspect, the glycoside hydrolase catalytic core belong to family GH-2. A common denominator is that these enzymes are so called retaining enzymes, so that the stereochemistry of the substrate is conserved in the product (Henrissat, 1997, Curr Opin Struct Biol, 7(5), 637-44).

In one aspect, the polypeptides disclosed herein have activity on carbohydrates bonds which has the $\beta(1\rightarrow4)$ conformation. This effectively put the enzymes into the IUBMB EC 3.2.1.23 class of $\beta$-galactosidases. This activity may be, but is not confined to, determined by utilizing synthetic substrates such as para-nitrophenol-$\beta$-D-galactopyranoside (PNPG), ortho-nitrophenol-$\beta$-D-galactopyranoside (ONPG) or $\beta$-D-galactopyranoside with chromogenic aglycons (XGal). As an alternative way of determining whether an enzyme belong to the EC 3.2.1.23 class of $\beta$-galactosidases is to incubate with a substrate such as lactose and measure the release of glucose by a method such as enzymatic determination, HPLC, TLC or other methods known to persons skilled in the art.

In order to predict functional entities of polypeptides several available public repositories can be applied such as for example Pfam (Nucl. Acids Res. (2010) 38 (suppl 1): D211-D222. doi: 10.1093/nar/gkp985) and Interpro (Nucl. Acids Res. (2009) 37 (suppl 1): D211-D215. doi: 10.1093/nar/gkn785). It should be specified that when performing such analysis the analysis should be performed on the full length sequence of the polypeptide available from public repository databases.

In a further aspect, a polypeptide containing one or more Pfam domains selected from: Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Pfam domains Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Glyco_hydro2N (PF02837), Glyco_hydro (PF00703), and Glyco_hydro 2C (PF02836) domains which constitutes the catalytic domain of the polypeptide, is provided.

In a further aspect, a polypeptide as disclosed herein and having a ratio of transgalactosylating activity:β-galactosidase activity of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, is provided. In a further aspect, the polypeptide is derived from Bifidobacterium bifidum.

In one aspect, the herein disclosed polypeptide(s) has a transgalactosylating activity such that more than 20%, more than 30%, more than 40%, up to 50% of the initial lactose is transgalactosylated as measured at a concentration of 100 ppm in a milk-based assay at 37° C. and 5 w/w % lactose after 15, 30 or 180 such as 180 minutes of reaction.

In a further aspect, the herein disclosed polypeptide(s) has a β-galactosidase activity such that less than 80%, less than 70%, less than 60%, less than 50%, less than 40%, less than 30%, less than 20% of the lactose has been hydrolysed as measured at a concentration of 100 ppm in a milk-based assay at 37° C. and 5 w/w % lactose after 15, 30 or 180 such as 180 minutes of reaction.

In one aspect, the β-galactosidase activity and/or the transgalactosylating activity are measured at a concentration of 100 ppm corresponding to 2.13 LAU as specified in method 4.

In a further aspect, the herein disclosed polypeptide(s) has one or more of the following characteristics:
a) a ratio of transgalactosylating activity:β-galactosidase activity of at least of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, and/or
b) has a transgalactosylating activity such that more than 20%, more than 30%, more than 40%, and up to 50% of the initial lactose has been transgalactosylated as measured at a concentration of 100 ppm in a milk-based assay at 37° C. and 5 w/w % lactose after 15, 30 or 180 such as 180 minutes of reaction.

In one aspect, a polypeptide comprising an amino acid sequence having at least 96.5% sequence identity with SEQ ID NO: 3, wherein said polypeptide consists of at most 1300 amino acid residues, is provided. In a further aspect, a polypeptide comprising an amino acid sequence having at least 90% sequence identity with SEQ ID NO: 1 such as wherein said sequence identity is at least 95%, such as, e.g. at least 96%, at least 97%, at least 98%, at least 99% or at least 100% sequence identity, and wherein said polypeptide consists of at most 980 amino acid residues, is provided. In a further aspect, a polypeptide comprising an amino acid sequence having at least 90% sequence identity with SEQ ID NO: 1, wherein said polypeptide consists of at most 980 amino acid residues, is provided. In yet a further aspect, a polypeptide wherein said polypeptide has at least 90% sequence identity with SEQ ID NO: 1, such as wherein said polypeptide has at least 90%, such as, e.g. at least 91%, at least 92%, at least 93%, at least 94%, at least 95%, at least 96%, at least 97%, at least 98%, or at least 99% sequence identity with SEQ ID NO: 1 is provided. In another aspect, a polypeptide having at least 96.5% sequence identity to SEQ ID NO: 2 such as wherein said polypeptide has at least 97%, such as, e.g. at least 98% or at least 99% sequence identity with SEQ ID NO: 2. In one aspect, the polypeptides disclosed herein consist of at the most 975 amino acid residues, such as, e.g. at most 970 amino acid residues, such as at most 950 amino acid residues, such as at most 940 amino acid residues, at most 930 amino acid residues, at most 920 amino acid residues, at most 910 amino acid residues, at most 900 amino acid residues, at most 895 amino acid residues or at most 890 amino acid residues, is provided. In one aspect, a particular polypeptide consists of 887 or 965 amino acid residues, is provided. In one aspect, a polypeptide comprising an amino acid sequence having at least 97% sequence identity with SEQ ID NO: 2 such as wherein said sequence identity is at least 98%, such as, e.g. at least 99% or at least 100% sequence identity, wherein said polypeptide consists of at most 975 amino acid residues, such as, e.g. at most 970 or at least 965 amino acid residues, is provided. In one aspect, a polypeptide comprising an amino acid sequence having at least 97% sequence identity with SEQ ID NO: 2, wherein said polypeptide consists of at most 975 amino acid residues, is provided.

In a further preferred aspect, a polypeptide which comprises SEQ ID NO:1, 2, 3, 4 or 5, is provided. In yet a preferred aspect, a polypeptide consisting of the amino acid sequence of SEQ ID NO: 1, 2, 3, 4, or 5, especially a polypeptide consisting of the amino acid sequence of SEQ ID NO: 1 or 2, is provided.

In a further aspect, a polypeptide comprising an amino acid sequence having at least 96.5% sequence identity with SEQ ID NO: 3 such as wherein said sequence identity is at least 97%, such as, e.g. at least 98%, at least 99% or at least 100% sequence identity, wherein said polypeptide consists of at most 1300 amino acid residues, is provided.

In a further aspect, a polypeptide wherein said polypeptide has at least 98.5%, such as at least 99% or at least 99.5% sequence identity with SEQ ID NO: 5, is provided. In one aspect, such a polypeptide consists of at most 1290 amino acid residues, such as, e.g. at most 1280, at most 1270, at most 1260, at most 1250, at most 1240, at most 1230, at most 1220 or at most 1215 amino acid residues, is provided. In a preferred aspect, a polypeptide which consists of 1211 amino acid residues, is provided.

In a further aspect, a polypeptide wherein said polypeptide has at least 96% such as at least at least 97%, such as, e.g., at least 98% or at least 99% sequence identity with SEQ ID NO: 4, is provided. In one aspect, a polypeptide which consists of at most 1210 amino acid residues, such as, e.g. at most 1200, at most 1190, at most 1180, at most 1170, at most 1160, at most 1150 or at most 1145 amino acid residues, such as 1142 amino acid residues, is provided.

In a further aspect, a polypeptide wherein said polypeptide has at least 96.5% such as at least 97%, such as, e.g., at least 98% or at least 99% sequence identity with SEQ ID NO: 3, is provided. In one aspect, a polypeptide which consists of at most 1130 amino acid residues, such as, e.g. at the most 1120, at the most 1110, at the most 1100, at the most 1090, at the most 1080, at the most 1070, at the most 1060, at the most 1050, at the most 1055 or at the most 1040 amino acid residues, is provided. In a preferred aspect, a polypeptide which consists of 1038 amino acid residues, is provided.

In a further aspect, the polypeptides disclosed herein has a ratio of transgalactosylation activity above 100% such as above 150%, 175% or 200%.

Proteins are generally comprised of one or more functional regions, commonly termed domains. The presence of different domains in varying combinations in different proteins gives rise to the diverse repertoire of proteins found in nature. One way of describing the domains are by the help of the Pfam database which is a large collection of protein domain families as described in "*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222. Each family is represented by multiple sequence alignments and hidden Markov models (HMMs). In a further aspect, the present inventors have found that the herein provided polypeptide(s) contains one or more of the Pfam domains Glyco_hydro2N (PF02837), Glyco_hydro (PF00703), Glyco_hydro 2C (PF02836) and Bacterial Ig-like domain (group 4) (PF07532). In one aspect, the herein provided polypeptide(s) contains Glyco_hydro2N (PF02837), Glyco_hydro (PF00703), Glyco_hydro 2C (PF02836) and Bacterial Ig-like domain (group 4) (PF07532).

In one aspect, the polypeptides have useful transgalactosylating activity over a range of pH of 4-9, such as 5-8, such as 5.5-7.5, such as 6.5-7.5.

The present invention encompasses polypeptides having a certain degree of sequence identity or sequence homology with amino acid sequence(s) defined herein or with a polypeptide having the specific properties defined herein. The present invention encompasses, in particular, peptides having a degree of sequence identity with any one of SEQ ID NO: 1, 2, 3, 4 or 5, defined below, or homologues thereof.

In one aspect, the homologous amino acid sequence and/or nucleotide sequence should provide and/or encode a polypeptide which retains the functional transgalactosylating activity and/or enhances the transgalactosylating activity compared to a polypeptide of SEQ ID NO: 1, 2, 3, 4 or 5.

In the present context, a homologous sequence is taken to include an amino acid sequence which may be at least 66%, 70%, 75%, 78%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Thus, the present invention also encompasses variants, homologues and derivatives of any amino acid sequence of a protein or polypeptide as defined herein, particularly those of SEQ ID NO: 1, 2, 3, 4 or 5 defined below.

The sequences, particularly those of variants, homologues and derivatives of SEQ ID NO: 1, 2, 3, 4 or 5 defined below, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

In one aspect, the polypeptide sequence used in the present invention is in a purified form. In one aspect, the polypeptide or protein for use in the present invention is in an isolated form.

In one aspect, the polypeptide of the present invention is recombinantly produced.

The variant polypeptides include a polypeptide having a certain percent, e.g., at least 90%, 91%, 92%, 93%, 94%, 95%, 96%, 97%, 98%, or 99%, of sequence identity with SEQ ID NO: 1 or 2.

The variant polypeptides include a polypeptide having a certain percent, e.g., at least 96%, 97%, 98%, or 99%, of sequence identity with SEQ ID NO: 3, 4 or 5.

In one aspect, the polypeptides disclosed herein comprises an amino acid sequence having at least 90%, 91%, 92%, 93%, 94%, 95%, 96%, 97%, 98%, or 99% sequence identity to the amino acid sequence of the mature polypeptide encoded by the nucleotide sequence encoding the transgalatosylase contained in *Bifidobacterium bifidum* DSM20215 shown herein as SEQ ID NO: 22. All considerations and limitations relating to sequence identities and functionality discussed in terms of the SEQ ID NO: 1, 2, 3, 4 or 5 apply mutatis mutandis to sequence identities and functionality of these polypeptides and nucleotides.

In one aspect, the subject amino acid sequence is SEQ ID NO: 1, 2, 3, 4 or 5, and the subject nucleotide sequence preferably is SEQ ID NO: 9, 10, 11, 12 or 13.

In one aspect, the polypeptide is a fragment having one or more (several) amino acids deleted from the amino and/or carboxyl terminus of the polypeptide of SEQ ID NO: 1, 2, 3, 4 or 5; wherein the fragment has transgalactosylating activity.

In one aspect, a fragment contains at least 500, 550, 600, 650, 700, 750, 800, 850, 900, 950, or 1000 amino acid residues In a further aspect, the length of the polypeptide variant is 500 to 1300 amino acid residues. In a further aspect, the length of the polypeptide variant is 600 to 1300 amino acids. In a further aspect, the length of the polypeptide variant is 700 to 1300 amino acids. In a further aspect, the length of the polypeptide variant is 800 to 1300 amino acids. In a further aspect, the length of the polypeptide variant is 800 to 1300 amino acids.

Polypeptide Variants of SEQ ID NO: 1, 2, 3, 4 or 5

In one aspect, a variant of SEQ ID NO: 1, 2, 3, 4 or 5 having a substitution at one or more positions which effects an altered property such as improved transgalactosylation, relative to SEQ ID NO: 1, 2, 3, 4 or 5, is provided. Such variant polypeptides are also referred to in this document for convenience as "variant polypeptide", "polypeptide variant" or "variant". In one aspect, the polypeptides as defined herein have an improved transgalactosylating activity as compared to the polypeptide of SEQ ID NO: 1, 2, 3, 4 or 5. In another aspect, the polypeptides as defined herein have an improved reaction velocity as compared to the polypeptide of SEQ ID NO: 1, 2, 3, 4 or 5.

In one aspect, the polypeptides and variants as defined herein exhibit enzyme activity. In one aspect, the polypeptides and the variant polypeptides described herein comprise transgalactosylation activity.

In one aspect, the ratio of transgalactosylating activity:β-galactosidase activity is at least 0.5, such as at least 1, such as at least 1.5, or such as at least 2 after 30 min. reaction such as above a concentration of 3% w/w initial lactose concentration.

In one aspect, the ratio of transgalactosylating activity:β-galactosidase activity is at least 2.5, such as at least 3, such as at least 4, such as at least 5, such as at least 6, such as at least 7, such as at least 8, such as at least 9, such as at least 10, such as at least 11, or such as at least 12 after 30 min. reaction such as above a concentration of 3% w/w initial lactose concentration.

In one aspect, the polypeptides and the variants as defined herein are derivable from microbial sources, in particular from a filamentous fungus or yeast, or from a bacterium. The enzyme may, e.g., be derived from a strain of *Agaricus*, e.g. *A. bisporus*; *Ascovaginospora*; *Aspergillus*, e.g. *A. niger*, *A. awamori*, *A. foetidus*, *A. japonicus*, *A. oryzae*; *Candida*; *Chaetomium*; *Chaetotomastia*; *Dictyostelium*, e.g. *D. discoideum*; *Kiuveromyces*, e.g. *K. fragilis*, *K. lactis*; *Mucor*, e.g. *M. javanicus*, *M. mucedo*, *M. subtilissimus*; *Neurospora*, e.g. *N. crassa*; *Rhizomucor*, e.g. *R. pusillus*; *Rhizopus*, e.g. *R. arrhizus*, *R. japonicus*, *R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans*, *B. circulans*, *B. megaterium*, *B. novalis*, *B. subtilis*, *B. pumilus*, *B. stearothermophilus*, *B. thuringiensis*; *Bifidobacterium*, e.g. *B. Iongum*, *B. bifidum*, *B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes*, *E. cloacae Edwardsiella*, *E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus*, *Pycnoporus sanguineus*; *Ruminococcus*, e.g. *R. torques*; *Salmonella*, e.g. *S. typhimurium*; *Serratia*, e.g. *S. liquefasciens*, *S. marcescens*; *Shigella*, e.g. *S. flexneri*; *Streptomyces*, e.g. *S. antibioticus*, *S. castaneoglobisporus*, *S. violeceoruber*; *Trametes*; *Trichoderma*, e.g. *T. reesei*, *T. viride*; *Yersinia*, e.g. *Y. enterocolitica*.

An isolated and/or purified polypeptide comprising a polypeptide or a variant polypeptide as defined herein is provided. In one embodiment, the variant polypeptide is a mature form of the polypeptide (SEQ ID NO: 1, 2, 3, 4 or 5). In one aspect, the variants include a C-terminal domain.

In one aspect, a variant polypeptide as defined herein includes variants wherein between one and about 25 amino acid residues have been added or deleted with respect to SEQ ID NO: 1, 2, 3, 4 or 5. In one aspect, a variant polypeptide as defined herein includes variants wherein between one and 25 amino acid residues have been substituted, added or deleted with respect to SEQ ID NO: 1, 2, 3, 4 or 5. In one aspect, the variant has the amino acid sequence of SEQ ID NO: 1, 2, 3, 4 or 5, wherein any number between one and about 25 amino acids have been substituted. In a further aspect, the variant has the amino acid sequence of SEQ ID NO: 1, 2, 3, 4 or 5, wherein any number between three and twelve amino acids has been substituted. In a further aspect, the variant has the amino acid sequence of SEQ ID NO: 1, 2, 3, 4 or 5, wherein any number between five and nine amino acids has been substituted.

In one aspect, at least two, in another aspect at least three, and yet in another aspect at least five amino acids of SEQ ID NO: 1, 2, 3, 4 or 5 have been substituted.

In one aspect, the herein disclosed polypeptide(s) has the sequence of 1, 2, 3, 4 or 5.

In one aspect, the herein disclosed polypeptide(s) has the sequence of SEQ ID NO: 1, 2, 3, 4 or 5, wherein the 10, such as 9, such as 8, such as 7, such as 6, such 5, such as 4, such as 3, such as 2, such as 1 amino acid in the N-terminal end are substituted and/or deleted.

Enzymes and enzyme variants thereof can be characterized by their nucleic acid and primary polypeptide sequences, by three dimensional structural modeling, and/or by their specific activity. Additional characteristics of the polypeptide or polypeptide variants as defined herein include stability, pH range, oxidation stability, and thermostability, for example. Levels of expression and enzyme activity can be assessed using standard assays known to the artisan skilled in this field. In another aspect, variants demonstrate improved performance characteristics relative to the polypeptide with SEQ ID NO: 1, 2, 3, 4 or 5, such as improved stability at high temperatures, e.g., 65-85° C.

A polypeptide variant is provided as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5.

Nucleotides

In one aspect, the present invention relates to isolated polypeptides having transgalactosylating activity as stated above which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with i) the nucleic acid sequence comprised in SEQ ID NO: 9, 10, 11, 12 or 13 encoding the mature polypeptide of SEQ ID NO: 1, 2, 3, 4 or 5; ii) the cDNA sequence of i) or iii) the complementary strand of i) or ii), (J. Sambrook, E. F. Fritsch, and T. Maniatis, 1989, *Molecular Cloning, A Laboratory Manual*, 2d edition, Cold Spring Harbor, N.Y.). A subsequence of SEQ ID NO: 9, 10, 11, 12 or 13 contains at least 100 contiguous nucleotides or preferably at least 200 contiguous nucleotides. Moreover, the subsequence may encode a polypeptide fragment which has lactase activity.

The nucleotide sequence of SEQ ID NO: 9, 10, 11, 12 or 13 or a subsequence thereof, as well as the amino acid sequence of SEQ ID NO: 1, 2, 3, 4 or 5 or a fragment thereof, may be used to design a nucleic acid probe to identify and clone DNA encoding polypeptides having transgalactosylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA which hybridizes with the probes described above and which encodes a polypeptide having lactase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 9, 10, 11, 12 or 13 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 9, 10, 11, 12 or 13, its complementary strand, or a subsequence thereof, under very low to very high stringency conditions. Molecules to which the nucleic acid probe hybridizes under these conditions can be detected using X-ray film.

In another preferred aspect, the nucleic acid probe is the mature polypeptide coding region of SEQ ID NO: 9, 10, 11, 12 or 13.

For long probes of at least 100 nucleotides in length, very low to very high stringency conditions are defined as prehybridization and hybridization at 42° C. in 5×SSPE, 0.3% SDS, 200 g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[Na^+]) + 0.41(\% \, G+C) - 0.72(\% \text{ formamide})$$

(See www.ndsu.nodak.edu/instruct/mcclean/plsc731/dna/dna6.htm)

The G+C content of SEQ ID NO: 10 is 42% and the G+C content of SEQ ID NO: 11 is 44%. For medium stringency, the formamide is 35% and the Na$^+$ concentration for 5×SSPE is 0.75 M.

Another relevant relationship is that a 1% mismatch of two DNAs lowers the $T_m$ by 1.4° C. To determine the degree of identity required for two DNAs to hybridize under medium stringency conditions at 42° C., the following formula is used:

$$\% \text{ Homology} = 100 - [(\text{Effective } T_m - \text{Hybridization Temperature})/1.4]$$

(See www.ndsu.nodak.edu/instruct/mcclean/plsc731/dna/dna6.htm)

The variant nucleic acids include a polynucleotide having a certain percent, e.g., 60%, 65%, 70%, 75%, 80%, 85%, 90%, 95%, or 99%, of sequence identity with the nucleic acid encoding SEQ ID NO: 1, 2, 3, 4 or 5. In one aspect, a nucleic acid capable of encoding a polypeptide as disclosed herein, is provided. In a further aspect, the herein disclosed nucleic acid has a nucleic acid sequence which is at least 60%, such as at least 65%, such as at least 70%, such as at least 75%, such as at least 80%, such as at least 85%, such as at least 90%, such as at least 95%, such as at least 99% identical SEQ ID NO: 9, 10, 11, 12 or 13.

In one aspect, a plasmid comprising a nucleic acid as described herein, is provided.

In one aspect, an expression vector comprising a nucleic acid as described herein, or capable of expressing a polypeptide as described herein, is provided.

A nucleic acid complementary to a nucleic acid encoding any of the polypeptide variants as defined herein set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast. The polypeptide variants as provided herein may be produced synthetically or through recombinant expression in a host cell, according to procedures well known in the art. In one aspect, the herein disclosed polypeptide(s) is recombinant polypeptide(s). The expressed polypeptide variant as defined herein optionally is isolated prior to use.

In another embodiment, the polypeptide variant as defined herein is purified following expression. Methods of genetic modification and recombinant production of polypeptide variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, $Ca^{2+}$ concentrations, substrate concentrations and enzyme concentrations for enzymatic assays, are herein incorporated by reference.

A nucleic acid sequence is provided encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Vectors

In one aspect, the invention relates to a vector comprising a polynucleotide. In one aspect, a bacterial cell comprises the vector. In some embodiments, a DNA construct comprising a nucleic acid encoding a variant is transferred to a host cell in an expression vector that comprises regulatory sequences operably linked to an encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., MOLECULAR CLONING: A LABORATORY MANUAL, 3$^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEM®3Z and pGEM®4Z. Exemplary for use in bacterial cells include pBR322 and pUC19, which permit replication in *E. coli*, and pE194, for example, which permits replication in *Bacillus*.

In some embodiments, a nucleic acid encoding a variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when *P. saccharophila* is the host, the promoter is a native *P. saccharophila* promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. In another aspect, a representative signal peptide is SEQ ID NO: 27. A representative signal peptide is SEQ ID NO: 9 which is the native signal sequence of the *Bacillus subtilis* aprE precursor. In other embodiments, the DNA encoding the signal sequence is replaced with a nucleotide sequence encoding a signal sequence from other extra-cellular *Bacillus subtilis* pre-cursors. In one embodiment, the polynucleotide that encodes the signal sequence is immediately upstream and in-frame of the polynucleotide that encodes the polypeptide. The signal sequence may be selected from the same species as the host cell.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an *A. nidulans* amdS gene as a selective marker is described in Kelley et al., *EMBO J.* 4: 475-479 (1985) and Penttila et al., *Gene* 61: 155-164 (1987).

A suitable expression vector comprising a DNA construct with a polynucleotide encoding a variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, coding region, and terminator all originate from the gene to be expressed. In some embodiments, gene truncation is obtained by deleting undesired DNA sequences to leave the domain to be expressed under control of its own transcriptional and translational regulatory sequences. The second type of expression vector is preassembled and contains sequences required for high-level transcription and a selectable marker. In some embodiments, the coding region for a gene or part thereof is inserted into this general-purpose expression vector, such that it is under the transcriptional control of the expression construct promoter and terminator sequences. In some embodiments, genes or part thereof are inserted downstream of the strong cbh1 promoter.

Expression Hosts/Host Cells

In a further aspect, a host cell comprising, preferably transformed with, a plasmid as described herein or an expression vector as described herein, is provided.

In a further aspect, a cell capable of expressing a polypeptide as described herein, is provided.

In one aspect, the host cell as described herein, or the cell as described herein is a bacterial, fungal or yeast cell.

In a further aspect, the host cell is selected from the group consisting of *Ruminococcus*, *Bifidobacterium*, *Lactococcus*, *Lactobacillus*, *Streptococcus*, *Leuconostoc*, *Escherichia*, *Bacillus*, *Streptomyces*, *Saccharomyces*, *Kluyveromyces*, *Candida*, *Torula*, *Torulopsis* and *Aspergillus*.

In a further aspect, the host cell is selected from the group consisting of *Ruminococcus hansenii*, *Bifidobacterium breve*, *Bifidobacterium longum*, *Bifidobacterium infantis*, *Bifidobacterium bifidum* and *Lactococcus lactis*.

In another embodiment, suitable host cells include a Gram positive bacterium selected from the group consisting of *Bacillus subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus*, *B. thuringiensis*, *Streptomyces lividans*, or *S. murinus*; or a Gram negative bacterium, wherein said Gram negative bacterium is *Escherichia coli* or a *Pseudomonas* species. In one aspect, the host cell is a *B. subtilis* or *B. licheniformis*. In one embodiment, the host cell is *B. subtilis*, and the expressed protein is engineered to comprise a *B. subtilis* signal sequence, as set forth in further detail below. In one aspect, the host cell expresses the polynucleotide as set out in the claims.

In some embodiments, a host cell is genetically engineered to express a polypeptide variant as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5. In some embodiments, the polynucleotide encoding a polypeptide variant as defined herein will have a nucleic acid sequence encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Methods for Producing Polypeptides

In a further aspect, a method of expressing a polypeptide as described herein comprises obtaining a host cell or a cell as described herein and expressing the polypeptide from the cell or host cell, and optionally purifying the polypeptide.

An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant polypeptide.

Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., *Curr. Genet.* 16: 53-56 (1989). The expression of heterologous protein in *Trichoderma* is described, for example, in U.S. Pat. Nos. 6,022,725; 6,268,328; Harkki et al., *Enzyme Microb. Technol.* 13: 227-233 (1991); Harkki et al., *BioTechnol.* 7: 596-603 (1989); EP 244,234; and EP 215, 594. In one embodiment, genetically stable transformants are constructed with vector systems whereby the nucleic acid encoding a variant is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

Identification of Activity

To evaluate the expression of a variant in a host cell, assays can measure the expressed protein, corresponding mRNA, or β-galactosidase activity. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the activity of the variant include, but are not limited to, ONPG based assays or determining glucose in reaction mixtures such for example described in the methods and examples herein.

Methods for Purifying Herein Disclosed Polypeptides

In general, a variant produced in cell culture is secreted into the medium and may be purified or isolated, e.g., by removing unwanted components from the cell culture medium. In some cases, a variant may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example. Depending on the intended use the herein disclosed polypeptide(s) may for example be either freeze-dried or prepared in a solution. In one aspect, the herein disclosed polypeptide(s) is freeze-dried form. In another aspect, the herein disclosed polypeptide(s) is in solution.

Compositions, Application and Use
Methods for Immobilising and Formulation of the Herein Disclosed Polypeptides The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art. Examples are given below of preferred uses of the polypeptides or polypeptide compositions of the invention.

In one aspect, disclosed herein is a method for producing a food product by treating a substrate comprising lactose with a polypeptide as described herein.

In one aspect, disclosed herein is a method for producing a dairy product by treating a milk-based substrate comprising lactose with a polypeptide as described herein.

In one aspect, the substrate comprising lactose is further treated with a hydrolysing beta-galactosidase.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

Examples of dry enzyme formulations include spray dried products, mixer granulation products, layered products suc as fluid bed granules, extruded or pelletized granules prilled products, lyophilyzed products.

The enzyme preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

In one aspect, a composition preferably a food composition, more preferably a dairy product comprising a cell or a polypeptide as described herein, is provided.

Furthermore, disclosed herein is a composition comprising at least 5%, such as e.g. 10%, 15%, 20%, 25%, 30%, 35%, 40%, 45%, 50% w/w of one or more polypeptide(s) as disclosed herein based on the total amount of polypeptides in the composition having at least 70%,e.g. such as 72%, 74%, 74%, 78%, 80%, 82%, 84%, 86%, 88%, 90% sequence identity with SEQ ID NO: 22. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometic scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity) *100. The total number of polypeptides variants/fragments derived from SEQ ID NO:8 in the composition can be determined by detecting fragment derived from SEQ ID NO:8 by western blotting using a polyclonal antibody by methods know to a person skilled in the art.

In one aspect, the composition according to the present invention comprises one or more polypeptide(s) selected from the group consisting of a polypeptide consisting of SEQ ID NO: 1, 2, 3, 4 and 5. In a further aspect, the composition comprises one or more polypeptide(s) selected from the group consisting of a polypeptide consisting of SEQ ID NO: 1, 2 and 3. In yet a further aspect, the composition comprises one or more polypeptide(s) selected from the group consisting of a polypeptide consisting of SEQ ID NO: 1 and 2.

In one aspect the invention provides an enzyme complex preparation comprising the enzyme complex according to the invention, an enzyme carrier and optionally a stabilizer and/or a preservative.

In yet a further aspect of the invention, the enzyme carrier is selected from the group consisting of glycerol or water.

In a further aspect, the preparation/composition comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol, propylene glycol, or sorbitol. In yet another aspect, the sugar is a small-molecule carbohydrate, in particular any of several sweet-tasting ones such as glucose, galactose, fructose and saccharose.

In yet at further aspect, the preparation comprises a preservative. In one aspect, the preservative is methyl paraben, propyl paraben, benzoate, sorbate or other food approved preservatives or a mixture thereof.

The method of the invention can be practiced with immobilized enzymes, e.g. an immobilized lactase or other galactooligosaccharide producing enzymes. The enzyme can be immobilized on any organic or inorganic support. Exemplary inorganic supports include alumina, celite, Dowex-1-chloride, glass beads and silica gel. Exemplary organic supports include DEAE-cellulose, alginate hydrogels or alginate beads or equivalents. In various aspects of the invention, immobilization of the lactase can be optimized by physical adsorption on to the inorganic support. Enzymes used to practice the invention can be immobilized in different media, including water, Tris-HCl buffer and phosphate buffered solution. The enzyme can be immobilized to any type of substrate, e.g. filters, fibers, columns, beads, colloids, gels, hydrogels, meshes and the like.

In one aspect, a method for producing a dairy product by treating a milk-based substrate comprising lactose with a polypeptide as described herein is provided. In a further aspect, a method for producing a dairy product by treating a milk-based substrate comprising lactose with a polypeptide having a relative transgalactosylation activity above 60%, such as above 70%, such as above 75% after 15 min. reaction, is provided. In one aspect, the relative transgalactosylation activity is above 3 after 30 min. reaction. In a further aspect, the relative transgalactosylation activity is above 6 after 30 min. reaction. In yet a further aspect, the relative transgalactosylation activity is above 12 after 30 min. reaction. In one aspect, a method is provided, wherein the treatment with a polypeptide as described herein takes place at an optimal temperature for the activity of the enzyme. In a further aspect, the polypeptide is added to the milk-based substrate at a concentration of 0.01-1000 ppm. In yet a further aspect, the polypeptide is added to the milk-based substrate at a concentration of 0.1-100 ppm. In a further aspect, the polypeptide is added to the milk-based substrate at a concentration of 1-10 ppm. In one aspect, a method further comprising fermenting a substrate such as a dairy product with a microorganism, is provided. In a further aspect, the dairy product is yogurt. In a further aspect, the treatment with the polypeptide and the microorganism is performed essentially at the same time. In one aspect, the polypeptide and the microorganism are added to the milk-based substrate essentially at the same time. In one aspect, a dairy product comprising a cell or a polypeptide as described herein, is provided. In one aspect, the polypeptide as defined herein is added in a concentration of 0.01-1000 ppm. In one aspect, a dairy product comprising an inactivated polypeptide as defined herein, is provided. In one aspect, a dairy product comprising an inactivated polypeptide as defined herein in a concentration of 0.01-1000 ppm, is provided. In one aspect, a dairy product comprising GOS formed in situ by a polypeptide as defined herein, is provided. In one aspect, a dairy product comprising a cell as defined herein, is provided.

A dairy product as described herein may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavouring agents, microbial cultures such as probiotic cultures, salts, sweeteners, sugars, acids, fruit, fruit juices, or any other component known in the art as a component of, or additive to, a dairy product.

In one embodiment of the invention, one or more milk components and/or milk fractions account for at least 50% (weight/weight), such as at least 70%, e.g. at least 80%, preferably at least 90%, of the dairy product.

In one embodiment of the invention, one or more milk-based substrates having been treated with an enzyme as defined herein having transgalactosylating activity account for at least 50% (weight/weight), such as at least 70%, e.g. at least 80%, preferably at least 90%, of the dairy product.

In one embodiment of the invention, the dairy product is a dairy product which is not enriched by addition of pre-produced galacto-oligosaccharides.

In one embodiment of the invention, the polypeptide-treated milk-based substrate is not dried before being used as an ingredient in the dairy product.

In one embodiment of the invention, the dairy product is ice cream. In the present context, ice cream may be any kind of ice cream such as full fat ice cream, low fat ice cream, or ice cream based on yoghurt or other fermented milk products. Ice cream may be manufactured by any method known in the art.

In one embodiment of the invention, the dairy product is milk or condensed milk.

In one embodiment of the invention, the dairy product is UHT milk. UHT milk in the context of the present invention is milk which has been subjected to a sterilization procedure which is intended to kill all microorganisms, including the bacterial spores. UHT (ultra high temperature) treatment may be, e.g., heat treatment for 30 seconds at 130° C., or heat treatment for one second at 145° C.

In one preferred embodiment of the invention, the dairy product is ESL milk. ESL milk in the present context is milk which has an extended shelf life due to microfiltration and/or heat treatment and which is able to stay fresh for at least 15 days, preferably for at least 20 days, on the store shelf at 2-5° C.

In another preferred embodiment of the invention, the dairy product is a fermented dairy product, e.g., yoghurt.

The microorganisms used for most fermented milk products are selected from the group of bacteria generally referred to as lactic acid bacteria. As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of anaerobic bacteria, bifidobacteria, i.e. *Bifidobacterium* spp., which are frequently used as food cultures alone or in combination with lactic acid bacteria, are generally included in the group of lactic acid bacteria.

Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis biovar. diacetylactis, Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*. Also the anaerobic bacteria belonging to the genus *Bifidobacterium* including *Bifidobacterium bifidum, Bifidobacterium animalis* and *Bifidobacterium longum* are commonly used as dairy starter cultures and are generally included in the group of lactic acid bacteria. Additionally, species of Propionibacteria are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti, Penicillium candidum, Geotrichum candidum, Torula kefir, Saccharomyces kefir* and *Saccharomyces cerevisiae*.

In one embodiment of the present invention, the microorganism used for fermentation of the milk-based substrate is *Lactobacillus casei* or a mixture of *Streptococcus thermophilus* and *Lactobacillus delbrueckii* subsp. *bulgaricus*.

Fermentation processes to be used in a method of the present invention are well known and the person of skill in the art will know how to select suitable process conditions, such as temperature, oxygen, amount and characteristics of microorganism/s, additives such as e.g. carbohydrates, flavours, minerals, enzymes, and process time. Obviously, fermentation conditions are selected so as to support the achievement of the present invention.

As a result of fermentation, pH of the milk-based substrate will be lowered. The pH of a fermented dairy product of the invention may be, e.g., in the range 3.5-6, such as in the range 3.5-5, preferably in the range 3.8-4.8.

In one aspect, a method of using the polypeptides or using any one or more of the above mentioned cell types for producing oligosaccharides, is provided. The oligosaccharides comprise, but are not limited to fructooligo-saccharides, galacto-oligosaccharides, isomalto-oligosaccharides, malto-oligosaccharides, lactosucrose and xylo-oligosaccharides.

In one embodiment of the invention, the oligosaccharides are produced by incubating the cell expressing the polypeptide in a medium that comprises a disaccharide substrate such as for example lactulose, trehalose, rhamnose, maltose, sucrose, lactose, or cellobiose. The incubation is carried out under conditions where oligosaccarides are produced. The cells may be part of a product selected from the group consisting of yoghurt, cheese, fermented milk products, dietary supplements, and probiotic comestible products. Alternatively, the oligosaccharides can be recovered and subsequently be added to the product of interest before or after its preparation.

In one aspect, the use of a herein disclosed cell for producing a product selected from the group consisting of yoghurt, cheese, fermented milk product, dietary supplement and probiotic comestible product, is provided.

In one aspect, the polypeptides described herein may be used to prepare cheese products and in methods for making the cheese products. Cheese products may e.g. be selected from the group consisting of cream cheese, cottage cheese, and process cheese. By adding polypeptides the cheeses may contain significantly increased levels of galacto-oligosaccharides and reduced levels of lactose. In one aspect, the lactose levels in the final cheese product may be reduced by at least about 25 percent, preferably at least about 50 percent, and more preferably at least about 75 percent. The polypeptides may be used to reduce lactose in cheese products to less than about 1 gram per serving, an amount that can be tolerated by most lactose-intolerant individuals.

The cheese products provided herein are nutritionally-enhanced cheese products having increased soluble fiber content, reduced caloric content, excellent organoleptic properties, improved texture, and flavor. Further, the polypeptides described herein may reduce the glycemic index of the cheese products because GOS are more slowly absorbed than lactose or its hydrolysis products. Finally, the polypeptides may reduce the cost of production of cheese products, particularly cream cheese products, because GOS surprisingly provide improved texture to the cream cheese product, thus permitting reduced use of stabilizers, or by allowing for increased moisture content without syneresis.

In a further aspect, a composition comprising a polypeptide as described herein and a carbohydrate substrate, is provided. In a further aspect, the carbohydrate substrate is a disaccharide. In a further aspect, the disaccharide is for example lactulose, trehalose, rhamnose, maltose, sucrose, lactose or cellobiose. In yet a further aspect, the carbohydrate substrate is lactose. The composition is prepared such that oligosaccharides are produced. The polypeptide as described herein may be part of a product selected from the group consisting of yoghurt, cheese, fermented milk products, dietary supplements, and probiotic comestible products. In one aspect, a composition comprising a polypeptide as described herein and a stabilizer, is provided. Examples of stabilizers is e.g., a polyol such as, e.g., glycerol or propylene glycol, a sugar or a sugar alcohol, lactic acid, boric acid, or a boric acid derivative (e.g., an aromatic borate ester).

In one aspect, the use of a transgalactosylating polypeptide as disclosed herein or a cell as disclosed herein, for producing galacto-oligosaccharides, is provided. In one aspect, the use of a transgalactosylating polypeptide as disclosed herein or a cell as disclosed herein, for producing galacto-oligosaccharides to be part of a product selected from the group consisting of yoghurt, cheese, fermented dairy products, dietary supplements and probiotic comestible products, is provided. In one aspect, the product is yoghurt, cheese, or fermented dairy products. In one aspect, the use of a transgalactosylating polypeptide as disclosed herein or a cell as disclosed herein, for producing galacto-oligosaccharides to enhance the growth of *Bifidobacterium*, is provided. In one aspect, the use of a transgalactosylating polypeptide as disclosed herein or a cell as disclosed herein, for producing galacto-oligosaccharides to enhance the growth of *Bifidobacterium* in a mixed culture fermentation, is provided.

In one aspect, a process for producing a transgalactosylating polypeptide as disclosed herein, comprising culturing a cell as disclosed herein in a suitable culture medium under conditions permitting expression of said polypeptide, and recovering the resulting polypeptide from the culture, is provided. A process for producing galacto-oligosaccharides, comprising contacting of an polypeptide of as disclosed herein or a cell as disclosed herein with a milk-based solution comprising lactose, is provided.

Addition of oligosaccharides may enhance growth of either *Bifidobacterium* alone or of *Bifidobacterium* in a mixed culture.

The treatment of milk products with enzymes that converts lactose into monosaccharides or GOS have several advantages. First the products can be consumed by people with lactose intolerance that would otherwise exhibit symptoms such as flatulence and diarrhea. Secondly, dairy products treated with lactase will have a higher sweetness than similar untreated products due to the higher perceived sweetness of glucose and galactose compared to lactose. This effect is particularly interesting for applications such as yoghurt and ice-cream where high sweetness of the end product is desired and this allows for a net reduction of carbohydrates in the consumed product. Thirdly, in ice-cream production a phenomenon termed sandiness is often seen, where the lactose molecules crystallizes due to the relative low solubility of the lactose. When lactose is converted into monosaccharides or GOS the mouth feeling of the ice-cream is much improved over the non-treated products. The presence of a sandy feeling due to lactose crystallization can be eliminated and the raw material costs can be decreased by replacement of skimmed milk powder by whey powder. The main effects of the enzymatic treatment were increased sweetness.

In one aspect, the transgalactosylating polypeptide(s) as disclosed herein may be used together with other enzymes such as proteases such as chymosin or rennin, lipases such as phospholipases, amylases, transferases, and lactases. In one aspect, the transgalactosylating polypeptide(s) as disclosed herein may be used together with lactase. This may especially be useful when there is a desire to reduce residual lactose after treatment with the transgalactosylating polypeptide(s) as disclosed herein especially at low lactose levels. A lactase in the context of the present invention is any glycoside hydrolase having the ability to hydrolyse the disaccharide lactose into constituent galactose and glucose monomers. The group of lactases comprises but is not limited to enzymes assigned to subclass EC 3.2.1.108. Enzymes assigned to other subclasses, such as, e.g., EC 3.2.1.23, may also be lactases in the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity. Enzymes having lactase activity to be used in a method of the present invention may be of animal, of plant or of microbial origin. Preferred enzymes are obtained from microbial sources, in particular from a filamentous fungus or yeast, or from a bacterium. The enzyme may, e.g., be derived from a strain of *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium*, e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, B. stearothermophilus, B. thuringiensis*; *Bifidobacterium*, e.g. *B. longum, B. bifidum, B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes, E. cloacae Edwardsiella, E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus, Pycnoporus sanguineus*; *Ruminococcus*, e.g. *R. torques*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*. In one embodiment, the lactase is an intracellular component of microorganisms like *Kluyveromyces* and *Bacillus*. *Kluyveromyces*, especially *K. fragilis* and *K. lactis*, and other fungi such as those of the genera *Candida*, *Torula* and *Torulopsis*, are a common source of fungal lactases, whereas *B. coagulans* and *B. circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so called neutral lactases having a pH optimum between pH 6 and pH 8. When such lactases are used in the production of, e.g., low-lactose yoghurt, the enzyme treatment will either have to be done in a separate step before fermentation or rather high enzyme dosages have to be used, because their activity drop as the pH decreases during fermentation. Also, these lactases are not suitable for hydrolysis of lactose in milk performed at high temperature, which would in some cases be beneficial in order to keep the microbial count low and thus ensure good milk quality.

In one embodiment, the enzyme is a lactase from a bacterium, e.g. from the family Bifidobacteriaceae, such as from the genus *Bifidobacterium* such as the lactase described in WO 2009/071539.

Further Aspects of the Invention

Aspect 1. A polypeptide having transgalactosylating activity, which comprises an amino acid sequence having at least 90% sequence identity with SEQ ID NO: 1, and wherein said polypeptide, when being an expression product in a *Bacillus subtilis* strain BG3594 of a nucleic acid sequence, which encodes said polypeptide, is the only polypeptide expression product of said nucleic acid sequence that exhibits transgalactosylating activity.

Aspect 2. A polypeptide having transgalactosylating activity selected from the group consisting of:
  a. a polypeptide comprising an amino acid sequence having at least 90% sequence identity with SEQ ID NO: 1, wherein said polypeptide consists of at most 980 amino acid residues,
  b. a polypeptide comprising an amino acid sequence having at least 97% sequence identity with SEQ ID NO: 2, wherein said polypeptide consists of at most 975 amino acid residues,
  c. a polypeptide comprising an amino acid sequence having at least 96.5% sequence identity with SEQ ID NO: 3, wherein said polypeptide consists of at most 1300 amino acid residues,
  d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
  e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
  f. a polypeptide comprising a deletion, insertion and/or conservative substitution of one or more amino acid residues of SEQ ID NO: 1, 2, 3, 4 or 5.

Aspect 3. A polypeptide having transgalactosylating activity selected from the group consisting of:
  a. a polypeptide comprising an amino acid sequence having at least 90% sequence identity with SEQ ID NO: 1, wherein said polypeptide consists of at most 980 amino acid residues,
  b. a polypeptide comprising an amino acid sequence having at least 96.5% sequence identity with SEQ ID NO: 3, wherein said polypeptide consists of at most 1300 amino acid residues,
  c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i),
  d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and
  e. a polypeptide comprising a deletion, insertion and/or conservative substitution of one or more amino acid residues of SEQ ID NO: 1, 2, 3, 4 or 5.

Aspect 4. The polypeptide according to any one of the preceding aspects, wherein said polypeptide, when being an expression product in a *Bacillus subtilis* strain BG3594 of a nucleic acid sequence, which encodes said polypeptide, is the only polypeptide expression product of said nucleic acid sequence that exhibits transgalactosylating activity.

Aspect 5. The polypeptide according to any one of the preceding aspects comprising an amino acid sequence having at least 96.5% sequence identity with SEQ ID NO: 3, wherein said polypeptide consists of at most 1300 amino acid residues.

Aspect 6. The polypeptide according to any one of the preceding aspects comprising an amino acid sequence having at least 90% sequence identity with SEQ ID NO: 1, wherein said polypeptide consists of at most 980 amino acid residues.

Aspect 7. The polypeptide according to any of aspects 1, 2 and 4 comprising an amino acid sequence having at least 97% sequence identity with SEQ ID NO: 2, wherein said polypeptide consists of at most 975 amino acid residues.

Aspect 8. A polypeptide comprising an amino acid sequence having at least 90% sequence identity with SEQ ID NO: 1, wherein said polypeptide consists of at most 980 amino acid residues.

Aspect 9. The polypeptide according to aspect 8, wherein said polypeptide has transgalactosylating activity.

Aspect 10. The polypeptide according to any one of aspects 8-9, wherein said polypeptide, when being an expression product in a *Bacillus subtilis* strain BG3594 of a nucleic acid sequence, which encodes said polypeptide, is the only polypeptide expression product of said nucleic acid sequence that exhibits transgalactosylating activity.

Aspect 11. The polypeptide according to any one of the preceding aspects, wherein said sequence identity is at least 95%, such as, e.g. at least 96%, at least 97%, at least 98%, at least 99% or at least 100% sequence identity.

Aspect 12. A polypeptide wherein said polypeptide has at least 90% sequence identity with SEQ ID NO: 1.

Aspect 13. The polypeptide according to aspect 12, wherein said polypeptide has transgalactosylating activity.

Aspect 14. The polypeptide according to any one of the preceding aspects, wherein said polypeptide has at least 90% such as, e.g. at least 91%, at least 92%, at least 93%, at least 94%, at least 95%, at least 96%, at least 97%, at least 98%, or at least 99% sequence identity with SEQ ID NO: 1.

Aspect 15. The polypeptide according to any one of aspects 1-14, wherein the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the reference sequence.

Aspect 16. The polypeptide according to any one of aspects 1-15, wherein the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the longest of the two sequences.

Aspect 17. The polypeptide according to any one of aspects 1-16, wherein the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the "alignment length", where the alignment length is the length of the entire alignment including gaps and overhanging parts of the sequences.

Aspect 18. The polypeptide according to any one of aspects 15-17, wherein the suitable alignment program is a global alignment program.

Aspect 19. The polypeptide according to aspect 18, wherein the global alignment program uses the Needleman-Wunsch algorithm.

Aspect 20. The polypeptide according to any of aspects 18 and 19, wherein the global alignment program is selected from the group consisting of EMBOSS Needle and EMBOSS stretcher.

Aspect 21. The polypeptide according to any one of the preceding aspects, which consists of at most 975 amino acid residues, such as, e.g. at most 970 amino acid residues, such as at most 950 amino acid residues, such as at most 940 amino acid residues, at most 930 amino acid residues, at most 920 amino acid residues, at most 910 amino acid residues, at most 900 amino acid residues, at most 895 amino acid residues or at most 890 amino acid residues.

Aspect 22. The polypeptide according to any one of the preceding aspects, which consists of 887 amino acid residues.

Aspect 23. The polypeptide according to any one of the preceding aspects, which comprises SEQ ID NO:1.

Aspect 24. The polypeptide according to any one of the preceding aspects, which consist of the amino acid sequence of SEQ ID NO:1.

Aspect 25. The polypeptide according to any one of the preceding aspects, wherein said polypeptide consists of 965 amino acid residues.

Aspect 26. The polypeptide according to any of aspects 1-23 and 25, wherein said polypeptide has at least 96.5% sequence identity to SEQ ID NO: 2.

Aspect 27. The polypeptide according to any of aspects 1-23 and 25-26, wherein said polypeptide has at least 97%, such as, e.g. at least 98% or at least 99% sequence identity with SEQ ID NO: 2.

Aspect 28. The polypeptide according to any one of aspects 1-23 and 25-27, wherein said polypeptide comprises SEQ ID NO: 2.

Aspect 29. The polypeptide according to any one of aspects 1-23 and 25-28, wherein said polypeptide consists of the amino acid sequence of SEQ ID NO: 2.

Aspect 30. A polypeptide comprising an amino acid sequence having at least 96.5% sequence identity with SEQ ID NO: 3, wherein said polypeptide consists of at most 1300 amino acid residues.

Aspect 31. The polypeptide according to aspect 30, wherein said polypeptide has transgalactosylating activity.

Aspect 32. The polypeptide according to any one of aspects 30-31, wherein said polypeptide, when being an expression product in a *Bacillus subtilis* strain BG3594 of a nucleic acid sequence, which encodes said polypeptide, is the only polypeptide expression product of said nucleic acid sequence that exhibits transgalactosylating activity.

Aspect 33. The polypeptide according to any one of aspects 1-5, 15-20 and 30-32, wherein said sequence identity is at least 97%, such as, e.g. at least 98%, at least 99% or at least 100% sequence identity.

Aspect 34. The polypeptide according to any of aspects 1-5, 15-20 and 30-33, which comprises SEQ ID NO: 3.

Aspect 35. The polypeptide according to any one of aspects 11-5, 15-20 and 30-34, which consists of the amino acid sequence of SEQ ID NO: 3.

Aspect 36. The polypeptide according to any one of aspects 1-5, 15-20 and 30-34, which consists of at most 1290 amino acid residues, such as, e.g. at most 1280, at most 1270, at most 1260, at most 1250, at most 1240, at most 1230, at most 1220 or at most 1215 amino acid residues.

Aspect 37. The polypeptide according to any one of aspects 1-5, 15-20, 30-34 and 36, which consists of 1211 amino acid residues.

Aspect 38. The polypeptide according to any one of aspects 1-5, 15-20, 30-34 and 36-37, wherein said polypeptide has at least 98.5% sequence identity with SEQ ID NO: 5.

Aspect 39. The polypeptide according to any one of aspects 1-5, 15-20, 30-34 and 36-38, wherein said polypeptide has at least 99% or at least 99.5% sequence identity with SEQ ID NO: 5.

Aspect 40. The polypeptide according to any one of aspects 1-5, 15-20, 30-34 and 36-39, which comprises SEQ ID NO: 5.

Aspect 41. The polypeptide according to any one of aspects 1-5, 15-20, 30-34 and 36-40, which consists of the amino acid sequence of SEQ ID NO: 5.

Aspect 42. The polypeptide according to any one of aspects 1-5, 15-20, 30-34 and 36-40, which consists of at most 1210 amino acid residues, such as, e.g. at most 1200, at most 1190, at most 1180, at most 1170, at most 1160, at most 1150 or at most 1145 amino acid residues.

Aspect 43. The polypeptide according to any one of aspects 1-5, 15-20, 30-34, 36-40 and 42, which consists of 1142 amino acid residues.

Aspect 44. The polypeptide according to any one of aspects 1-5, 15-20, 30-34, 36-40 and 42-43, wherein said polypeptide has at least 96% sequence identity with SEQ ID NO: 4.

Aspect 45. The polypeptide according to any one of aspects 1-5, 15-20, 30-34, 36-40 and 42-44, wherein said polypeptide has at least 97%, such as, e.g., at least 98% or at least 99% sequence identity with SEQ ID NO: 4.

Aspect 46. The polypeptide according to any one of aspects 1-5, 15-20, 30-34, 36-40 and 42-45, which comprises SEQ ID NO: 4.

Aspect 47. The polypeptide according to any one of aspects 1-5, 15-20, 30-34, 36-40 and 42-46, which consists of the amino acid sequence of SEQ ID NO: 4.

Aspect 48. The polypeptide according to any one aspects 1-5, 15-20, 30-34, 36-40 and 42-46, which consists of at most 1130 amino acid residues, such as, e.g. at the most 1120, at the most 1110, at the most 1100, at the most 1090, at the most 1080, at the most 1070, at the most 1060, at the most 1050, at the most 1055 or at the most 1040 amino acid residues.

Aspect 49. The polypeptide according to any one of aspects 1-5, 15-20, 30-34, 36-40, 42-46 and 48, wherein said polypeptide consists of 1038 amino acid residues.

Aspect 50. The polypeptide according to any one of aspects 1-5, 15-20, 30-34, 36-40, 42-46 and 48-49, wherein said polypeptide has at least 96.5% sequence identity with SEQ ID NO: 3.

Aspect 51. The polypeptide according to any one of aspects 1-5, 15-20, 30-34, 36-40, 42-46 and 48-50, wherein said polypeptide has at least 97%, such as, e.g., at least 98% or at least 99% sequence identity with SEQ ID NO: 3.

Aspect 52. The polypeptide according to any one of aspects 1-5, 15-20, 30-34, 36-40, 42-46 and 48-51, which comprises SEQ ID NO:3.

Aspect 53. The polypeptide according to any one of aspects 1-5, 15-20, 30-34, 36-40, 42-46 and 48-52, which consists of the amino acid sequence of SEQ ID NO: 3.

Aspect 54. The polypeptide according to any of the preceding aspects, wherein the ratio of transgalactosylating activity:β-galactosidase activity is at least 0.5, such as at least 1, such as at least 1.5, such as at least 2 after 30 min. reaction such as above a concentration of 3% w/w initial lactose concentration.

Aspect 55. The polypeptide according to any one of the preceding aspects, wherein the ratio of transgalactosylating activity:β-galactosidase activity is at least 2.5, such as at least 3, such as at least 4, such as at least 5, such as at least 6, such as at least 7, such as at least 8, such as at least 9, such as at least 10, such as at least 11, or such as at least 12 after 30 min. reaction such as above a concentration of 3% w/w initial lactose concentration.

Aspect 56. The polypeptide according to any one of aspects 54-55, wherein the initial lactose concentration is 3% w/w.

Aspect 57. The polypeptide according to any one of the preceding aspects, which is isolated and/or purified.

Aspect 58. The polypeptide according to any one of the preceding aspects, which is recombinantly produced.

Aspect 59. The polypeptide according to any one of the preceding aspects, wherein said polypeptide has a ratio of transgalactosylation activity above 100%.

Aspect 60. The polypeptide according to any one of the preceding aspects, wherein said polypeptide has a ratio of transgalactosylation activity above 150%, 175% or 200%.

Aspect 61. The polypeptide according to any one of the preceding aspects, having a glycoside hydrolase catalytic core with an amino acid sequence selected from the group consisting of SEQ ID NO:7.

Aspect 62. The polypeptide according to any one of the preceding aspects containing a Glyco_hydro2N (PF02837), a Glyco_hydro (PF00703) and/or a Glyco_hydro 2C (PF02836) domains.

Aspect 63. The polypeptide according to any one of the preceding aspects containing the Bacterial Ig-like domain (group 4) (PF07532).

Aspect 64. The polypeptide according to any one of the preceding aspects, which is derived from *Bifidobacterium bifidum*.

Aspect 65. The polypeptide according to any one of the preceding aspects having a pH optimum of 6.5-7.5.

Aspect 66. The polypeptide according to any one of the preceding aspects having a temperature optimum of 30-60 such as 42-60 degree celcius.

Aspect 67. The polypeptide according to any one of the preceding aspects, wherein the percentage of identity of one amino acid sequence with, or to, another amino acid sequence is determined by the use of Blast with a word size of 3 and with BLOSUM 62 as the substitution matrix.

Aspect 68. The polypeptide according to any one of the preceding aspects, which polypeptide is a recombinant polypeptide.

Aspect 69. The polypeptide according to any one of the preceding aspects, which polypeptide is freeze-dried.

Aspect 70. The polypeptide according to any one of the preceding aspects, which polypeptide is in solution.

Aspect 71. The polypeptide according to any one of the preceding aspects, which polypeptide is isolated.

Aspect 72. The polypeptide according to any one of the preceding aspects, which polypeptide is purified.

Aspect 73. A nucleic acid capable of encoding a polypeptide according to any one of the preceding aspects.

Aspect 74. An expression vector comprising a nucleic acid according to aspect 73, or capable of expressing a polypeptide according to any one aspects 1-72.

Aspect 75. A cell capable of expressing a polypeptide according to any one of aspects 1-72.

Aspect 76. A method of expressing a polypeptide, the method comprising obtaining a cell according aspect 75 and expressing the polypeptide from the cell, and optionally purifying the polypeptide.

Aspect 77. A composition comprising a polypeptide as defined in any one of aspects 1-72, preferably a food composition, more preferably a dairy product.

Aspect 78. The composition according to aspect 77 comprising at least 5%, such as e.g. 10%, 15%, 20%, 25%, 30%, 35%, 40%, 45%, 50% w/w of one or more polypeptide(s) as defined in any one of aspects 1-72 based on the total amount of polypeptides in the composition having at least 70%, e.g. such as 72%, 74%, 74%, 78%, 80%, 82%, 84%, 86%, 88%, 90% sequence identity with SEQ ID NO: 22.

Aspect 79. The composition according to any one of aspects 77-78, wherein the one or more polypeptide(s) is selected from the group consisting of a polypeptide consisting of SEQ ID NO: 1, 2, 3, 4 and 5.

Aspect 80. The composition according to any one of aspects 77-79, wherein the one or more polypeptide(s) is selected from the group consisting of a polypeptide consisting of SEQ ID NO: 1, 2, and 3.

Aspect 81. The composition according to any one of aspects 77-80, wherein the one or more polypeptide(s) is a polypeptide consisting of SEQ ID NO: 1 or 2.

Aspect 82. A method for producing a food product by treating a substrate comprising lactose with a polypeptide as defined in any on of aspects 1-72.

Aspect 83. The method according to aspect 82 for producing a dairy product by treating a milk-based substrate comprising lactose with a polypeptide as defined in any one of aspects 1-72.

Aspect 84. The method according to any one of aspects 82-83 further treating the substrate with a hydrolysing beta-galactosidase.

Aspect 85. A galacto-oligosaccharide or composition thereof obtained by treating a substrate comprising lactose with a polypeptide as defined in any one of aspects 1-72.

Aspect 86. A nucleic acid capable of encoding a polypeptide according to any one of the aspects 1-72.

Aspect 87. The nucleic acid according to aspect 86 having a nucleic acid sequence which is at least 60% identical to SEQ ID NO: 9, 10, 11, 12 or 13.

Aspect 88. A plasmid comprising a nucleic acid according to any one of the aspects 86-87.

Aspect 89. An expression vector comprising a nucleic acid according to any one of the aspects 86-87, or capable of expressing a polypeptide according to any one of the aspects 1-72.

Aspect 90. A host cell comprising, preferably transformed with, a plasmid according to aspect 88 or an expression vector according to aspect 89.

Aspect 91. A cell capable of expressing a polypeptide according to any one of the aspects 1-72.

Aspect 92. The host cell according to aspect 90, or the cell according to aspect 91, which is a bacterial, fungal or yeast cell.

Aspect 93. The cell according to aspect 92, wherein the cell is selected from the group consisting of *Ruminococcus, Bifidobacterium, Lactococcus, Lactobacillus, Streptococcus, Leuconostoc, Escherichia, Bacillus, Streptomyces, Saccharomyces, Kluyveromyces, Candida, Torula, Torulopsis* and *Aspergillus*.

Aspect 94. The cell according to aspect 93, wherein the cell is selected from the group consisting of *Ruminococcus hansenii, Ruminococcus lactaris, Bifidobacterium breve, Bifidobacterium longum, Bifidobacterium infantis, Bifidobacterium bifidum* and *Lactococcus lactis*.

Aspect 95. A method of expressing a polypeptide, the method comprising obtaining a host cell or a cell according to any one of aspects 91-94 and expressing the polypeptide from the cell or host cell, and optionally purifying the polypeptide.

Aspect 96. A composition comprising a polypeptide as defined in any of aspects 1-72 and a stabilizer.

Aspect 97. A composition comprising a polypeptide as defined in any of aspects 1-72 and a carbohydrate substrate.

Aspect 98. The composition according to aspect 97, wherein the carbohydrate substrate is a disaccharide.

Aspect 99. The composition according to aspect 98, wherein the disaccharide is lactose.

Aspect 100. A method for producing a dairy product by treating a milk-based substrate comprising lactose with a polypeptide according to any one of aspects 1-72.

Aspect 101. The method according to aspect 90, wherein the polypeptide has a ratio of transgalactosylation activity as defined above.

Aspect 102. The method according to any one of aspects 100-101, wherein the milk-based substrate is yoghurt, cheese, or fermented dairy products.

Aspect 103. The method according to any one of aspects 100-102, further comprising fermenting said substrate with a microorganism capable of fermenting said substrate.

Aspect 104. The method according to aspect 103, wherein the milk-based substrate is yogurt.

Aspect 105. The method according to any one of aspects 100-104, wherein the treatment with the polypeptide and the microorganism is performed essentially at the same time.

Aspect 106. The method according to any one of aspects 100-105, wherein the polypeptide and the microorganism are added to the milk-based substrate essentially at the same time.

Aspect 107. Use of a cell of any of above aspects for producing a product selected from the group consisting of yoghurt, cheese, fermented milk product, dietary supplement and probiotic comestible product.

Aspect 108. A dairy product comprising a cell of any of above aspects.

Aspect 109. A dairy product comprising a polypeptide as defined in any one of aspects 1-72.

Aspect 110. A dairy product comprising a polypeptide as defined in any one of aspects 1-72 in a concentration of 0.01-1000 ppm.

Aspect 111. A dairy product comprising an inactivated polypeptide as defined in any one of aspects 1-72.

Aspect 112. A dairy product comprising an inactivated polypeptide as defined in any one of aspects 1-72 in a concentration of 0.01-1000 ppm.

Aspect 113. A dairy product comprising GOS formed in situ by a polypeptide as defined in any one of aspects 1-72.

Aspect 114. Use of a transgalactosylating polypeptide of any one of aspects 1-72 or a cell of any one of above aspects, for producing galacto-oligosaccharides.

Aspect 115. Use of a transgalactosylating polypeptide of any one of aspects 1-72 or a cell of any one of above aspects, for producing galacto-oligosaccharides to be part of a product selected from the group consisting of yoghurt, cheese, fermented dairy products, dietary supplements and probiotic comestible products.

Aspect 116. Use of a transgalactosylating polypeptide of any one of aspects 1-72 or a cell of any one of above aspects, for producing galacto-oligosaccharides to enhance the growth of *Bifidobacterium*.

Aspect 117. Use of a transgalactosylating polypeptide of any one of aspects 1-72 or a cell of any one of above aspects, for producing galacto-oligosaccharides to enhance the growth of *Bifidobacterium* in a mixed culture fermentation.

Aspect 118. A process for producing a transgalactosylating polypeptide of any one of aspects 1-72, comprising culturing a cell of any one of above aspects in a suitable culture medium under conditions permitting expression of said polypeptide, and recovering the resulting polypeptide from the culture.

Aspect 119. A process for producing galacto-oligosaccharides, comprising contacting of an polypeptide of any one of aspects 1-72 or a cell of any one of above aspects with a milk-based solution comprising lactose.

Aspect 120. A polypeptide which is a C-terminal truncated fragment of SEQ ID NO:22 having transgalactosylating activity and which are stable against further truncation such as by proteolytic degradation when produced in a suitable organism such as *Bacillus subtilis* e.g. *Bacillus subtilis* strain BG3594 and/or which are stable against further truncation during storage after final formulation.

Aspect 121. The polypeptide according to aspect 120 which is as further defined in any one of aspects 1-72.

Materials and Methods

Method 1

Production of Polypeptide

Synthetic genes designed to encode the *Bifidobacterium bifidum* full length (1752 residues) gene with codons optimised for expression in *Bacillus subtilis* were purchased from GeneART (Regensburg, Germany) SEQ ID No. 8

The *Bifidobacterium bifidum* truncation mutants were constructed using polymerase chain reaction with reverse primers that allowed specific amplification of the selected region of the synthetic gene.

Forward primer: GGGGTA<u>ACTAGT</u>GGAAGATGCAACAAGAAG
(SpeI underlined). (SEQ ID NO: 15) Reverse primers:

| Truncation mutant | Primer sequence |
|---|---|
| BIF917 (SEQ ID NO: 9) | GCGCTTAATTAATTATGTTTTTCTGTGCTTGTTC SEQ ID NO: 16 |
| BIF995 (SEQ ID NO: 10) | GCGCTTAATTAATTACAGTGCGCCAATTTCATCAATCA SEQ ID NO: 17 |
| BIF1068 (SEQ ID NO: 11) | GCGCTTAATTAATTATTGAACTCTAATTGTCGCTG SEQ ID NO: 18 |
| BIF1241 (SEQ ID NO: 12) | GCGCTTAATTAATTATGTCGCTGTTTTCAGTTCAAT SEQ ID NO: 19 |
| BIF1326 (SEQ ID NO: 13) | GCGCTTAATTAATTAAAATTCTTGTTCTGTGCCCA SEQ ID NO: 20 |
| BIF1478 (SEQ ID NO: 14) | GCGCTTAATTAATTATCTCAGTCTAATTTCGCTTGCGC SEQ ID NO: 21 |

Figure 1:
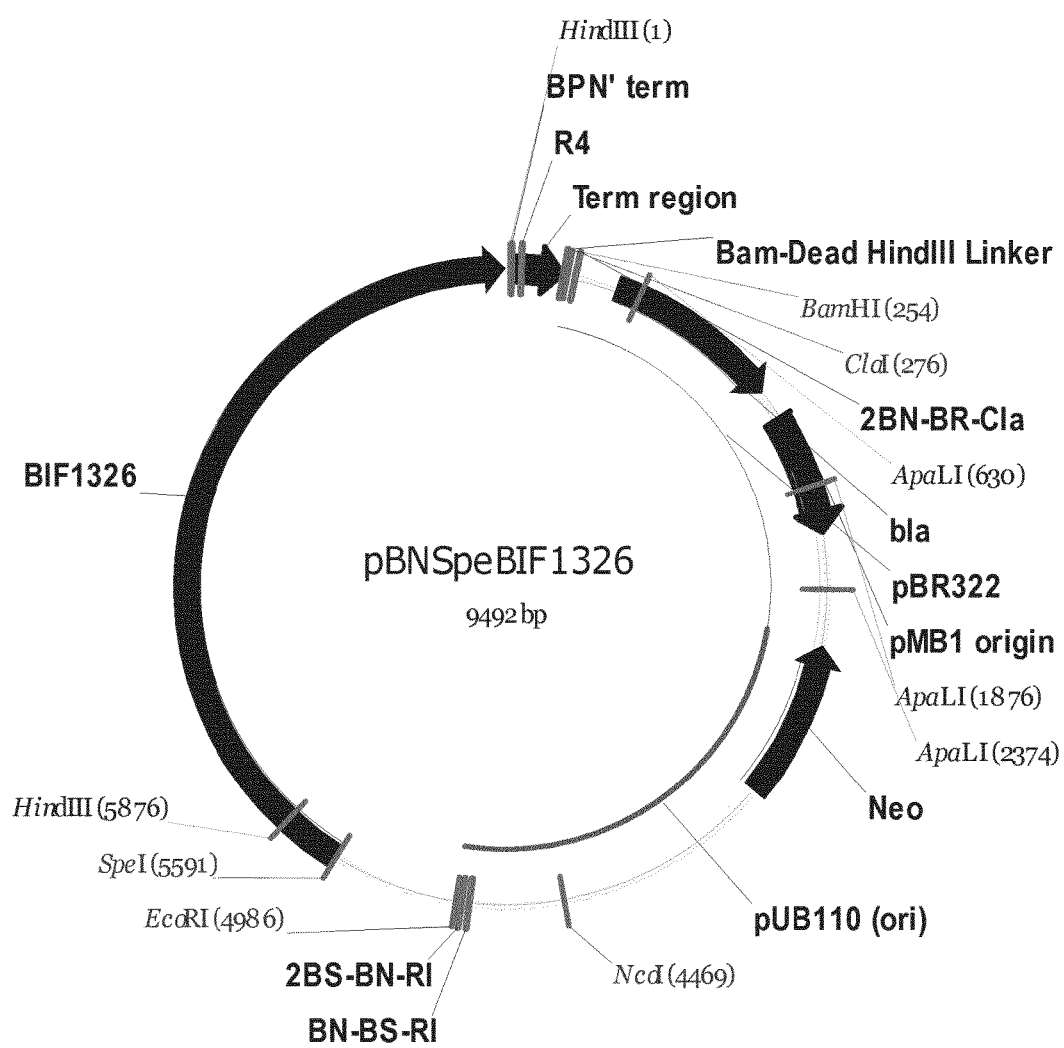
FIG. 1 shows a plasmid map for the BIF_1326 variant for recombinant expression in *Bacillus subtilis*.

The synthetic gene was cloned into the pBNspe *Bacillus subtilis* expression vector using the unique restriction sites SpeI and PacI (FIG. 1) and the isolated plasmids were transformed into the *Bacillus subtilis* strain BG3594. Transformants were restreaked onto LB plates containing 10 µg/mL Neomycin as selection.

A preculture was setup in LB media containing 10 µg/mL Neomycin and cultivated for 7 hours at 37° C. and 180 rpm shaking. 500 µL of this preculture was used to inoculate 50 mL Grant's modified medium containing 10 µg/mL Neomycin at allowed to grow for 68 hours at 33° C. and 180 rpm shaking.

Cells were lysed by addition directly to the culture media of 1 mg/ml Lysozyme (Sigma-Aldrich) and 10 U/ml Benzonase (Merck) final concentrations and incubated for 1 hr at 33° C. at 180 RPM. Lysates were cleared by centrifugation at 10.000×g for 20 minutes and subsequently sterile filtered.

Grant's Modified Media was Prepared According to the Following Directions:

| PART I (Autoclave) | |
|---|---|
| Soytone | 10 g |
| Bring to | 500 mL per liter |
| PART II | |
| 1M $K_2HPO_4$ | 3 mL |
| Glucose | 75 g |
| Urea | 3.6 g |
| Grant's 10X MOPS | 100 mL |
| Bring to | 400 mL per liter |

PART I (2 w/w % Soytone) was prepared, and autoclaved for 25 minutes at 121° C.

PART II was prepared, and mixed with PART 1 and pH was adjusted to pH to 7.3 with HCl/NaOH.

The volume was brought to full volume and sterilized through 0.22-µm PES filter.

10×MOPS Buffer was Prepared According to the Following Directions:

| | | |
|---|---|---|
| 83.72 g | Tricine | |
| 7.17 g | KOH Pellets | |
| 12 g | NaCl | |
| 29.22 g | 0.276M K2SO4 | |
| 10 mL | 0.528M MgCl2 | |
| 10 mL | Grant's Micronutrients 100X | |

Bring to app. 900 mL with water and dissolve. Adjust pH to 7.4 with KOH, fill up to 1 L and sterile filter the solution through 0.2 µm PES filter.

100× Micronutrients was Prepared According to the Following Directions:

| | |
|---|---|
| Sodium Citrate•2H2O | 1.47 g |
| CaCl2•2H2O | 1.47 g |
| FeSO4•7H2O | 0.4 g |
| MnSO4•H2O | 0.1 g |
| ZnSO4•H2O | 0.1 g |
| CuCl2•2H2O | 0.05 g |
| CoCl2•6H2O | 0.1 g |
| Na2MoO4•2H2O | 0.1 g |

Dissolve and adjust volume to 1 L with water.
Sterilization was through 0.2 µm PES filter.
Storing was at 4° C. avoid light.

Method 2
Purification and Enzyme Preparations

The filtrated enzyme isolate was concentrated using a VivaSpin ultra filtration device with a 10 kDa MW cut off (Vivaspin 20, Sartorius, Lot#12VS2004) and the concentrate was loaded onto a PD10 desalting column (GE healthcare, Lot#6284601) and eluted in 20 mM Tris-HCl pH 8.6. Chromatography was carried out manually on an Äkta FPLC system (GE Healthcare). 4 mL of the desalted sample, containing approximately 20 mg protein, was loaded onto a 2 mL HyperQ column (HyperCel™, Q sorbent) equilibrated with 20 mM Tris-HCl pH 8.6 at a flowrate of 1 ml/min. The column was thoroughly washed with 30 CV (column volumes) wash buffer and the bound β-galactosidase was eluted with a 100CV long gradient into 20 mM Tris-HCl pH 8.6 250 mM NaCl. Remaining impurities on the column were removed with a one-step elution using 20 mM Tris-HCl pH 8.6 500 mM NaCl. Protein in the flow through and elution was analyzed for β-galactosidase activity and by SDS-page.

Figure 2:
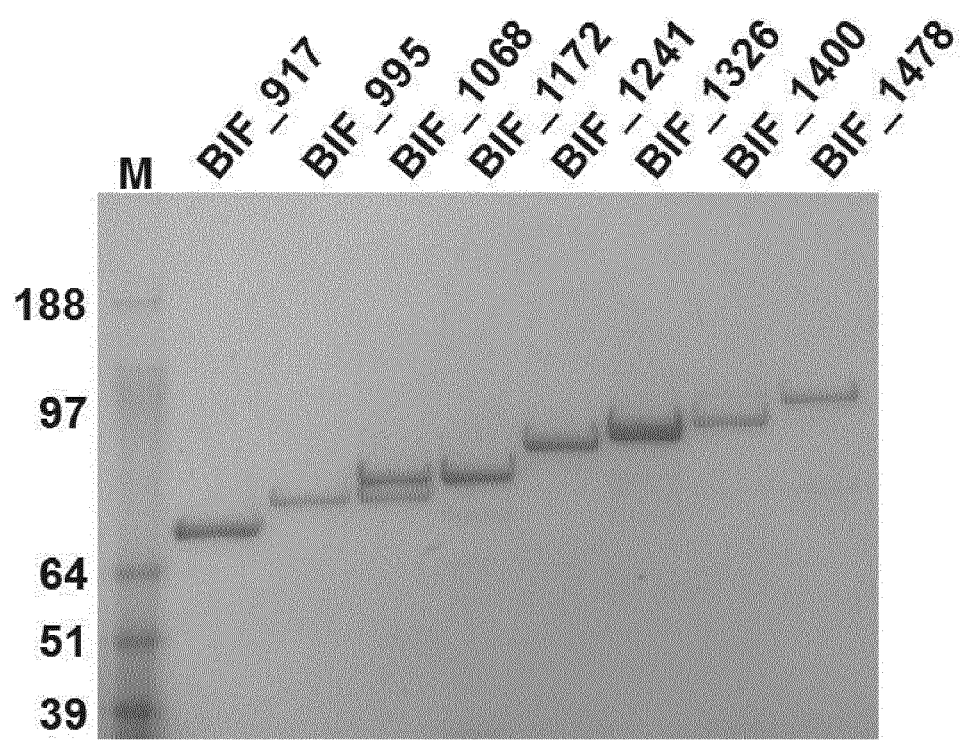
FIG. 2 shows SDS-PAGE showing truncation variants purified using HyperQ column eluted with a NaCl gradient.

SDS-page gels were run with the Invitrogen NuPage® Novex 4-12% Bis-Tris gel 1.0 mm, 10 well (Cat#NP0321box), See-Blue® Plus2 prestained Standard (Cat# LC5925) and NuPAGE® MES SDS Running Buffer (Cat# NP0002) according to the manufacturer's protocol. Gels were stained with Simply Blue Safestain (Invitrogen, Cat# LC6060) (FIG. 2).

Method 3
Measuring β-Galactosidase Activity

Enzymatic activity was measured using the commercially available substrate 2-Nitrophenyl-β-D-Galactopyranoside (ONPG) (Sigma N1127).

| ONPG w/o acceptor |
|---|
| 100 mM KPO4 pH 6.0 |
| 12.3 mM ONPG |

| ONPG supplemented with acceptor |
|---|
| 100 mM KPO4 pH 6.0 |
| 20 mM Cellobiose |
| 12.3 mM ONPG |
| STOP Solution |

| |
|---|
| 10% Na2CO3 |

10 µl dilution series of purified enzyme was added in wells of a microtiter plates containing 90 µl ONPG-buffer with or without acceptor. Samples were mixed and incubated for 10 min at 37° C., subsequently 100 µl STOP Solution were added to each well to terminate reaction. Absorbance measurements were recorded at 420 nm on a Molecular Device SpectraMax platereader controlled by the Softmax software package.

The ratio of transgalactosylation activity was calculated as follows $$\text{Ratio of transgalctosylation activity} = (Abs420^{+Cellobiose}/Abs420^{-Cellobiose})*100,$$

for dilutions where the absorbance was between 0.5 and 1.0 (FIG. 3).

Method 4
Determination of LAU Activity
Principle:

The principle of this assay method is that lactase hydrolyzes 2-o-nitrophenyl-β-D-galactopyranoside (ONPG) into 2-o-nitrophenol (ONP) and galactose at 37° C. The reaction is stopped with the sodium carbonate and the liberated ONP is measured in spectrophotometer or colorimeter at 420 nm.

Reagents:

MES buffer pH 6.4 (100 mM MES pH 6.4, 10 mM $CaCl_2$): Dissolve 19.52 g MES hydrate (Mw: 195.2 g/mol, Sigma-aldrich #M8250-250G) and 1.470 g $CaCl_2$ di-hydrate (Mw: 147.01 g/mol, Sigma-aldrich) in 1000 ml dd$H_2O$, adjust pH to 6.4 by 10M NaOH. Filter the solution through 0.2 µm filter and store at 4° C. up to 1 month.

ONPG substrate pH 6.4 (12.28 mM ONPG, 100 mM MES pH 6.4, 10 mM $CaCl_2$): Dissolve 0.370 g 2-o-nitrophenyl-β-D-galactopyranoside (ONPG, Mw: 301.55 g/mol, Sigma-aldrich #N1127) in 100 ml MES buffer pH 6.4 and store dark at 4° C. for up to 7 days.

Stop reagent (10% $Na_2CO_3$): Dissolve 20.0 g $Na_2CO_3$ in 200 ml dd$H_2O$, Filter the solution through 0.2 µm filter and store at RT up to 1 month.

Procedure:

Dilution series of the enzyme sample was made in the MES buffer pH 6.4 and 10 µL of each sample dilution were transferred to the wells of a microtiter plate (96 well format) containing 90 µl ONPG substrate pH 6.4. The samples were mixed and incubated for 5 min at 37° C. using a Thermomixer (Comfort Thermomixer, Eppendorf) and subsequently 100 µl Stop reagent was added to each well to terminate the reaction. A blank was constructed using MES buffer pH 6.4 instead of the enzyme sample. The increase in absorbance at 420 nm was measured at a ELISA reader (SpectraMax platereader, Molecular Device) against the blank.

Calculation of Enzyme Activity:

The molar extinction coefficient of 2-o-nitrophenol (Sigma-aldrich #33444-25G) in MES buffer pH 6.4 was determined $(0.5998 \times 10^{-6} M^{-1} \times cm^{-1})$. One unit (U) of lactase activity (LAU) was defined as that corresponding to the hydrolysis of 1 nmol of ONPG per minute. Using microtitre plates with a total reaction volume of 200 µL (light path of 0.52 cm) the lactase activity per mL of the enzyme sample may be calculated using the following equation:

$$LAU/ml\left(\frac{nmol}{min \cdot mL}\right) = \frac{Abs_{420} \times 200\, \mu L \times \text{dilution factor}}{0.5998 \cdot 10^3 \cdot nM^{-1} \cdot cm^{-1} \times 0.52\ cm \times 5\ min \times 0.01\ mL}$$

Calculation of Specific Activity for BIF917 Shown Herein as SEQ ID NO: 1:
Determination of BIF917 Concentration:

Quantification of the target enzyme (BIF917) and truncation products were determined using the Criterion Stain free SDS-page system (BioRad). Any kD Stain free precast Gel 4-20% Tris-HCl, 18 well (Comb #345-0418) was used with a Serva Tris-Glycine/SDS buffer (BioRad cat. #42529). Gels were run with the following parameters: 200 V, 120 mA, 25 W, 50 min. BSA (1.43 mg/ml) (Sigma-Aldrich, cat. #500-0007) was used as protein standard and Criterion Stain Free Imager (BioRad) was used with Image Lab software (BioRad) for quantification using band intensity with correlation of the tryptophan content.

The specific LAU activity of BIF917 was determined from crude ferment (ultra filtration concentrate) of two independent fermentations (as described in method 1) and using 5 different dilutions (see table 1).

The specific activity of BIF917 was found to be 21.3 LAU/mg or 0.0213 LAU/ppm.

from the measured β-galactosidase activity for each variant and is shown in FIG. 3. Variants having a length of 1241 residues or less shows a ratio of transgalactosylation activity above 100%, indicating that these variants are predominantly transgalactosylating. The variants with a length that is more that 1241 residues shows a ratio of transgalactosylation activity below 100%, indicating that these variants are predominantly hydrolytic. BIF_917 and BIF_995 have the highest ratio of transgalactosylation activity around 250%.

Example 2

GOS Generated in a Yoghurt Matrix

Evaluation of BIF enzymes in GOS production were tested in an yogurt application mimic. Batch experiments with a volume of 100 μl were performed in 96 well MTP plates using a yogurt mix, consisting of 98.60% (w/v) fresh pasteurized low-fat milk (Mini-mælk, Arla Foods, Denmark) and 1.4% (w/v) Nutrilac YQ-5075 whey ingredient (Arla). To completely hydrate Nutrilac YQ-5075 the mixture was left with agitation for 20 h and afterwards added 20 mM NaPhosphate pH 6.5 to ensure a pH of 6.5. This milk-base was used plain and the lactose concentration was determined to be 5.5% (w/v), corresponding to 5.3% (w/w) in this solution. The following correlation is valid in the present example: 1% (w/v) lactose=0.9587% (w/w) lactose. 90 μl of the milk-base was mixed with 10 μl of the purified enzymes, sealed with tape and incubated at 43° C. for 3 hours. The reaction was stopped by 100 μl 10% $Na_2CO_3$. Samples stored at −20° C.

TABLE 1

Determination of BIF917 specific activity

| Sample ID | Enzyme | Fermentation | Dilution factor | Activity LAU/ml | Protein (BIF917) concentration mg/ml | Protein (BIF917) concentration ppm | Specific activity LAU/mg | Specific activity LAU/ppm |
|---|---|---|---|---|---|---|---|---|
| 1 | BIF 917 | a | 5 | 26.9 | 1.23 | 1232 | 21.9 | 0.0219 |
| 2 | BIF 917 | a | 10 | 53.9 | 2.44 | 2437 | 22.1 | 0.0221 |
| 3 | BIF 917 | a | 10 | 75.4 | 3.56 | 3556 | 21.2 | 0.0212 |
| 4 | BIF 917 | a | 20 | 163.9 | 7.78 | 7778 | 21.1 | 0.0211 |
| 5 | BIF 917 | a | 30 | 233.6 | 11.06 | 11065 | 21.1 | 0.0211 |
| 6 | BIF 917 | b | 5 | 30.26825 | 1.34 | 1342 | 22.6 | 0.0226 |
| 7 | BIF 917 | b | 10 | 55.91536 | 2.61 | 2607 | 21.4 | 0.0214 |
| 8 | BIF 917 | b | 10 | 76.96056 | 3.70 | 3697 | 20.8 | 0.0208 |
| 9 | BIF 917 | b | 20 | 156.986 | 7.75 | 7755 | 20.2 | 0.0202 |
| 10 | BIF 917 | b | 30 | 236.9734 | 11.45 | 11452 | 20.7 | 0.0207 |
| | | | | | | Arg | 21.3 | 0.0213 |
| | | | | | | Std | 0.700976 | 0.000701 |

EXAMPLES

Example 1

Determining β-Galactosidase Activity of BIF Truncation Variants

Eight different truncation variants: BIF_917, BIF_995, BIF_1068, BIF_1172, BIF_1241, BIF1326, BIF_1400 and BIF_1478 were constructed as described using method 1 and purified as described in method 2 (see FIG. 2).

The β-galactosidase activity was determined of all truncation variants in presence and absence of cellobiose using the described method 3 above.
Results The ratio of transgalactosylation activity (($Abs420^{+Cellobiose}$/$Abs420^{-Cellobiose}$)*100) was calculated HPLC Method Quantification of galactooligosaccharides (GOS), lactose, glucose and galactose were performed by HPLC. Analysis of samples was carried out on a Dionex ICS 3000. IC parameters were as follows: Mobile phase: 150 mM NaOH, Flow: Isochratic, 0.25 ml/min, Column: Carbopac PA1, Column temperature: RT, Injection volume: 10 μL, Detector: PAD, Integration: Manual, Sample preparation: 100 times dilution in Milli-Q water (0.1 ml sample+9.9 ml water) and filtration through 0.45 im syringe filters, Quantification: Peak areas in percent of peak area of the standard. A GOS syrup (Vivanal GOS, Friesland Campina) was used as standard for GOS quantification. In this example, the term "GOS" is defined as galactooligosaccharides with a degree of polymerization (DP) of 3 or above.

Results

The quantified amount of GOS generated in the milk-base by BIF_917, BIF_995 and BIF_1326 is shown in FIG. 4. It can be see that the shorter variants BIF_917 and BIF_995 have a significantly (determined by a students T-test with 95% confidence) higher GOS production around 1.2% (w/v) compared to BIF_1326 generating below 0.1% (w/v).

Example 3

Degradation Pattern of Truncation Variants

A library covering the region between BIF1230 and BIF1325 was ordered from GeneART (Regensburg, Germany) (see table 2). The truncation variants was produced as described in method 1. The resulting peptides were subjected to SDS_PAGE analysis and visualized with Simply Blue Safestain (Invitrogen, Cat# LC6060) (FIG. 5).

Results

Surprisingly, most of the variants were proteolytically modified in the final broth with varying amounts of target band appearing at the end of fermentation. The variants generated three distinct bands with varying intensities which was verified using mass spectrometry. The variants have C-terminal truncation with BIF917 corresponding to the termini of SEQ ID NO: 1, BIF995 corresponding to the termini of SEQ ID NO: 2 and BIF1068 corresponding to the termini of SEQ ID NO: 3.

The protein bands cut from the gel (marked with arrows in FIG. 5) are digested using three different enzymes, as preparation for mass spectrometry analysis. Trypsin hydrolyzes peptide bonds specifically at the carboxyl side of arginine (R) and lysine (K) residues except when a proline (P) is on the carboxyl side. α-Chymotrypsin hydrolyzes peptide bonds specifically at the carboxyl side of tyrosine (Y), phenylalanine (F), tryptophan (W) and leucine (L) except when a proline (P) is on the carboxyl side. Glu-C preferentially cleaves at the carboxyl side of glutamyl (E) in ammonium bicarbonate buffer pH 8, but also cleaves at the carboxyl side of aspartyl (D) if the hydrolysis is carried out in a phosphate buffer pH 8.

In order to detect the C-terminal, the protein of interest is prepared for analysis using our basic procedure for protein characterisation (A2963), with one change using 40% $^{18}$O-water in the digestion buffer. The theory is that the proteolytic cleavage will incorporate both $^{18}$O-water and $^{16}$O-water in the resulting peptides, which consequently will appear as doublets. The protein C-terminal though will only appear as a single peptide with $^{16}$O-water, since it is not cleaved but just the "last peptide" left of the protein. In this way the C-terminal is mapped using MS/MS analysis.

TABLE 2

| Variants | | |
|---|---|---|
| Name | Fragment of SEQ ID NO: 6 | WELL |
| BIF1230 | 1 | 1201 | A01 |
| BIF1231 | 1 | 1202 | B01 |
| BIF1232 | 1 | 1203 | C01 |
| BIF1233 | 1 | 1204 | |
| BIF1234 | 1 | 1205 | |
| BIF1235 | 1 | 1206 | D01 |
| BIF1236 | 1 | 1207 | |
| BIF1237 | 1 | 1208 | E01 |
| BIF1238 | 1 | 1209 | F01 |
| BIF1239 | 1 | 1210 | G01 |
| BIF1240 | 1 | 1211 | A02 |
| BIF1241 | 1 | 1212 | B02 |
| BIF1242 | 1 | 1213 | C02 |
| BIF1243 | 1 | 1214 | |
| BIF1244 | 1 | 1215 | E02 |
| BIF1245 | 1 | 1216 | F02 |
| BIF1246 | 1 | 1217 | G02 |
| BIF1247 | 1 | 1218 | H02 |
| BIF1248 | 1 | 1219 | A03 |
| BIF1249 | 1 | 1220 | B03 |
| BIF1250 | 1 | 1221 | C03 |
| BIF1251 | 1 | 1222 | D03 |
| BIF1252 | 1 | 1223 | E03 |
| BIF1253 | 1 | 1224 | |
| BIF1254 | 1 | 1225 | F03 |
| BIF1255 | 1 | 1226 | G03 |
| BIF1256 | 1 | 1227 | H03 |
| BIF1257 | 1 | 1228 | A04 |
| BIF1258 | 1 | 1229 | B04 |
| BIF1259 | 1 | 1230 | C04 |
| BIF1260 | 1 | 1231 | D04 |
| BIF1261 | 1 | 1232 | |
| BIF1262 | 1 | 1233 | E04 |
| BIF1263 | 1 | 1234 | F04 |
| BIF1264 | 1 | 1235 | G04 |
| BIF1265 | 1 | 1236 | H04 |
| BIF1266 | 1 | 1237 | A05 |
| BIF1267 | 1 | 1238 | B05 |
| BIF1268 | 1 | 1239 | C05 |
| BIF1269 | 1 | 1240 | D05 |
| BIF1270 | 1 | 1241 | E05 |
| BIF1271 | 1 | 1242 | F05 |
| BIF1272 | 1 | 1243 | G05 |
| BIF1273 | 1 | 1244 | H05 |
| BIF1274 | 1 | 1245 | A06 |
| BIF1275 | 1 | 1246 | B06 |
| BIF1276 | 1 | 1247 | C06 |
| BIF1277 | 1 | 1248 | D06 |
| BIF1278 | 1 | 1249 | E06 |
| BIF1279 | 1 | 1250 | |
| BIF1280 | 1 | 1251 | F06 |
| BIF1281 | 1 | 1252 | G06 |
| BIF1282 | 1 | 1253 | H06 |
| BIF1283 | 1 | 1254 | A07 |
| BIF1284 | 1 | 1255 | |
| BIF1285 | 1 | 1256 | |
| BIF1286 | 1 | 1257 | |
| BIF1287 | 1 | 1258 | B07 |
| BIF1288 | 1 | 1259 | |
| BIF1289 | 1 | 1260 | C07 |
| BIF1290 | 1 | 1261 | D07 |
| BIF1291 | 1 | 1262 | |
| BIF1292 | 1 | 1263 | E07 |
| BIF1293 | 1 | 1264 | |
| BIF1294 | 1 | 1265 | |
| BIF1295 | 1 | 1266 | F07 |
| BIF1296 | 1 | 1267 | G07 |
| BIF1297 | 1 | 1268 | |
| BIF1298 | 1 | 1269 | H07 |
| BIF1299 | 1 | 1270 | A08 |
| BIF1300 | 1 | 1271 | B08 |
| BIF1301 | 1 | 1272 | C08 |
| BIF1302 | 1 | 1273 | D08 |
| BIF1303 | 1 | 1274 | E08 |
| BIF1304 | 1 | 1275 | F08 |
| BIF1305 | 1 | 1276 | G08 |
| BIF1306 | 1 | 1277 | H08 |
| BIF1307 | 1 | 1278 | A09 |
| BIF1308 | 1 | 1279 | B09 |
| BIF1309 | 1 | 1280 | |
| BIF1310 | 1 | 1281 | |
| BIF1311 | 1 | 1282 | |
| BIF1312 | 1 | 1283 | C09 |
| BIF1313 | 1 | 1284 | |
| BIF1314 | 1 | 1285 | |
| BIF1315 | 1 | 1286 | D09 |
| BIF1316 | 1 | 1287 | E09 |

TABLE 2-continued

| Variants | | |
|---|---|---|
| Name | Fragment of SEQ ID NO: 6 | WELL |
| BIF1317 | 1 | 1288 | F09 |
| BIF1318 | 1 | 1289 | G09 |
| BIF1319 | 1 | 1290 | H09 |
| BIF1320 | 1 | 1291 | A10 |
| BIF1321 | 1 | 1292 | B10 |
| BIF1322 | 1 | 1293 | C10 |
| BIF1323 | 1 | 1294 | D10 |
| BIF1324 | 1 | 1295 | E10 |
| BIF1325 | 1 | 1296 | F10 |

Example 4

GOS Generated Enzymatically In Situ in Milkbase and Yoghurts

In this example, the term "GOS" is defined as galactooligosaccharides with a degree of polymerization (DP) of 3 or above.

Evaluation of GOS production by BIF917 and BIF995 were tested by in situ application in different set-style yogurts. The β-glactosidase was added to the milk-base simultaneous with addition of the specific yoghurt cultures, resulting in the transgalactosylation reaction running together with the yoghurt fermentation process.

Initial yoghurt (set-style) batch experiments were made with a 100 mL milkbase (yoghurt mix). The milkbase consisted of 98.60% (w/v) fresh pasteurized conventional (not-organic) low-fat milk (Mini-mælk 0.5% fat, Arla Foods Amba, Denmark) and 1.4% (w/v) Nutrilac YQ-5075 whey ingredient (Arla Foods Ingredients, Denmark), resulting in a lactose concentration of 5.5% (w/v) corresponding to 5.3% (w/w) (1% (w/v) lactose=0.9587% (w/w) lactose in this solution). To completely hydrate Nutrilac YQ-5075 the mixture was left with weak agitation for 20 hr at 4° C. in the initial experiment a freeze-dried YO-MIX 485LYO culture was used consisting of Lactobacillus delbrüeckii subsp bulgaricus and Streptococcus thermophilus (DuPont Nutrition Biosciences, Denmark). An initial dilution of the culture was made, adding 10 g of YO-MIX 485LYO to 400 mL UHT conventional (not-organic) milk (Let-mælk 1.5% fat, Arla Foods Amba, Denmark). 1.43 mL of the diluted culture was added per liter of milk-base. 100 mL milkbase were distributed in 250 mL bluecap bottles and enzymes were added in varying concentration (10, 20 and 40 ppm, corresponding to 0.213, 0.426 and 0.853 LAU as described in method 4) constitution 1% (v/v) of the final yogurt-mix. Yoghurt fermentation was performed at 43° C. and ended after 10 hr by fast cooling on ice. Fermentations were always run in duplicates and yoghurt sugar/oligosaccharide composition was analyzed by HPLC on the day after fermentation (see HPLC method below). Fermented yoghurt samples were always stored at 4° C.

The results of the initial yoghurt experiment are shown in table 3. It can be seen that increased dose of either BIF917 or BIF995 from 10 ppm to 40 ppm lead to increased GOS content and decreased amount of DP2 (including lactose) in the final yoghurt. The difference in performance of the two variants is within the variance of the HPLC determination and it may be concluded that they perform similar within the investigated dosages.

TABLE 3

Content of DP2 saccharides (mainly lactose) and GOS (DP3+) in a fermented yogurt treated with increasing dose of BIF917 and BID995. All results are calculated as an average of three independent measurements.

| | | Amount w/v % DP2 incl. Lactose | Std | Amount w/v % GOS (DP3+) | Std |
|---|---|---|---|---|---|
| Yogurt | BIF917_10 ppm | 2.191 | 0.092 | 1.249 | 0.051 |
| | BIF917_20 ppm | 1.296 | 0.047 | 1.882 | 0.056 |
| | BIF917_40 ppm | 0.970 | 0.019 | 2.346 | 0.047 |
| | BIF995_10 ppm | 2.787 | 0.139 | 1.158 | 0.035 |
| | BIF995_20 ppm | 1.494 | 0.075 | 1.649 | 0.082 |
| | BIF995_40 ppm | 0.931 | 0.028 | 2.392 | 0.063 |
| | H20 | 4.219 | 0.127 | 0.000 | 0.000 |
| Milkbase | | 5.500 | 0.156 | 0.000 | 0.000 |

Set-style yoghurt was made with higher initial lactose concentration of 7.5% w/v (corresponding to 7.1% w/w, as 1% w/v lactose=0.9423% w/w in this solution) to investigate its effect on the GOS concentration achieved in the final yoghurt. The following procedure was applied:
1. All powder ingredients (listed in table 4) are mixed and the dry blend are added to the milk/water under good agitation at 4-5° C., left to hydrate for 20 hours at 4° C.
2. The milkbase is preheated to 65° C. (P1)
3. The milkbase is homogenised at 65° C./200 bar
4. The milkbase is pasteurised 95° C. for 6 minutes (P3)
5. The milkbase is cooled to 5° C. (K2)

TABLE 4

SET yogurt ingredients list in % (w/w)
Ingredients in % (w/w)

| Ingredient Name | |
|---|---|
| Skimmed milk (Skummet-mælk 0.1% fat, Arla Foods Amba, Denmark) | 93.533 |
| Cream 38% fat (Arla Foods Amba, Denmark) | 1.067 |
| Nutrilac YQ5075 (Arla Foods Ingredients, Denmark) | 1.400 |
| Lactose (Variolac ® 992 BG100, Arla Foods Amba, Denmark) | 3.000 |
| Enzyme/H20 | 1.000 |
| Total % | 100 |

Following, the milkbase is heated to 43° C. (K1). Dilution of the culture YO-MIX 495 consisting of Lactobacillus delbrüeckii subsp bulgaricus and Streptococcus thermophilus (DuPont Nutrition Biosciences, Denmark) was done at the fermentation temperature. 250 mL milkbase were distributed in 500 mL bluecap bottles and enzymes were added in varying concentration constitution 1% (v/v) of the final yogurt-mix The starter culture, YO-Mix 495, are added in a dosage of 20 DCU (Danisco Culture Units) per 100 liter, where one DCU is 100 billion cells measured as colony forming units. For each trial three samples were made. Fermentation was carried out to pH 4.6 at 43° C. and following stopped by fast cooling to 5° C. Yoghurt sugar/oligosaccharide composition was analyzed by HPLC on the day after fermentation (see HPLC method below). Fermented yoghurt samples were always stored at 4° C.

The results of the yoghurt experiment are shown in table 5. It can be seen that higher initial lactose (7.5% w/v) increased the total GOS generated in the yoghurt compared to the GOS achieved with 5.5% (w/v) initial lactose, as shown in table 3. A final GOS concentration of 2.954% is achieved with the 50 ppm dose of BIF917 tested, whereas 2.662% GOS was produced with 25 ppm BIF917. In comparison did the conventional hydrolyzing β-galactosidase from *Kluyveromyces lactis* (GODO-YNL2, GODO SHUSEI Co., Ltd., Japan) produced 0.355% GOS at a dose of 25 ppm. A decrease in the lactose concentration of 2.127% was observed in the blank yogurt where the same amount of $H_2O$ was added instead of enzyme.

TABLE 5

Content of DP2 saccharides (mainly lactose) and GOS (DP3+) in a fermented yogurt treated with increasing dose of BIF917 and *K. lactis* β-gal.

|  |  | Amount w/v % DP2 incl. Lactose | Std | Amount w/v % DP3+ (GOS) | Std |
|---|---|---|---|---|---|
| Yogurt | BIF917_12.5 ppm | 3.295 | 0.224 | 1.525 | 0.197 |
|  | BIF917_25 ppm | 2.090 | 0.045 | 2.662 | 0.003 |
|  | BIF917_50 ppm | 1.395 | 0.090 | 2.954 | 0.202 |
|  | *K. lactis* β-Gal_25 ppm | 0.425 | 0.040 | 0.355 | 0.006 |
|  | H20 | 5.431 | 0.099 | 0.000 | 0.000 |
| Milkbase | H20 | 7.558 | 0.265 | 0.000 | 0.000 |

To test the influence of acidification in the yogurt fermentation on BIF917 performance studies were made with three different YO-mix cultures all consisting of *Lactobacillus delbrüeckii* subsp *bulgaricus* and *Streptococcus thermophilus* (DuPont Nutrition Biosciences, Denmark): YO-MIX 495 with a relative slow fermentation time; YO-MIX 495 with a relative fast fermentation time and YO-MIX 601 with prolonged lagphase and a strong acidifying fermentation. All fermentations were performed at 43° C. with the same amount of BIF917 (25 ppm).

In addition to test the influence of temperature on BIF917 performance, fermentation with YO-MIX 495 and 25 ppm BIF917 were carried out at 43° C., 45° C. and 47° C.

The following procedure was applied to produce set-style yogurts with an initial lactose concentration of 7.5% (w/v) (corresponding to 7.1% w/w, as 1% w/v lactose=0.9423% w/w in this solution):

1. All powder ingredients (listed in table 6) are mixed and the dry blend are added to the milk/water under good agitation at 4-5° C., left to hydrate for 20 hours at 4° C.
2. The milkbase is preheated to 65° C. (P1)
3. The milkbase is homogenised at 65° C./200 bar
4. The milkbase is pasteurised 95° C. for 6 minutes (P3)
5. The milkbase is cooled to 5° C. (K2)
6. The milkbase is heated to 43° C. (K1). Dilution of the cultures YO-MIX 495, 485 and 601 (DuPont Nutrition Biosciences, Denmark) was done at the fermentation temperature.
7. 100 mL milkbase was distributed in 250 mL bluecap bottles and enzymes were added in varying concentration constitution 1% (v/v) of the final yogurt-mix
8. The starter culture, either YO-Mix 495, 485 or 601 were added in a dosage of 20 DCU (Danisco Culture Units) per 100 liter. For each trial three samples were made.
9. Fermentation was carried out to pH 4.6 at 43° C. (for temperature studies at 43° C., 45° C. and 47° C. respectively) and following stopped by fast cooling to 5° C.
10. Yoghurt sugar/oligosaccharide composition was analyzed by HPLC on the day after fermentation (see HPLC method below). Fermented yoghurt samples were always stored at 4° C.

TABLE 6

SET yogurt ingredients list in % (w/w)
Ingredients in % (w/w)
Ingredient Name

| Ingredient | % |
|---|---|
| Skimmed milk (Skummet-mælk 0.1% fat, Arla Foods Amba, Denmark) | 93.533 |
| Cream 38% fat (Arla Foods Amba, Denmark) | 1.067 |
| Nutrilac YQ5215 (Arla Foods Ingredients, Denmark) | 1.400 |
| Lactose (Variolac ® 992 BG100, Arla Foods Amba, Denmark) | 3.000 |
| Enzyme/H20 | 1.000 |
| Total % | 100 |

The results of the yoghurt experiment are shown in table 7. It can be seen that the different YO-mix cultures, having different acidification profiles, exert no significant effect on the final GOS yield. On average 3.22% (w/v) GOS is generated and the highest GOS concentration (3.300%) found in the yoghurt produced with YO-mix 485 is being within the variance of quantification. The change in fermentation temperature from 43° C. to 45° C. and 47° C. do not significantly (using a student T-test with 95% confidence limits) change the amount of GOS produced in any of the yoghurts: 3.258% w/v at 43° C., 3.375% w/v at 45° C. and 3.236% w/v at 47° C. Thus, it may be concluded that the action of BIF917 under the conditions investigated are robust for in situ generation of GOS in yogurt using various culture and temperature conditions.

TABLE 7

Content of DP2, DP3, DP4, DP5, DP6, glucose and galactose in a fermented yogurt treated with BIF917.

| Sample | Enzyme dose | Fermentation culture | Fermentation temperature | Lactose w/v % Amount | Glucose w/v % Amount | Galactose w/v % Amount | DP3 (GOS) w/v % Amount | DP4 (GOS) w/v % Amount | DP5 (GOS) w/v % Amount | DP6 (GOS) w/v % Amount | DP3+ (GOS) w/v % Amount |
|---|---|---|---|---|---|---|---|---|---|---|---|
| Milkbase |  |  |  | 7.259 | 0.000 | 0.000 | 0.000 | 0.000 | 0.000 | 0.000 | 0.000 |
| Yogurt | BIF917_25 ppm | YM 495 | 43° C. | 5.466 | 0.000 | 0.448 | 0.000 | 0.000 | 0.000 | 0.000 | 0.000 |
|  | BIF917_25 ppm | YM 495 | 43° C. | 1.770 | 1.368 | 0.648 | 2.067 | 0.793 | 0.260 | 0.074 | 3.194 |
|  | BIF917_25 ppm | YM 485 | 43° C. | 1.860 | 1.259 | 0.609 | 2.065 | 0.830 | 0.302 | 0.103 | 3.300 |
|  | BIF917_25 ppm | YM 601 | 43° C. | 1.712 | 1.418 | 0.832 | 2.094 | 0.780 | 0.248 | 0.068 | 3.189 |
|  | BIF917_25 ppm | YM 495 | 43° C. | 1.761 | 1.344 | 0.642 | 2.086 | 0.813 | 0.275 | 0.084 | 3.258 |
|  | BIF917_25 ppm | YM 495 | 45° C. | 1.838 | 1.323 | 0.625 | 2.128 | 0.848 | 0.301 | 0.099 | 3.375 |
|  | BIF917_25 ppm | YM 495 | 47° C. | 1.739 | 1.406 | 0.722 | 2.106 | 0.799 | 0.257 | 0.074 | 3.236 |
|  |  |  |  |  |  |  |  | STD |  |  |  |
| Milkbase |  |  |  | 0.252 | 0.000 | 0.000 | 0.000 | 0.000 | 0.000 | 0.000 | 0.000 |
| Yogurt | BIF917_25 ppm | YM 495 | 43° C. | 0.225 | 0.000 | 0.000 | 0.000 | 0.000 | 0.000 | 0.000 | 0.000 |
|  | BIF917_25 ppm | YM 495 | 43° C. | 0.075 | 0.067 | 0.039 | 0.080 | 0.031 | 0.010 | 0.002 | 0.123 |
|  | BIF917_25 ppm | YM 485 | 43° C. | 0.090 | 0.063 | 0.015 | 0.084 | 0.033 | 0.012 | 0.008 | 0.136 |

TABLE 7-continued

Content of DP2, DP3, DP4, DP5, DP6, glucose and galactose in a fermented yogurt treated with BIF917.

| Sample | Enzyme dose | Fermentation culture | Fermentation temperature | Lactose w/v % Amount | Glucose w/v % Amount | Galactose w/v % Amount | DP3 (GOS) w/v % Amount | DP4 (GOS) w/v % Amount | DP5 (GOS) w/v % Amount | DP6 (GOS) w/v % Amount | DP3+ (GOS) w/v % Amount |
|---|---|---|---|---|---|---|---|---|---|---|---|
| | BIF917__25 ppm | YM 601 | 43° C. | 0.013 | 0.014 | 0.017 | 0.018 | 0.010 | 0.006 | 0.002 | 0.037 |
| | BIF917__25 ppm | YM 495 | 43° C. | 0.042 | 0.031 | 0.014 | 0.046 | 0.016 | 0.005 | 0.001 | 0.067 |
| | BIF917__25 ppm | YM 495 | 45° C. | 0.071 | 0.050 | 0.013 | 0.061 | 0.028 | 0.012 | 0.007 | 0.108 |
| | BIF917__25 ppm | YM 495 | 47° C. | 0.009 | 0.015 | 0.004 | 0.003 | 0.002 | 0.003 | 0.003 | 0.011 |

HPLC Method

All chemicals used were of analytical grade. D-(+)-Lactose (min 99%, no. 17814), D-(+)-glucose (min 99.5%, no G8270-100G, batch#036K0137), and D-(+)-galactose (min 99%, no G0750-25G, batch#031M0043V) were obtained from Sigma (St. Louis, Mo., USA). Vivinal GOS Syrup (Prod. No 502675 Batch#649566) was obtained from Friesland Campina Domo (Amersfoort, The Netherlands) containing 57% on dry-matter (DM) galacto-oligosaccharides, 21% on DM anhydrous lactose, 20% on DM anhydrous glucose, and 0.8% on DM anhydrous galactose.

Sample Preparation

All standards: Lactose, Glucose, galactose and GOS were prepared in double distilled water (ddH20) and filtered through 0.45 µm syringe filters. A set of each standard was prepared ranging in concentration from 10 to 200000 ppm.

To evaluate quantification of the above set of sugars in a yogurt/milk matrix, the above standards were spiked into a milk and yogurt sample as internal controls. All milk and yogurt samples containing active β-galactosidase were inactivated by heating the sample to 95° C. for 10 min. All milk samples were prepared in 96 well MTP plates (Corning, N.Y., USA) and diluted minimum 20 times and filtered through 0.20 µm 96 well plate filters before analysis (Corning filter plate, PVDF hydrophile membrane, NY, USA). Samples containing more than 50000 ppm (5% w/v) lactose were heated to 30° C. to ensure proper solubilization. All yogurt samples were weighted and diluted 10 times in ddH20 before homogenization of the sample using of Ultra turrax TP18/10 for a few minutes (Janke & Kunkel Ikalabortechnik, Bie & Berntsen, Denmark). β-galactosidase were inactivated by heat treatment and samples were further diluted in 96 well MTP plates filtered through 0.20 µm 96 well plate filters before analysis (Corning filter plate, PVDF hydrophile membrane, NY, USA). All samples were analyzed in 96 well MTP plates sealed with tape.

Instrumentation

Quantification of galactooligosaccharides (GOS), Lactose, glucose and galactose were performed by HPLC. Analysis of samples was carried out on a Dionex Ultimate 3000 HPLC system (Thermo Fisher Scientific) equipped with a DGP-3600SD Dual-Gradient analytical pump, WPS-3000TSL thermostated autosampler, TCC-3000SD thermostated column oven, and a RI-101 refractive index detector (Shodex, J M Science). Chromeleon datasystem software (Version 6.80, DU10A Build 2826, 171948) was used for data acquisition and analysis.

Chromatographic Conditions

The samples were analyzed by HPLC using a RSO oligosaccharide column, $Ag^+$ 4% crosslinked (Phenomenex, The Netherlands) equipped with an analytical guard column (Carbo-$Ag^+$ neutral, AJ0-4491, Phenomenex, The Netherlands) at 70° C. The column was eluted with double distilled water (filtered through a regenerated cellulose membrane of 0.45 µm and purged with helium gas) at a flow rate of 0.3 ml/min.

Isocratic flow of 0.3 ml/min was maintained throughout analysis with a total run time of 37 min and injection volume was set to 10 µL. Samples were held at 30° C. in the thermostated autosampler compartment to ensure solubilisation of lactose. The eluent was monitored by means of a refractive index detector and quantification was made by the peak area relative to the peak area of the given standard. Peaks with a degree of three or higher (DP3+) in the Vivinal GOS syrup (Friesland Food Domo, The Netherlands) were used as standard for GOS quantification following manufactures declaration on GOS content in the product.

LIST OF SEQUENCES

```
>SEQ ID NO: 1 (BIF_917)
vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnltttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwnddvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstekt >SEQ ID NO: 2 (BIF_995)
vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnltttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
```

LIST OF SEQUENCES nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwnddvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstektvrsfyysrnyyvktgnkpilpsdvevrysdgtsdrqnvtwdavsddqiakagsfsva
gtvagqkisvrvtmideigal >SEQ ID NO: 3 (BIF_1068)
Vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnlttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwnddvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstektvrsfyysrnyyvktgnkpilpsdvevrysdgtsdrqnvtwdavsddqiakagsfsva
gtvagqkisvrvtmideigallnysastpvgtpavlpgsrpavlpdgtvtsanfavhwtkpadtvyntagtvkvpgtatvfgkefkvt
atirvq >SEQ ID NO: 4 (BIF_1172)
vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnlttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwnddvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstektvrsfyysrnyyvktgnkpilpsdvevrysdgtsdrqnvtwdavsddqiakagsfsva
gtvagqkisvrvtmideigallnysastpvgtpavlpgsrpavlpdgtvtsanfavhwtkpadtvyntagtvkvpgtatvfgkefkvt
atirvqrsqvtigssvsgnalrltqnipadkqsdtldaikdgsttvdantggganpsawtnwayskaghntaeitfeyateqqlgqiv
myffrdsnavrfpdagktkiqi >SEQ ID NO: 5 (BIF_1241)
vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnlttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwnddvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstektvrsfyysrnyyvktgnkpilpsdvevrysdgtsdrqnvtwdavsddqiakagsfsva
gtvagqkisvrvtmideigallnysastpvgtpavlpgsrpavlpdgtvtsanfavhwtkpadtvyntagtvkvpgtatvfgkefkvt
atirvqrsqvtigssvsgnalrltqnipadkqsdtldaikdgsttvdantggganpsawtnwayskaghntaeitfeyateqqlgqiv
myffrdsnavrfpdagktkiqisadgknwtdlaatetiaaqessdrvkpytydfapvgatfvkvtvtnadttttpsgvvcaglteielkt >SEQ ID NO: 6 (BIF_1326)
vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnlttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwnddvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstektvrsfyysrnyyvktgnkpilpsdvevrysdgtsdrqnvtwdavsddqiakagsfsva
gtvagqkisvrvtmideigallnysastpvgtpavlpgsrpavlpdgtvtsanfavhwtkpadtvyntagtvkvpgtatvfgkefkvt
atirvqrsqvtigssvsgnalrltqnipadkqsdtldaikdgsttvdantggganpsawtnwayskaghntaeitfeyateqqlgqiv
myffrdsnavrfpdagktkiqisadgknwtdlaatetiaaqessdrvkpytydfapvgatfvkvtvtnadttttpsgvvcaglteielkt
atskfvtntsaalssltvngtkvsdsvlaagsyntpaiiadvkaegegnasvtvlpahdnvirviteseedhvtrktftinlgteqef >SEQ ID NO: 7 Bifidobacterium bifidum glycoside hydrolase catalytic core
qnrtsdfdanwkfmlsdsvqaqdpafddsawqqvdlphdysitqkysqsneaesaylpggtgwyrksftidrdlagkriainfdgv
ymnatvwfngvklgthpygyspfsfdltgnakfggentivvkvenrlpssrwysgsgiyrdvtltvtdgvhvgnngvaiktpslatq
nggdvtmnlttkvandteaaanitlkqtvfpkggktdaaigtvttasksiaagasadvtstitaaspklwsiknpnlytvrtevlnggk vldtydteygfrwtgfdatsgfslngekvklkgvsmhhdqgslgavanrraierqveilqkmgvnsirtthnpaakalidvcnekgvl
vveevfdmwnrskngntedygkwfgqaiagdnavlggdkdetwakfdltstinrdmapsvimwslgnemmegisgsvsgfp
atsaklvawtkaadstrpmty >SEQ ID NO: 8 nucleotide sequence encoding full length
gcagttgaagatgcaacaagaagcgatagcacaacacaaatgtcatcaacaccggaagttgtttattcatcagcggtcgatagcaa
acaaaatcgcacaagcgattttgatgcgaactggaaatttatgctgtcagatagcgttcaagcacaagatccggcatttgatgattca
gcatggcaacaagttgatctgccgcatgattatagcatcacacagaaatatagccaaagcaatgaagcagaatcagcatatcttccg
ggaggcacaggctggtatagaaaaagctttacaattgatagagatctggcaggcaaacgcattgcgattaattttgatggcgtctat
atgaatgcaacagtctggtttaatggcgttaaactgggcacacatccgtatggctattcaccgttttcatttgatctgacaggcaatgca
aaatttggcggagaaaacacaattgtcgtcaaagttgaaaatagactgccgtcatcaagatggtattcaggcagcggcatttataga
gatgttacactgacagttacagatggcgttcatgttggcaataatggcgtcgcaattaaaaacaccgtcactggcaacacaaaatggc
ggagatgtcacaatgaacctgacaacaaaagtcgcgaatgatacagaagcagcagcgaacattacactgaaacagacagttttc
cgaaaggcggaaaaacggatgcagcaattggcacagttacaacagcatcaaaatcaattgcagcaggcgcatcagcagatgttac
aagcacaattacagcagcaagcccgaaactgtggtcaattaaaaacccgaacctgtatacagttagaacagaagttctgaaccgga
ggcaaagttctggatacatatgatacagaatatggctttcgctggacaggctttgatgcaacatcaggcttttcactgaatggcgaaa
aagtcaaactgaaaggcgttagcatgcatcatgatcaaggctcacttggcgcagttgcaaatagacgcgcaattgaaagacaagtc
gaaatcctgcaaaaaatgggcgtcaatagcattcgcacaacacataatccggcagcaaaagcactgattgatgtctgcaatgaaaa
aggcgttctggttgtcgaagaagtctttgatatgtggaaccgcagcaaaaatggcaacacggaagattatggcaaatggtttggcca
agcaattgcaggcgataatgcagttctgggaggcgataataagatgaaacatgggcgaaatttgatcttacatcaacaattaaccgcg
atagaaatgcaccgtcagttattatgtggtcactgggcaatgaaatgatggaagcatttccaggctcagttttcaggctttccggcaac
atcagcaaactggttgcatggacaaaagcagcagattcaacaagaccgatgacatatggcgataacaaaattaaagcgaactgg
aacgaatcaaatacaatgggcgataatctgacagcaaatggcggagttgttggcacaaattattcagatggcgcaaactatgataa
aattcgtacaacacatccgtcatgggcaatttatggctcagaaacagcatcagcgattaatagccgtggcatttgcatttataatagaacaaca
ggcgagcacaatcatcagatcaaacagctgacaagctatgtaattcagcagttggctgggaagcagttgcatcatcagcatggta
tgatgttgttcagagagattttgtcgcaggcacatatgtttggacaggatttgattatctgggcgaaccgacaccgtggaatggcaca
ggctcaggcgcagttggctcatggccgtcaccgaaaaatagctattttggcatcgttgatacagcaggctttccgaaagatacatatt
attttttatcagagccagtggaatgatgatgttcatacactgcatattcttccggcagatgttgaagttcgctattcagatggaacaagcgatagacaaa
acgttacatgggatgcagttcagatgatcaaattgcaaaagcaggctcattttcagttgcaggcacagttgcaggccaaaaatta
gcgttcgcgtcacaatgattgatgaaattggcgcactgctgaatttattcagcaagcacaccggttggcacaccggcagttcttccggg
atcaagaccggcagtcctgccggatggcacagtcacatcagcaaattttgcagtccattggacaaaaccggcagatacagtctataa
tacagcaggcacagtcaaagtaccgggaacagcaacagttttggcaaagaatttaaagtcacagcgacaattagagttcaaaga
agccaagttacaattggctcatcagtttcaggaaatgcactgagactgacacaaaatattccggcagataaacaatcagatacactg
gatgcgattaaagatggctcaacaacagttgatgcaaatacaggcggaggcgcaaatccgtcagcatggacaaattgggcatattc
aaaagcaggccataacacagcggaaattacatttgaatatgcgacagaacaacaactgggccagatcgtcatgtatttttttcgcga
tagcaatgcagttagatttccggatgctggcaaaacaaaaattcagatcagcgcagatgttgaagttcgctattcagatggaacaagcgatagacaaa
cagaaacaattgcagcgcaagaatcaagcgatagagtcaaaccgtatacatatgattttgcaccggttggcgcaacatttgttaaag
tgacagtcacaaacgcagatacaacaacaccgtcaggcgttgtttgcgcaggcctgacagaaattgaactgaaaacagcgacaag
caaatttgtcacaaatacatcagcagcactgtcatcacttacagtcaatggcacaaaagtttcagattcagttctggcagcaggctcat
ataacacaccggcaattatcgcagatgttaaagcggaaggcgaaggcaatgcaaagctttcaccttccggcacatgataatgtt
attcgcgtcattacagaaagcgaagatcatgtcacacgcaaaacatttacaatcaacctgggcacagaacaagaatttccggctgat
tcagatgaaagagattatccggcagcagatatgacagtcacagttggctcagaacaaacatcaggcacagcaacagaaggaccg
aaaaaatttgcagtcgatggcaacacatcaacatattggcatagcaattggacaccgacaacagttaatgatctgtggatcgcgtttg
aactgcaaaaaccgacaaaactggatgcactgagatatcttccgcgtccggcaggctcaaaaaatggcagcgtcacagaatataa
agttcaggtgtcagatgatggaacaaactggacagatgcaggctcaggcacatggacaacggattatggctggaaactggcggaa
tttaatcaaccggtcacaacaaaacatgttagactgaaagcggttcatacatatgcagatagcggcaacgataaatttatgagcgca
agcgaaattagactgagaaaagcggtcgatacaacggatatttcaggcgcaacagttacagttccggcaaaactgacagttgatag
agttgatgcagatcatccggcaacatttgcaacaaaagatgtcacagttacactgggagatgcaacactgagatatggcgttgatta
tctgctggattatgcaggcaatacagcagttggcaaagcaacagtgacagttagaggcattgataaatattcaggcacagtcgcga
aaacatttacaattgaactgaaaaatgcaccggcaccggaaccgacactgacatcagttagcgtcaaaacaaaaccgagcaaact
gacatatgttgtcggagatgcatttgatccggcaggcctggttctgcaacatgatagacaagcagatagacctccgcaaccgctggtt
ggcgaacaagcggatgaacgcggactgacatgcggcacaagatgcgatagagttgaacaactgcgcaaacatgaaaatagaga
agcgcatagaacaggcctggatcatctgaatttgttggcgcagcagatggcgcagttggagaacaagcaacatttaaagtccatg
tccatgcagatcaggagatggcagacatgatgatgcagataacgcgatattgatccgcatgttccggtcgatcatgcagttggcg
aactggcaagagcagcatgccatcatgttattggcctgagagtcgatacacatagacttaaagcaagcggctttcaaattccggctg
atgatatggcagaaatcgatcgcattacaggctttcatcgttttgaacgccatgtc >SEQ ID NO: 9 nucleotide sequence encoding BIF_917
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagca
tggcaacaagttgatctgccgcatgattatagcatcacacagaaatatagccaaagcaatgaagcagaatcagcatatcttccggga
ggcacaggctggtatagaaaaagctttacaattgatagagatctggcaggcaaacgcattgcgattaattttgatggcgtctatatga
atgcaacagtctggtttaatggcgttaaactgggcacacatccgtatggctattcaccgttttcatttgatctgacaggcaatgcaaaat
ttggcggagaaaacacaattgtcgtcaaagttgaaaatagactgccgtcatcaagatggtattcaggcagcggcatttatagagatg
ttacactgacagttacagatggcgttcatgttggcaataatggcgtcgcaattaaaaacaccgtcactggcaacacaaaatggcgag
atgtcacaatgaacctgacaacaaaagtcgcgaatgatacagaagcagcagcgaacattacactgaaacagacagttttccgaaa
ggcggaaaaacggatgcagcaattggcacagttacaacagcatcaaaatcaattgcagcaggcgcatcagcagatgttacaagca
caattacagcagcaagcccgaaactgtggtcaattaaaaacccgaacctgtatacagttagaacagaagttctgaaccggaggcaa

```
agttctggatacatatgatacagaatatggctttcgctggacaggctttgatgcaacatcaggcttttcactgaatggcgaaaaagtc
aaactgaaaggcgttagcatgcatcatgatcaaggctcacttggcgcagttgcaaatagacgcgcaattgaaagacaagtcgaaat
cctgcaaaaaatgggcgtcaatagcattcgcacaacacataatccggcagcaaaagcactgattgatgtctgcaatgaaaaaggcg
ttctggttgtcgaagaagtctttgatatgtggaaccgcagcaaaaatggcaacacggaagattatggcaaatggtttggccaagcaa
ttgcaggcgataatgcagttctgggaggcgataaagatgaaacatgggcgaaatttgatcttacatcaacaattaaccgcgataga
aatgcaccgtcagttattatgtggtcactgggcaatgaaatgatggaaggcatttcaggctcagtttcaggctttccggcaacatcag
caaaactggttgcatggacaaaagcagcagattcaacaagaccgatgacatatggcgataacaaaattaaagcgaactggaacg
aatcaaatacaatgggcgataatctgacagcaaatggcggagttgttggcacaaattattcagatggcgcaaactatgataaaattc
gtacaacacatccgtcatgggcaatttatggctcagaaacagcatcagcgattaatagccgtggcatttataatagaacaacaggcg
gagcacaatcatcagatcaaagctgacaagctatgataattcagcagttggctggggagcagttgcatcatcagcatggtatgatg
ttgttcagagagattttgtcgcaggcacatatgtttggacaggatttgattatctgggcgaaccgacaccgtggaatggcacaggctc
aggcgcagttggctcatggccgtcaccgaaaaatagctattttggcatcgttgatacagcaggctttccgaaagatacatattattttt
atcagagccagtggaatgatgatgttcatacactgcatattcttccggcatggaatgaaaatgttgttgcaaaaggctcaggcaataa
tgttccggttgtcgtttatacagatgcagcgaaagtgaaactgtattttacaccgaaaggctcaacagaaaaaagactgatcggcga
aaaatcatttacaaaaaaaacaacagcggcaggctatacatatcaagtctatgaaggcagcgataaagattcaacagcgcataaa
aacatgtatctgacatggaatgttccgtgggcagaaggcacaatttcagcggaagcgtatgatgaaaataatcgcctgattccggaa
ggcagcacagaaggcaacgcatcagttacaacaacaggcaaagcagcaaaactgaaagcagatgcggatcgcaaaacaattac
agcggatggcaaagatctgtcatatattgaagtcgatgtcacagatgcaaatggccatattgttccggatgcagcaaatagagtcac
atttgatgttaaaggcgcaggcaaactggttggcgttgataatggctcatcaccggatcatgattcatatcaagcggataaccgcaa
agcattttcaggcaaagtcctggcaattgttcagtcaacaaaagaagcaggcgaaattacagttacagcaaaagcagatggcctgc
aatcaagcacagttaaaattgcaacaacagcagttccgggaacaagcacagaaaaaaca >SEQ ID NO: 10 nucleotide sequence encoding BIF_995
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagca
tggcaacaagttgatctgccgcatgattatagcatcacacagaaatatagccaaagcaatgaagcagaatcagcatatcttccggga
ggcacaggctggtatagaaaaagctttacaattgatagagatctggcaggcaaacgcattgcgattaattttgatggcgtctatatga
atgcaacagtctggtttaatggcgttaaactgggcacacatccgtatggctattcaccgttttcatttgatctgacaggcaatgcaaat
ttggcggagaaaacacaattgtcgtcaaagttgaaaatagactgccgtcatcaagatggtattcaggcagcggcatttatagagatg
ttacactgacagttacagatggcgttcatgttggcaataatggcgtcgcaattaaaacaccgtcactggcaacacaaaatggcggag
atgtcacaatgaacctgacaacaaaagtcgcgaatgatacagaagcagcagcgaacattacactgaaacagacagttttttccgaaa
ggcggaaaaacggatgcagcaattggcacagttacaacagcatcaaaatcaattgcagcaggcgcatcagcagatgttacaagca
caattacagcagcaagcccgaaactgtggtcaattaaaaaacccgaacctgtatacagttagaacagaagttctgaacggaggcaa
agttctggatacatatgatacagaatatggctttcgctggacaggctttgatgcaacatcaggcttttcactgaatggcgaaaaagtc
aaactgaaaggcgttagcatgcatcatgatcaaggctcacttggcgcagttgcaaatagacgcgcaattgaaagacaagtcgaaat
cctgcaaaaaatgggcgtcaatagcattcgcacaacacataatccggcagcaaaagcactgattgatgtctgcaatgaaaaaggcg
ttctggttgtcgaagaagtctttgatatgtggaaccgcagcaaaaatggcaacacggaagattatggcaaatggtttggccaagcaa
ttgcaggcgataatgcagttctgggaggcgataaagatgaaacatgggcgaaatttgatcttacatcaacaattaaccgcgataga
aatgcaccgtcagttattatgtggtcactgggcaatgaaatgatggaaggcatttcaggctcagtttcaggctttccggcaacatcag
caaaactggttgcatggacaaaagcagcagattcaacaagaccgatgacatatggcgataacaaaattaaagcgaactggaacg
aatcaaatacaatgggcgataatctgacagcaaatggcggagttgttggcacaaattattcagatggcgcaaactatgataaaattc
gtacaacacatccgtcatgggcaatttatggctcagaaacagcatcagcgattaatagccgtggcatttataatagaacaacaggcg
gagcacaatcatcagatcaaagctgacaagctatgataattcagcagttggctggggagcagttgcatcatcagcatggtatgatg
ttgttcagagagattttgtcgcaggcacatatgtttggacaggatttgattatctgggcgaaccgacaccgtggaatggcacaggctc
aggcgcagttggctcatggccgtcaccgaaaaatagctattttggcatcgttgatacagcaggctttccgaaagatacatattattttt
atcagagccagtggaatgatgatgttcatacactgcatattcttccggcatggaatgaaaatgttgttgcaaaaggctcaggcaataa
tgttccggttgtcgtttatacagatgcagcgaaagtgaaactgtattttacaccgaaaggctcaacagaaaaaagactgatcggcga
aaaatcatttacaaaaaaaacaacagcggcaggctatacatatcaagtctatgaaggcagcgataaagattcaacagcgcataaa
aacatgtatctgacatggaatgttccgtgggcagaaggcacaatttcagcggaagcgtatgatgaaaataatcgcctgattccggaa
ggcagcacagaaggcaacgcatcagttacaacaacaggcaaagcagcaaaactgaaagcagatgcggatcgcaaaacaattac
agcggatggcaaagatctgtcatatattgaagtcgatgtcacagatgcaaatggccatattgttccggatgcagcaaatagagtcac
atttgatgttaaaggcgcaggcaaactggttggcgttgataatggctcatcaccggatcatgattcatatcaagcggataaccgcaa
agcattttcaggcaaagtcctggcaattgttcagtcaacaaaagaagcaggcgaaattacagttacagcaaaagcagatggcctgc
aatcaagcacagttaaaattgcaacaacagcagttccgggaacaagcacagaaaaaacagtccgcagcttttattacagccgcaac
tattatgtcaaaacaggcaacaaaccgattctgccgtcagatgttgaagttcgctattcagatggaacaagcgatagacaaaacgtt
acatgggatgcagtttcagatgatcaaattgcaaaagcaggctcattttcagttgcaggcacagttgcaggccaaaaaattagcgttc
gcgtcacaatgattgatgaaattggcgcactg >SEQ ID NO: 11 nucleotide sequence encoding BIF_1068
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagca
tggcaacaagttgatctgccgcatgattatagcatcacacagaaatatagccaaagcaatgaagcagaatcagcatatcttccggga
ggcacaggctggtatagaaaaagctttacaattgatagagatctggcaggcaaacgcattgcgattaattttgatggcgtctatatga
atgcaacagtctggtttaatggcgttaaactgggcacacatccgtatggctattcaccgttttcatttgatctgacaggcaatgcaaat
ttggcggagaaaacacaattgtcgtcaaagttgaaaatagactgccgtcatcaagatggtattcaggcagcggcatttatagagatg
ttacactgacagttacagatggcgttcatgttggcaataatggcgtcgcaattaaaacaccgtcactggcaacacaaaatggcggag
atgtcacaatgaacctgacaacaaaagtcgcgaatgatacagaagcagcagcgaacattacactgaaacagacagttttttccgaaa
ggcggaaaaacggatgcagcaattggcacagttacaacagcatcaaaatcaattgcagcaggcgcatcagcagatgttacaagca
caattacagcagcaagcccgaaactgtggtcaattaaaaaacccgaacctgtatacagttagaacagaagttctgaacggaggcaa
agttctggatacatatgatacagaatatggctttcgctggacaggctttgatgcaacatcaggcttttcactgaatggcgaaaaagtc
aaactgaaaggcgttagcatgcatcatgatcaaggctcacttggcgcagttgcaaatagacgcgcaattgaaagacaagtcgaaat
cctgcaaaaaatgggcgtcaatagcattcgcacaacacataatccggcagcaaaagcactgattgatgtctgcaatgaaaaaggcg
ttctggttgtcgaagaagtctttgatatgtggaaccgcagcaaaaatggcaacacggaagattatggcaaatggtttggccaagcaa
ttgcaggcgataatgcagttctgggaggcgataaagatgaaacatgggcgaaatttgatcttacatcaacaattaaccgcgataga
aatgcaccgtcagttattatgtggtcactgggcaatgaaatgatggaaggcatttcaggctcagtttcaggctttccggcaacatcag
caaaactggttgcatggacaaaagcagcagattcaacaagaccgatgacatatggcgataacaaaattaaagcgaactggaacg
aatcaaatacaatgggcgataatctgacagcaaatggcggagttgttggcacaaattattcagatggcgcaaactatgataaaattc
```

-continued

LIST OF SEQUENCES gtacaacacatccgtcatgggcaatttatggctcagaaacagcatcagcgattaatagccgtggcatttataatagaacaacaggcg
gagcacaatcatcagataaacagctgacaagctatgataattcagcagttggctggggagcagttgcatcatcagcatggtatgatg
ttgttcagagagattttgtcgcaggcacatatgtgtttggacaggattttgattatctgggcgaaccgacaccgtggaatggcacaggctc
aggcgcagttggctcatggccgtcaccgaaaaatagctattttggcatcgttgatacagcaggcttttccgaaagatacatattattttt
atcagagccagtggaatgatgatgttcatacactgcatattcttccggcatggaatgaaaatgttgttgcaaaaggctcaggcaataa
tgttccggttgtcgtttatacagatgcagcgaaagtgaaactgtattttacaccgaaaggctcaacagaaaaaagactgatcggcga
aaaatcatttacaaaaaaaacaacagcggcaggctatacatatcaagtctatgaaggcagcgataaagattcaacagcgcataaa
aacatgtatctgacatggaatgttccgtgggcagaaggcacaattcagcggaagcgtatgatgaaaataatcgcctgattccgaa
ggcagcacagaaggcaacgcatcagttacaacaacaggcaaagcagcaaaactgaaagcagatgcggatcgcaaaacaattac
agcggatggcaaagatctgtcatatattgaagtcgatgtcacagatgcaaatggccatattgttccggatgcagcaaatagagtcac
atttgatgttaaaggcgcaggcaaactggttggcgttgataatggctcatcaccggatcatgattcatatcaagcggataaccgcaa
agcattttcaggcaaagtcctggcaattgttcagtcaacaaaagaagcaggcgaaattacagttacagcaaaagcagatggcctgc
aatcaagcacagttaaaattgcaacaacagcagttccgggaacaagcacagaaaaaacagtccgcagcttttattacagccgcaac
tattatgtcaaaacaggcaacaaaccgattctgccgtcagatgttgaagttcgctattcagatggaacaagcgatagacaaaacgtt
acatgggatgcagtttcagatgatcaaattgcaaaagcaggctcattttcagttgcaggcacagttgcaggccaaaaaattagcgttc
gcgtcacaatgattgatgaaattggcgcactgctgaattattcagcaagcacaccggttggcacaccggcagttcttccgggatcaa
gaccggcagtcctgccggatggcacagtcacatcagcaaattttgcagtccattggacaaaaccggcagatacagtctataatacag
caggcacagtcaaagtaccgggaacagcaacagttttttggcaaagaatttaaagtcacagcgacaattagagttcaa >SEQ ID NO: 12 nucleotide sequence encoding BIF_1172
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagca
tggcaacaagttgatctgccgcatgattatagcatcacacagaaatatagccaaagcaatgaagcagaatcagcatatcttccggga
ggcacaggctggtatagaaaaagcttttacaattgatagagatctggcaggcaaacgcattgcgattaattttgatggcgtctatatga
atgcaacagtctggtttaatggcgttaaactgggcacacatccgtatggctattcaccgttttcatttgatctgacaggcaatgcaaaat
ttggcggagaaaacacaattgtcgtcaaagttgaaaatagactgccgtcatcaagatggtattcaggcagcggcatttatagagatg
ttacactgacagttacagatggcgttcatgttggcaataatggcgtcgcaattaaaacaccgtcactggcaacacaaaatggcggag
atgtcacaatgaacctgacaacaaaagtcgcgaatgatacagaagcagcagcgaacattacactgaaacagacagttttttccgaaa
ggcggaaaaacggatgcagcaattggcacagttacaacagcatcaaaatcaattgcagcaggcgcatcagcagatgttacaagca
caattacagcagcaagcccgaaactgtggtcaattaaaaacccgaacctgtatacagttagaacagaagttctgaacggaggcaa
agttctggatacatatgatacagaatatggctttcgctggacaggctttgatgcaacatcaggcttttcactgaatggcgaaaaagtc
aaactgaaaggcgttagcatgcatcatgatcaaggctcacttggcgcagttgcaaatagacgcgcaattgaaagacaagtcgaaat
cctgcaaaaaatgggcgtcaatagcattcgcacaacacataatccggcagcaaaagcactgattgatgtctgcaatgaaaaaggcg
ttctggttgtcgaagaagtctttgatatgtggaaccgcagcaaaaatggcaacacggaagattatgcaaatggtttggccaagcaa
ttgcaggcgataatgcagttctgggaggcgataaagatgaaacatgggcgaaatttgatcttacatcaacaattaaccgcgataga
aatgcaccgtcagttattatgtggtcactgggcaatgaaatgatggaaggcatttcaggctcagtttcaggctttccggcaacatcag
caaaactggttgcatggacaaaagcagcagattcaacaagaccgatgacatatggcgcataaacaaaattaaagcgaactggaacg
aatcaaatacaatgggcgataatctgacagcaaatggcggagttgttgcacaaattattcagatggcgcaaactatgataaaattc
gtacaacacatccgtcatgggcaatttatggctcagaaacagcatcagcgattaatagccgtggcatttataatagaacaacaggcg
gagcacaatcatcagataaacagctgacaagctatgataattcagcagttggctggggagcagttgcatcatcagcatggtatgatg
ttgttcagagagattttgtcgcaggcacatatgtgtttggacaggattttgattatctgggcgaaccgacaccgtggaatggcacaggctc
aggcgcagttggctcatggccgtcaccgaaaaatagctattttggcatcgttgatacagcaggcttttccgaaagatacatattattttt
atcagagccagtggaatgatgatgttcatacactgcatattcttccggcatggaatgaaaatgttgttgcaaaaggctcaggcaataa
tgttccggttgtcgtttatacagatgcagcgaaagtgaaactgtattttacaccgaaaggctcaacagaaaaaagactgatcggcga
aaaatcatttacaaaaaaaacaacagcggcaggctatacatatcaagtctatgaaggcagcgataaagattcaacagcgcataaa
aacatgtatctgacatggaatgttccgtgggcagaaggcacaattcagcggaagcgtatgatgaaaataatcgcctgattccgaa
ggcagcacagaaggcaacgcatcagttacaacaacaggcaaagcagcaaaactgaaagcagatgcggatcgcaaaacaattac
agcggatggcaaagatctgtcatatattgaagtcgatgtcacagatgcaaatggccatattgttccggatgcagcaaatagagtcac
atttgatgttaaaggcgcaggcaaactggttggcgttgataatggctcatcaccggatcatgattcatatcaagcggataaccgcaa
agcattttcaggcaaagtcctggcaattgttcagtcaacaaaagaagcaggcgaaattacagttacagcaaaagcagatggcctgc
aatcaagcacagttaaaattgcaacaacagcagttccgggaacaagcacagaaaaaacagtccgcagcttttattacagccgcaac
tattatgtcaaaacaggcaacaaaccgattctgccgtcagatgttgaagttcgctattcagatggaacaagcgatagacaaaacgtt
acatgggatgcagtttcagatgatcaaattgcaaaagcaggctcattttcagttgcaggcacagttgcaggccaaaaaattagcgttc
gcgtcacaatgattgatgaaattggcgcactgctgaattattcagcaagcacaccggttggcacaccggcagttcttccgggatcaa
gaccggcagtcctgccggatggcacagtcacatcagcaaattttgcagtccattggacaaaaccggcagatacagtctataatacag
caggcacagtcaaagtaccgggaacagcaacagttttttggcaaagaatttaaagtcacagcgacaattagagttcaaagaagcca
agttacaattggctcatcagtttcaggaaatgcactgagactgacacaaaaatattccggcagataaacaatcagatacactggatgc
gattaaagatggctcaacaacagttgatgcaaatacaggcggaggcgcaaatccgtcagcatggacaaattgggcatattcaaaa
gcaggccataacacagcggaaattacatttgaatatgcacagaacaacaactgggccagatcgtcatgtatttttttcgcgatagca
atgcagttagatttccggatgctggcaaaacaaaaattcagatc >SEQ ID NO: 13 nucleotide sequence encoding BIF_1241
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagca
tggcaacaagttgatctgccgcatgattatagcatcacacagaaatatagccaaagcaatgaagcagaatcagcatatcttccggga
ggcacaggctggtatagaaaaagcttttacaattgatagagatctggcaggcaaacgcattgcgattaattttgatggcgtctatatga
atgcaacagtctggtttaatggcgttaaactgggcacacatccgtatggctattcaccgttttcatttgatctgacaggcaatgcaaaat
ttggcggagaaaacacaattgtcgtcaaagttgaaaatagactgccgtcatcaagatggtattcaggcagcggcatttatagagatg
ttacactgacagttacagatggcgttcatgttggcaataatggcgtcgcaattaaaacaccgtcactggcaacacaaaatggcggag
atgtcacaatgaacctgacaacaaaagtcgcgaatgatacagaagcagcagcgaacattacactgaaacagacagttttttccgaaa
ggcggaaaaacggatgcagcaattggcacagttacaacagcatcaaaatcaattgcagcaggcgcatcagcagatgttacaagca
caattacagcagcaagcccgaaactgtggtcaattaaaaacccgaacctgtatacagttagaacagaagttctgaacggaggcaa
agttctggatacatatgatacagaatatggctttcgctggacaggctttgatgcaacatcaggcttttcactgaatggcgaaaaagtc
aaactgaaaggcgttagcatgcatcatgatcaaggctcacttggcgcagttgcaaatagacgcgcaattgaaagacaagtcgaaat
cctgcaaaaaatgggcgtcaatagcattcgcacaacacataatccggcagcaaaagcactgattgatgtctgcaatgaaaaaggcg
ttctggttgtcgaagaagtctttgatatgtggaaccgcagcaaaaatggcaacacggaagattatgcaaatggtttggccaagcaa
ttgcaggcgataatgcagttctgggaggcgataaagatgaaacatgggcgaaatttgatcttacatcaacaattaaccgcgataga -continued

LIST OF SEQUENCES aatgcaccgtcagttattatgtggtcactgggcaatgaaatgatggaaggcatttcaggctcagtttcaggctttccggcaacatcag
caaaactggttgcatggacaaaagcagcagattcaacaagaccgatgacatatggcgataacaaaattaaagcgaactggaacg
aatcaaatacaatgggcgataatctgacagcaaatggcggagttgttggcacaaattattcagatggcgcaaactatgataaaattc
gtacaacacatccgtcatgggcaatttatggctcagaaacagcatcagcgattaatagccgtggcatttataatagaacaacaggcg
gagcacaatcatcagataaacagctgacaagctatgataattcagcagttggctggggagcagttgcatcatcagcatggtatgatg
ttgttcagagagattttgtcgcaggcacatatgtttggacaggatttgattatctgggcgaaccgacaccgtggaatggcacaggctc
aggcgcagttggctcatggccgtcaccgaaaaatagctattttggcatcgttgatacagcaggcttttccgaaagatacatattattttt
atcagagccagtggaatgatgatgttcatacactgcatattcttccggcatggaatgaaaatgttgttgcaaaaggctcaggcaataa
tgttccggttgtcgtttatacagatgcagcgaaagtgaaactgtattttacaccgaaaggctcaacagaaaaaagactgatcggcga
aaaatcatttacaaaaaaaacaacagcggcaggctatacatatcaagtctatgaaggcagcgataaagattcaacagcgcataaa
aacatgtatctgacatggaatgttccgtgggcagaaggcacaatttcagcggaagcgtatgatgaaaataatcgcctgattccgaa
ggcagcacagaaggcaacgcatcagttacaacaacaggcaaagcagcaaaactgaaagcagatgcggatcgcaaaacaattac
agcggatggcaaagatctgtcatatattgaagtcgatgtcacagatgcaaatggccatattgttccggatgcagcaaatagagtcac
atttgatgttaaaggcgcaggcaaactggttggcgttgataatggctcatcaccggatcatgattcatatcaagcggataaccgcaa
agcattttcaggcaaagtcctggcaattgttcagtcaacaaaagaagcaggcgaaattacagttacagcaaaagcagatggcctgc
aatcaagcacagttaaaattgcaacaacagcagttccgggaacaagcacagaaaaaacagtccgcagcttttattacagccgcaac
tattatgtcaaaacaggcaacaaaccgattctgccgtcagatgttgaagttcgctattcagatggaacaagcgatagacaaaacgtt
acatgggatgcagtttcagatgatcaaattgcaaaagcaggctcattttcagttgcaggcacagttgcaggccaaaaaattagcgttc
gcgtcacaatgattgatgaaattggcgcactgctgaattattcagcaagcacaccggttggcacaccggcagttcttccgggatcaa
gaccggcagtcctgccggatggcacagtcacatcagcaaattttgcagtccattggacaaaaccggcagatacagtctataatacag
caggcacagtcaaagtaccgggaacagcaacagttttttggcaaagaatttaaagtcacagcgacaattagagttcaaagaagcca
agttacaattggctcatcagtttcaggaaatgcactgagactgacacaaaatattccggcagataaacaatcagatacactggatgc
gattaaagatggctcaacaacagttgatgcaaatacaggcggaggcgcaaatccgtcagcatggacaaattgggcatattcaaaa
gcaggccataacacagcggaaattacatttgaatatgcgacagaacaacaactgggccagatcgtcatgtatttttttcgcgatagca
atgcagttagatttccggatgctggcaaaacaaaaattcagatcagcgcagatggcaaaaattggacagatctggcagcaacaga
aacaattgcagcgcaagaatcaagcgatagagtcaaaccgtatacatatgattttgcaccggttggcgcaacatttgttaaagtgac
agtcacaaacgcagatacaacaacaccgtcaggcgttgtttgcgcaggcctgacagaaattgaactgaaaacagcgaca >SEQ ID NO: 14 nucleotide sequence encoding BIF_1326
gttgaagatgcaacaagaagcgatagcacaacacaaatgtcatcaacaccggaagttgtttattcatcagcggtcgatagcaaaca
aaatcgcacaagcgattttgatgcgaactggaaatttatgctgtcagatagcgttcaagcacaagatccggcatttgatgattcagca
tggcaacaagttgatctgccgcatgattatagcatcacacagaaatatagccaaagcaatgaagcagaatcagcatatctccggga
ggcacaggctggtatagaaaaagctttacaattgatagagatctggcaggcaaacgcattgcgattaattttgatggcgtctatatga
atgcaacagtctggtttaatgcgttaaactgggcacacatccgtatggctattcaccgttttcatttgatctgacaggcaatgcaaaat
ttggcggagaaaacacaattgtcgtcaaagttgaaaatagactgccgtcatcaagatggtattcaggcagcggcatttatagagatg
ttacactgacagttacagatggcgttcatgttggcaataatggcgtcgcaattaaaaacaccgtcactggcaacacaaaatggcggag
atgtcacaatgaacctgcaacaaaagtcgcgaatgatacagaagcagcagcgaacattacactgaaacagacagttttttccgaaa
ggcgaaaaacggatgcagcaattggcacagttacaacagcatcaaaatcaattgcagcaggcgcatcagcagatgttacaagca
caattacagcagcaagcccgaaactgtggtcaattaaaaacccgaacctgtatacagttagaacagaagttctgaacggaggcaa
agttctggatacatatgatacagaatatggctttcgctggacaggctttgatgcaacatcaggcttttcactgaatggcgaaaaagtc
aaactgaaaggcgttagcatgcatcatgatcaaggctcacttggcgcagttgcaaatagacgcgcaagtgcaaatagacaagtcgaaat
cctgcaaaaaatgggcgtcaatagcattcgcacaacacataatccggcagcaaaagcactgattgatgtctgcaatgaaaaaggcg
ttctggttgtcgaagaagtctcttgatatgtggaaccgcagcaaaaatggcaacacggaagattatggcaaatggtttggccaagcaa
ttgcaggcgataatgcagttctgggaggcgataaagatgaaacatgggcgaaatttgatcttacatcaacaattaaccgcgataga
aatgcaccgtcagttattatgtggtcactgggcaatgaaatgatggaaggcatttcaggctcagtttcaggctttccggcaacatcag
caaaactggttgcatggacaaaagcagcagattcaacaagaccgatgacatatggcgataacaaaattaaagcgaactggaacg
aatcaaatacaatgggcgataatctgacagcaaatggcggagttgttggcacaaattattcagatggcgcaaactatgataaaattc
gtacaacacatccgtcatgggcaatttatggctcagaaacagcatcagcgattaatagccgtggcatttataatagaacaacaggcg
gagcacaatcatcagataaacagctgacaagctatgataattcagcagttggctggggagcagttgcatcatcagcatggtatgatg
ttgttcagagagattttgtcgcaggcacatatgtttggacaggatttgattatctgggcgaaccgacaccgtggaatggcacaggctc
aggcgcagttggctcatggccgtcaccgaaaaatagctattttggcatcgttgatacagcaggcttttccgaaagatacatattattttt
atcagagccagtggaatgatgatgttcatacactgcatattcttccggcatggaatgaaaatgttgttgcaaaaggctcaggcaataa
tgttccggttgtcgtttatacagatgcagcgaaagtgaaactgtattttacaccgaaaggctcaacagaaaaaagactgatcggcga
aaaatcatttacaaaaaaaacaacagcggcaggctatacatatcaagtctatgaaggcagcgataaagattcaacagcgcataaa
aacatgtatctgacatggaatgttccgtgggcagaaggcacaatttcagcggaagcgtatgatgaaaataatcgcctgattccgaa
ggcagcacagaaggcaacgcatcagttacaacaacaggcaaagcagcaaaactgaaagcagatgcggatcgcaaaacaattac
agcggatggcaaagatctgtcatatattgaagtcgatgtcacagatgcaaatggccatattgttccggatgcagcaaatagagtcac
atttgatgttaaaggcgcaggcaaactggttggcgttgataatggctcatcaccggatcatgattcatatcaagcggataaccgcaa
agcattttcaggcaaagtcctggcaattgttcagtcaacaaaagaagcaggcgaaattacagttacagcaaaagcagatggcctgc
aatcaagcacagttaaaattgcaacaacagcagttccgggaacaagcacagaaaaaacagtccgcagcttttattacagccgcaac
tattatgtcaaaacaggcaacaaaccgattctgccgtcagatgttgaagttcgctattcagatggaacaagcgatagacaaaacgtt
acatgggatgcagtttcagatgatcaaattgcaaaagcaggctcattttcagttgcaggcacagttgcaggccaaaaaattagcgttc
gcgtcacaatgattgatgaaattggcgcactgctgaattattcagcaagcacaccggttggcacaccggcagttcttccgggatcaa
gaccggcagtcctgccggatggcacagtcacatcagcaaattttgcagtccattggacaaaaccggcagatacagtctataatacag
caggcacagtcaaagtaccgggaacagcaacagttttttggcaaagaatttaaagtcacagcgacaattagagttcaaagaagcca
agttacaattggctcatcagtttcaggaaatgcactgagactgacacaaaatattccggcagataaacaatcagatacactggatgc
gattaaagatggctcaacaacagttgatgcaaatacaggcggaggcgcaaatccgtcagcatggacaaattgggcatattcaaaa
gcaggccataacacagcggaaattacatttgaatatgcgacagaacaacaactgggccagatcgtcatgtatttttttcgcgatagca
atgcagttagatttccggatgctggcaaaacaaaaattcagatcagcgcagatggcaaaaattggacagatctggcagcaacaga
aacaattgcagcgcaagaatcaagcgatagagtcaaaccgtatacatatgattttgcaccggttggcgcaacatttgttaaagtgac
agtcacaaacgcagatacaacaacaccgtcaggcgttgtttgcgcaggcctgacagaaattgaactgaaaacagcgacaagcaaa
tttgtcacaaatacatcagcagcactgtcatcacttacagtcaatggcacaaaagtttcagattcagttctggcagcaggctcatataa
cacaccggcaattatcgcagatgttaaagcggaaggcgaaggcaatgcaagcgttacagtccttccggcacatgataatgttattcg
cgtcattacagaaagcgaagatcatgtcacacgcaaaacatttacaatcaacctgggcacagaacaagaattt >SEQ ID NO: 15 forward primer for generation of BIF variants
GGGGTAACTAGTGGAAGATGCAACAAGAAG

LIST OF SEQUENCES

>SEQ ID NO: 16 reverse primer for BIF917
GCGCTTAATTAATTATGTTTTTTCTGTGCTTGTTC

>SEQ ID NO: 17 reverse primer for BIF995
GCGCTTAATTAATTACAGTGCGCCAATTTCATCAATCA

>SEQ ID NO: 18 reverse primer for BIF1068
GCGCTTAATTAATTATTGAACTCTAATTGTCGCTG

>SEQ ID NO: 19 reverse primer for BIF1241
GCGCTTAATTAATTATGTCGCTGTTTTCAGTTCAAT

>SEQ ID NO: 20 reverse primer for BIF1326
GCGCTTAATTAATTAAAATTCTTGTTCTGTGCCCA

>SEQ ID NO: 21 reverse primer for BIF1478
GCGCTTAATTAATTATCTCAGTCTAATTTCGCTTGCGC >SEQ ID NO: 22 Bifidobacterium bifidum BIF1750
vedatrsdsttqmsstpevvyssavdskqnrtsdfdanwkfmlsdsvqaqdpafddsawqqvdlphdysitqkysqsneaesa
ylpggtgwyrksftidrdlagkriainfdgvymnatvwfngvklgthpygyspfsfdltgnakfggentivvkvenrlpssrwysgsg
iyrdvtltvtdgvhvgnngvaiktpslatqnggdvtmnlttkvandteaaanitlkqtvfpkggktdaaigtvttasksiaagasadvt
stitaaspklwsiknpnlytvrtevlnggkvldtydteygfrwtgfdatsgfslngekvklkgvsmhhdqgslgavanrraierqveil
qkmgvnsirtthnpaakalidvcnekgvlvveevfdmwnrskngntedygkwfgqaiagdnavlggdkdetwakfdltstinrdr
napsvimwslgnemmegisgsvsgfpatsaklvawtkaadstrpmtygdnkikanwnesntmgdnltanggvvgtnysdga
nydkirtthpswaiygsetasainsrgiynrttggaqssdkqltsydnsavgwgavassawydvvqrdfvagtyvwtgfdylgept
pwngtgsgavgswpspknsyfgivdtagfpkdtyyfyqsqwndvhtlhilpawnenvvakgsgnnvpvvvytdaakvklyft
pkgstekrligeksftkkttaagytyqvyegsdkdstahknmyltwnvpwaegtisaeaydennrlipegstegnasvtttgkaak
lkadadrktitadgkdlsyievdvtdanghivpdaanrvtfdvkgagklvgvdngsspdhdsyqadnrkafsgkvlaivqstkeag
eitvtakadglqsstvkiattavpgtstektvrsfyysrnyyvktgnkpilpsdvevrysdgtsdrqnvtwdavsddqiakagsfsva
gtvaggkisvrvtmideigallnysastpvgtpavlpgsrpavlpdgtvtsanfavhwtkpadtvyntagtvkvpgtatvfgkefkvt
atirvqrsqvtigssvsgnalrltqnipadkqsdtldaikdgsttvdantgggganpsawtnwayskaghntaeitfeyateqqlgqiv
myffrdsnavrfpdagktkiqisadgknwtdlaatetiaaqessdrvkpytydfapvgatfvkvtvtnadttttpsgvvcaglteielkt
atskfvtntsaalssltvngtkvsdsvlaagsyntpaiiadvkaegegnasvtvlpahdnvirvitesedhvtrktftinlgteqefpads
derdypaadmtvtvgseqtsgtategpkkfavdgntstywhsnwtpttvndlwiafelqkptkldalrylprpagskngsvteykv
qvsddgtnwtdagsgtwttdygwklaefnqpvttkhvrlkavhtyadsgndkfmsaseirlrkavdttdisgatvtvpakltvdrvd
adhpatfatkdvtvtlgdatlrygvdylldyagntavgkatvtvrgidkysgtvaktftielknapapeptltsvsvktkpskltyvvgd
afdpaglvlqhdrqadrppqplvgeqadergltcgtrcdrveqlrkhenreahrtgldhlefvgaadgavgeqatfkvhvhadqgd
grhddaderdidphvpvdhavgelaraachhviglrvdthrlkasgfqipaddmaeidritgfhrferhvg >SEQ ID NO: 23 The signal sequence of extracellular lactase from Bifidobacterium
bifidum DSM20215
Vrskklwisllfalaliftmafgstssaqa

What is claimed is:

1. A polypeptide having transgalactosylating activity consisting of:
a truncated polypeptide consisting of an amino acid sequence having at least 98% sequence identity to SEQ ID NO: 1 (amino acids 1 to 887), wherein the polypeptide has a ratio of transgalactosylating activity: β-galactosidase activity of at least 1.5.

2. The polypeptide according to claim 1, wherein said truncated polypeptide consists of the amino acid sequence of SEQ ID NO: 1.

3. An isolated nucleic acid encoding the polypeptide according to claim 1.

4. An expression vector comprising the nucleic acid according to claim 3.

5. An isolated microbial cell for expressing the polypeptide according to claim 1.

6. A method of expressing a polypeptide, the method comprising culturing the cell of claim 5 and optionally purifying the polypeptide from the cell.

7. A composition comprising the polypeptide of claim 1, wherein the composition is a food composition or a dairy product.

8. A method for producing a food product by treating a substrate comprising lactose with a polypeptide as defined claim 1.

9. A method for producing a dairy product by treating a milk-based substrate comprising lactose with a polypeptide as defined in claim 1.

10. A process for producing galacto-oligosaccharides, comprising contacting a polypeptide of claim 1 with a milk-based solution comprising lactose.

11. A process for producing galacto-oligosaccharides, comprising contacting a purified polypeptide of claim 6 with a milk-based solution comprising lactose.

* * * * *